United States Patent
Gorgutsa et al.

(10) Patent No.: US 11,589,774 B2
(45) Date of Patent: Feb. 28, 2023

(54) WEARABLE RESPIRATION SENSOR AND RESPIRATION MONITORING SYSTEM

(71) Applicant: UNIVERSITÉ LAVAL, Québec (CA)

(72) Inventors: Stepan Gorgutsa, Québec (CA); Philippe Guay, Québec (CA); Younès Messadeq, Québec (CA); Sophie Larochelle, Québec (CA); Amine Miled, Québec (CA); Simon Bellemare-Rousseau, Québec (CA); Mourad Roudjane, Québec (CA); Marc-André Dugas, St-Augustin-de-Desmaures (CA)

(73) Assignee: UNIVERSITÉ LAVAL, Quebec (CA)

( * ) Notice: Subject to any disclaimer, the term of this patent is extended or adjusted under 35 U.S.C. 154(b) by 975 days.

(21) Appl. No.: 16/397,338

(22) Filed: Apr. 29, 2019

(65) Prior Publication Data

US 2019/0336038 A1    Nov. 7, 2019

(30) Foreign Application Priority Data

May 4, 2018 (CA) ................................ CA 3004071

(51) Int. Cl.
*A61B 5/08* (2006.01)
*A61B 5/00* (2006.01)
(Continued)

(52) U.S. Cl.
CPC ............ *A61B 5/0816* (2013.01); *A61B 5/082* (2013.01); *A61B 5/6804* (2013.01);
(Continued)

(58) Field of Classification Search
None
See application file for complete search history.

(56) References Cited

U.S. PATENT DOCUMENTS

| 4,308,872 A | 1/1982 | Watson et al. |
| 4,958,638 A | 9/1990 | Sharpe et al. |

(Continued)

FOREIGN PATENT DOCUMENTS

| EP | 2813176 A2 | 12/2014 |
| WO | 2014159773 A1 | 10/2014 |

OTHER PUBLICATIONS

Gorgutsa, Stepan, et al. "Washable hydrophobic smart textiles and multi-material fibers for wireless communication." Smart Materials and Structures 25.11 (2016): 115027.

(Continued)

*Primary Examiner* — Jay B Shah
(74) *Attorney, Agent, or Firm* — Alexandre Daoust; Norton Rose Fulbright LLP

(57) ABSTRACT

There is described a wearable respiration sensor generally having a stretchable substrate to be worn around a user's torso; and a dipole antenna having two flexible conductive elements extending in opposite directions from a center, relative to a dipole axis, and being secured to the stretchable substrate, each of the two flexible conductive elements having a proximate end near the center, a distal end away from the center, and a curved portion curving away from and back towards the dipole axis between the proximate end and the distal end, the two flexible conductive elements being in a point reflection symmetry relative to one another relative to said center in a manner that, when the stretchable substrate is stretched along the dipole axis, the curved portions of the two flexible conductive elements are flattened and the distal ends are moved away from one another.

29 Claims, 36 Drawing Sheets

(51) Int. Cl.
*A61B 5/0205* (2006.01)
*A61B 5/113* (2006.01)

(52) U.S. Cl.
CPC .......... *A61B 5/6823* (2013.01); *A61B 5/0205* (2013.01); *A61B 5/1135* (2013.01); *A61B 5/6831* (2013.01); *A61B 2562/164* (2013.01)

(56) References Cited

U.S. PATENT DOCUMENTS

| | | |
|---|---|---|
| 6,381,482 B1 | 4/2002 | Jayaraman et al. |
| 6,450,168 B1 | 9/2002 | Nguyen |
| 7,267,652 B2 | 9/2007 | Coyle et al. |
| 8,502,729 B2 | 8/2013 | Leach, Jr. et al. |
| 8,622,922 B2 | 1/2014 | Banet et al. |
| 8,668,653 B2 | 3/2014 | Nagata et al. |
| 8,870,785 B2 | 10/2014 | Muehlsteff et al. |
| 9,795,299 B2 | 10/2017 | Russell |
| 2010/0249633 A1 | 9/2010 | Droitcour et al. |
| 2010/0286546 A1 | 11/2010 | Tobola et al. |
| 2011/0060215 A1 | 3/2011 | Tupin, Jr. et al. |
| 2011/0112425 A1 | 5/2011 | Muhlsteff et al. |
| 2014/0070957 A1 | 3/2014 | Longinotti-Buitoni et al. |
| 2014/0350361 A1 | 11/2014 | De Chazal et al. |
| 2016/0150982 A1 | 6/2016 | Roy et al. |

OTHER PUBLICATIONS

Guay, Philippe, et al. "Wearable contactless respiration sensor based on multi-material fibers integrated into textile." Sensors 17.5 (2017): 1050.

Roudjane, Mourad, et al. "A Portable Wireless Communication Platform Based on a Multi-Material Fiber Sensor for Real-Time Breath Detection." Sensors 18.4 (2018): 973.

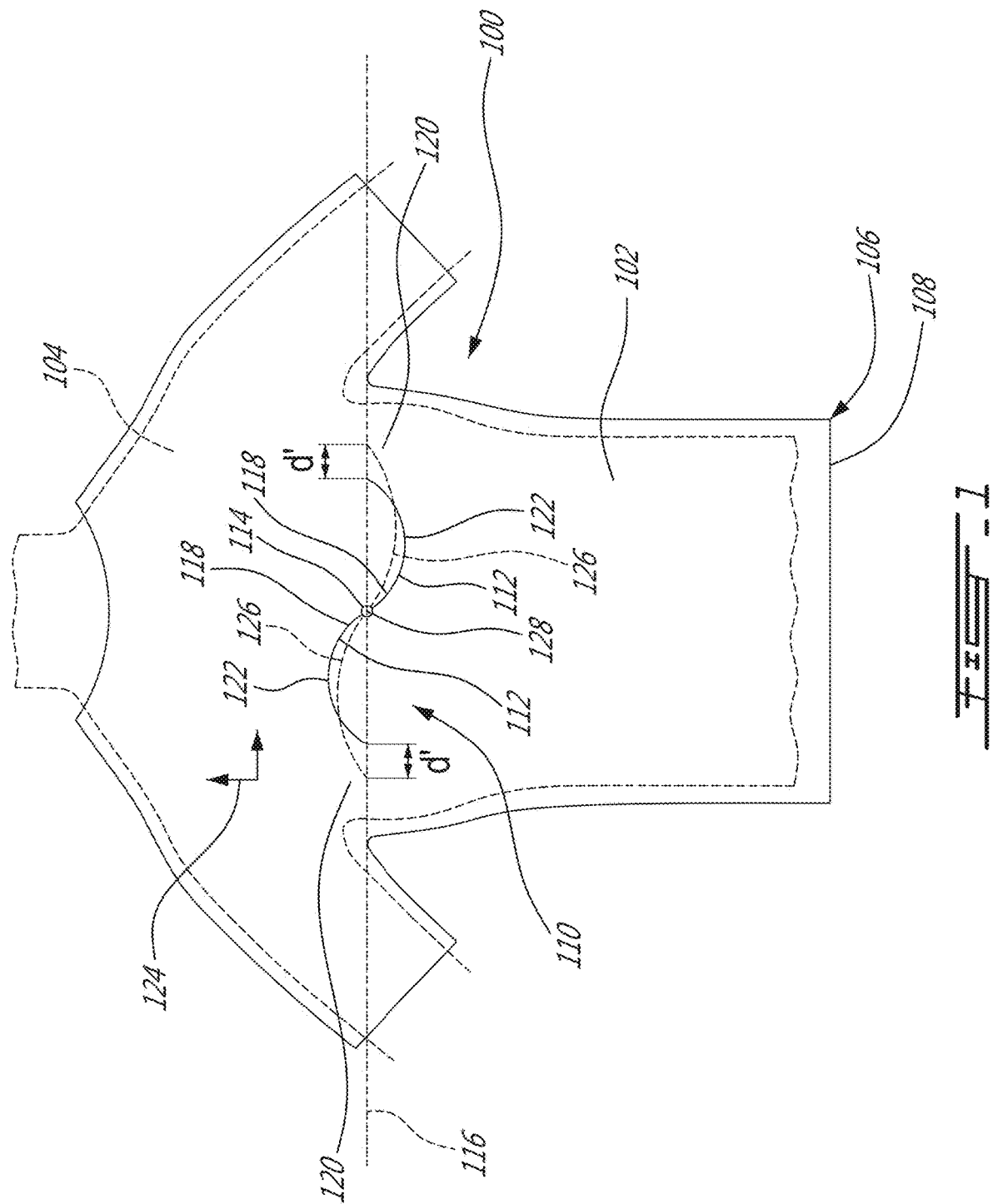

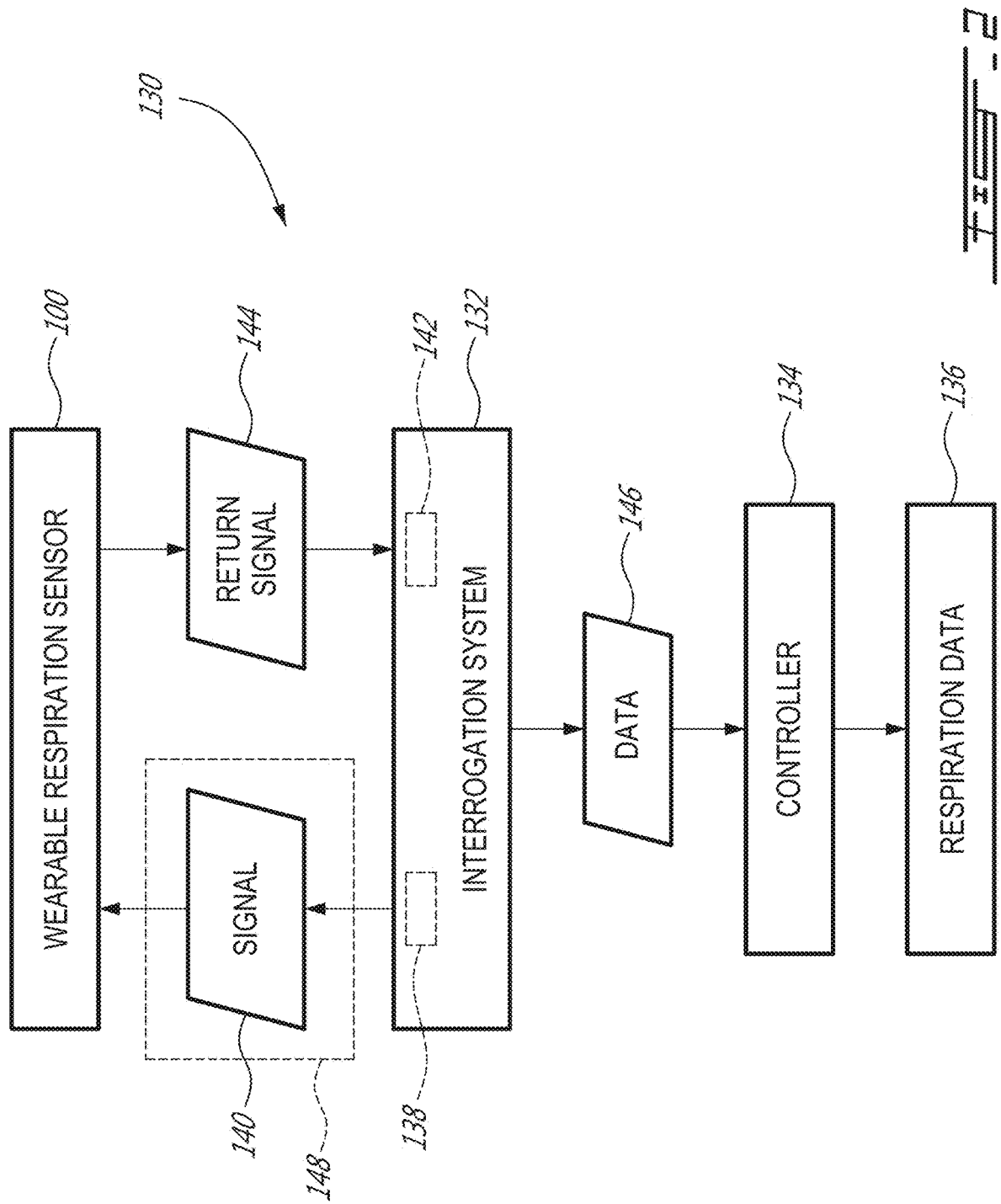

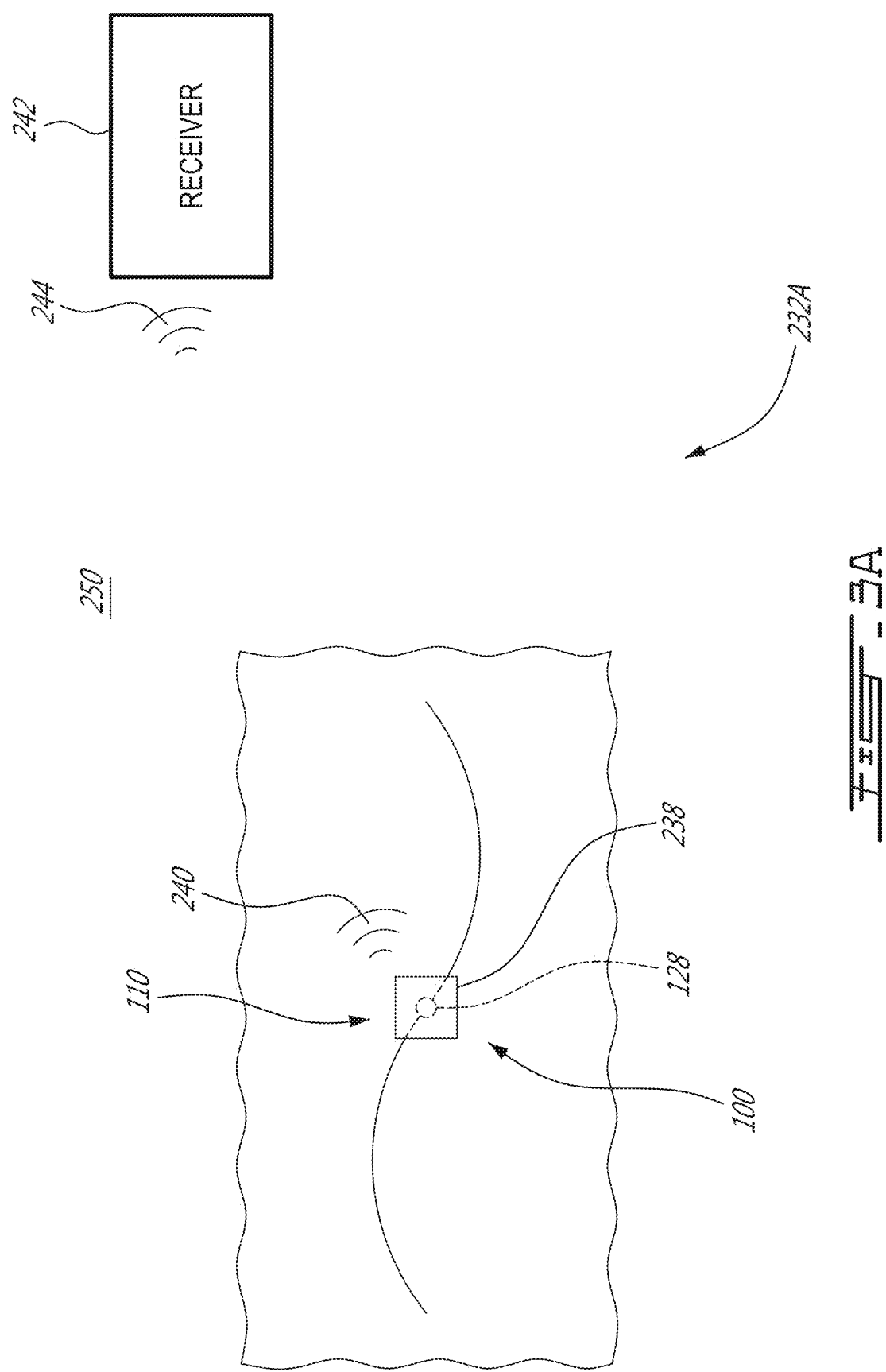

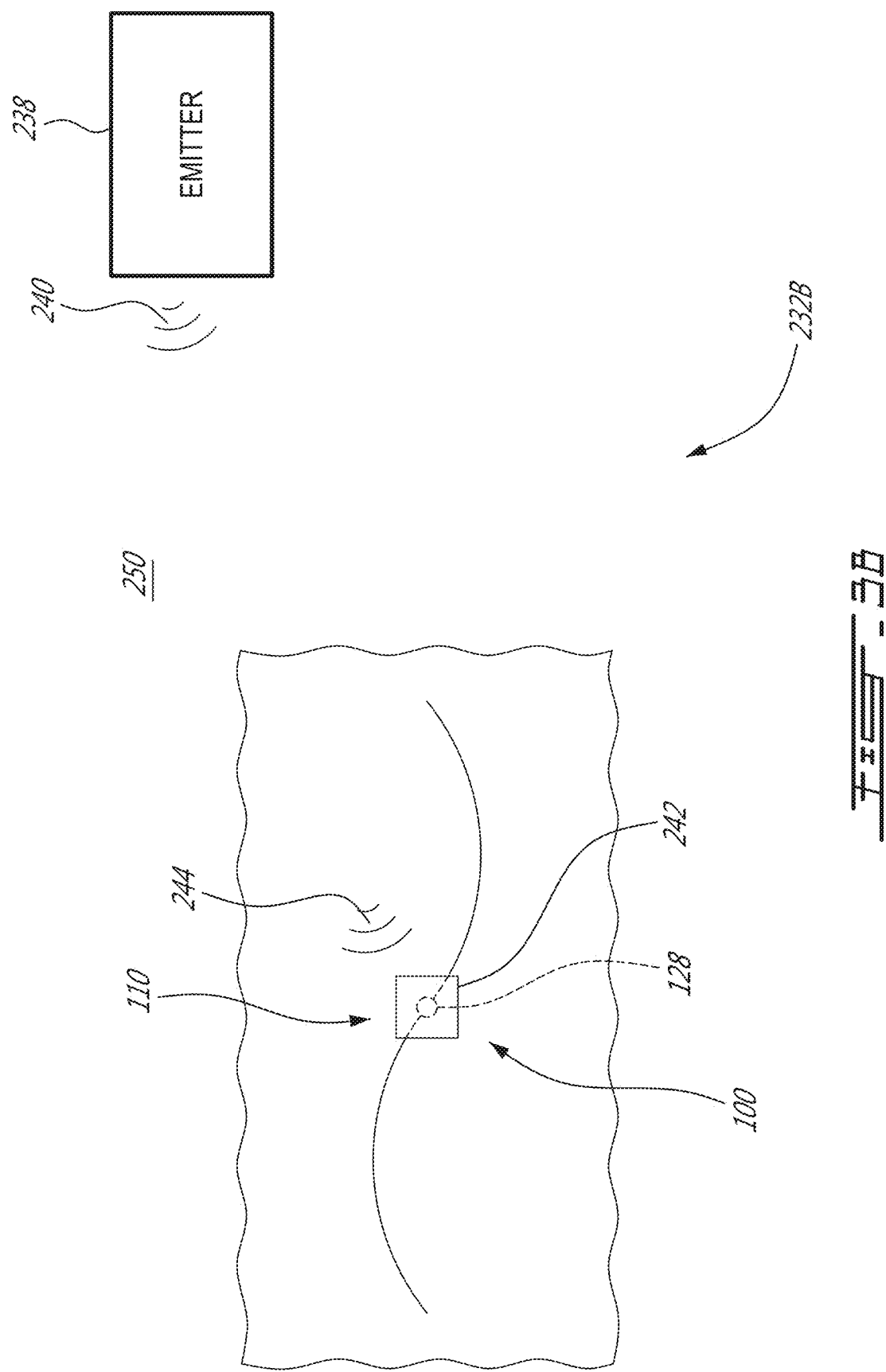

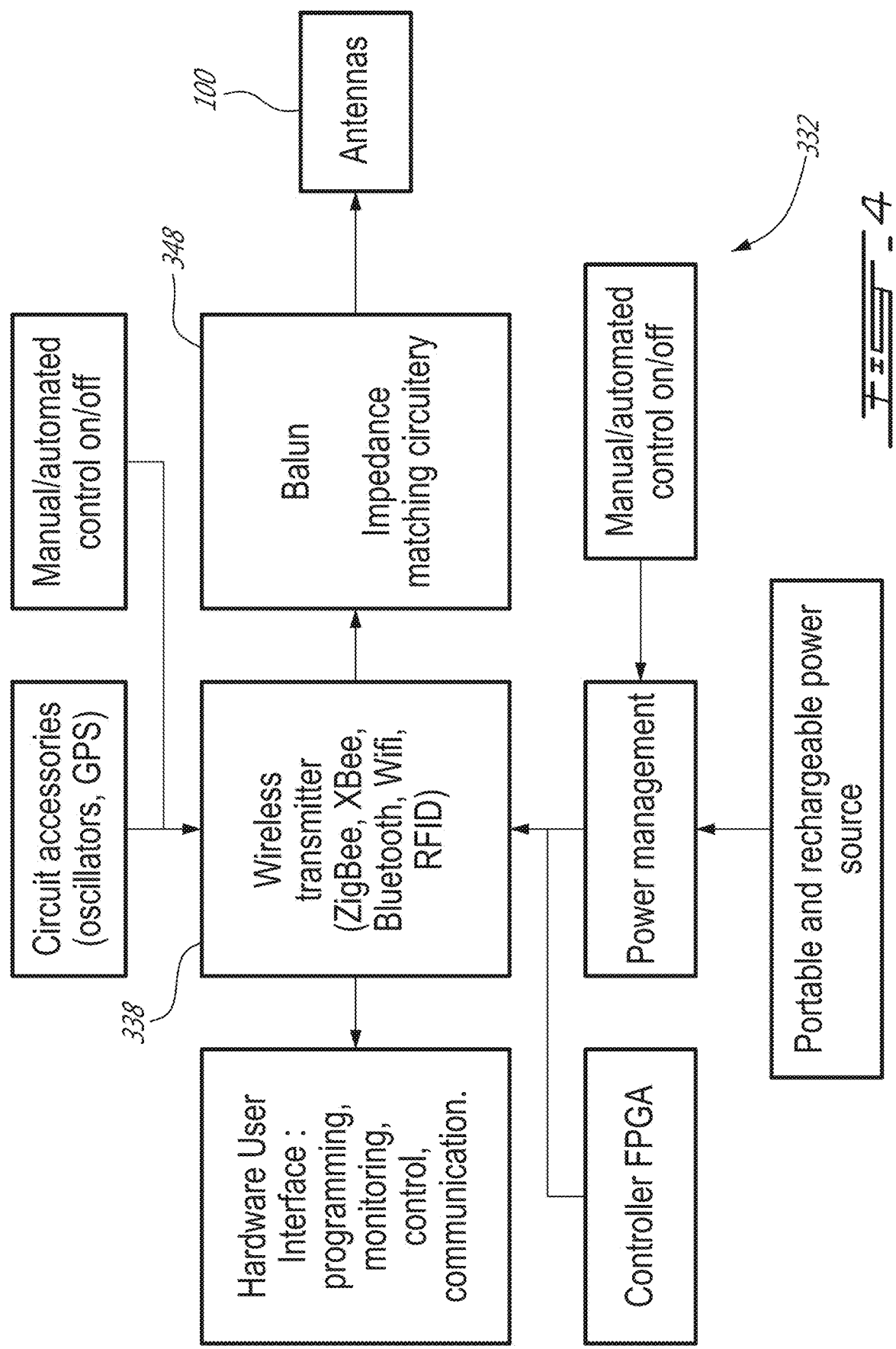

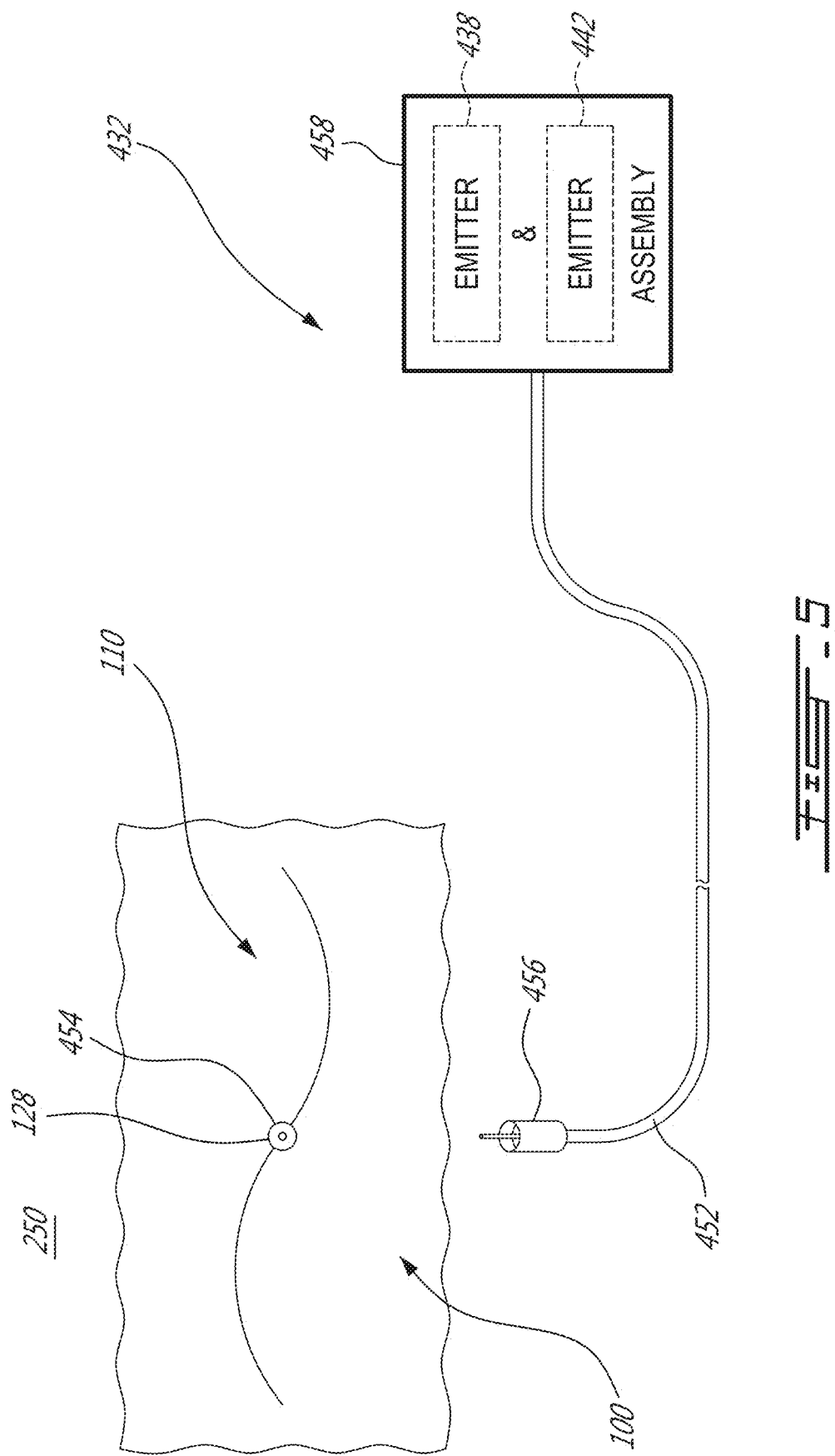

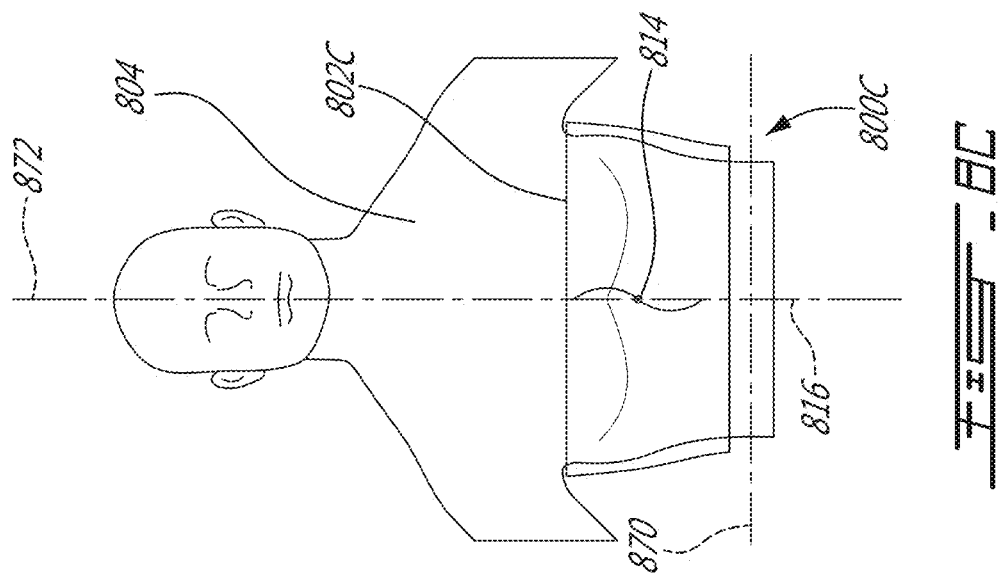
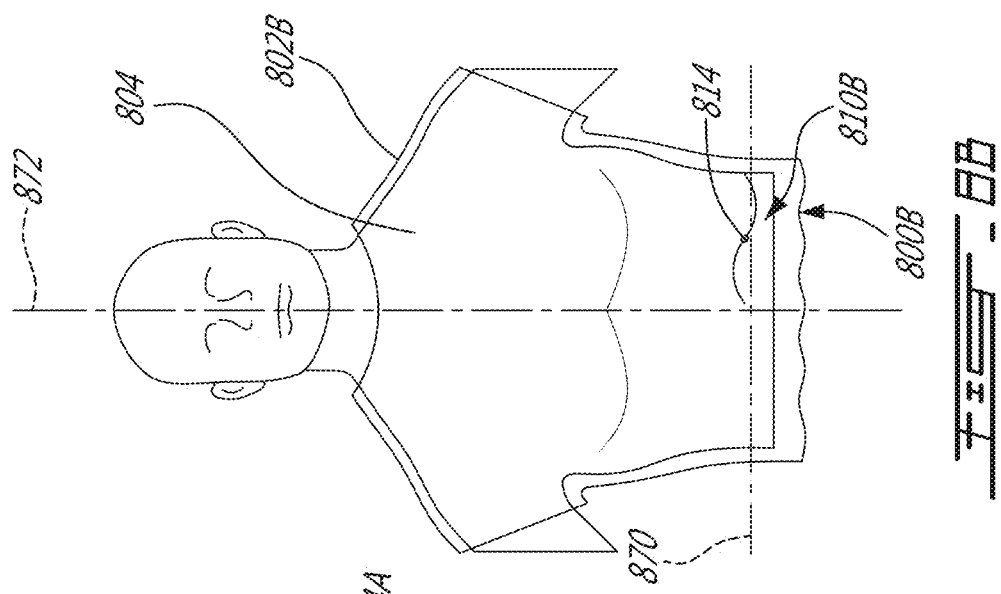
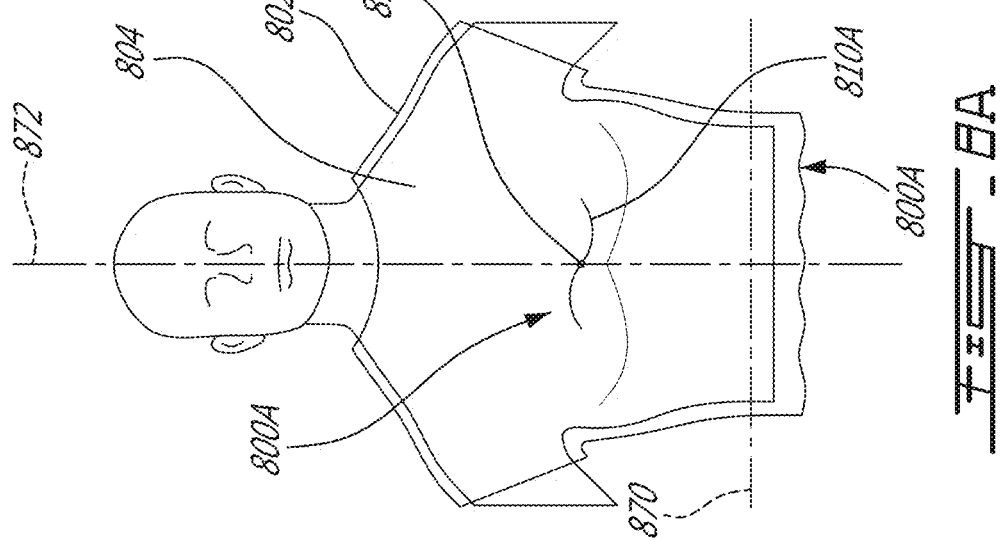

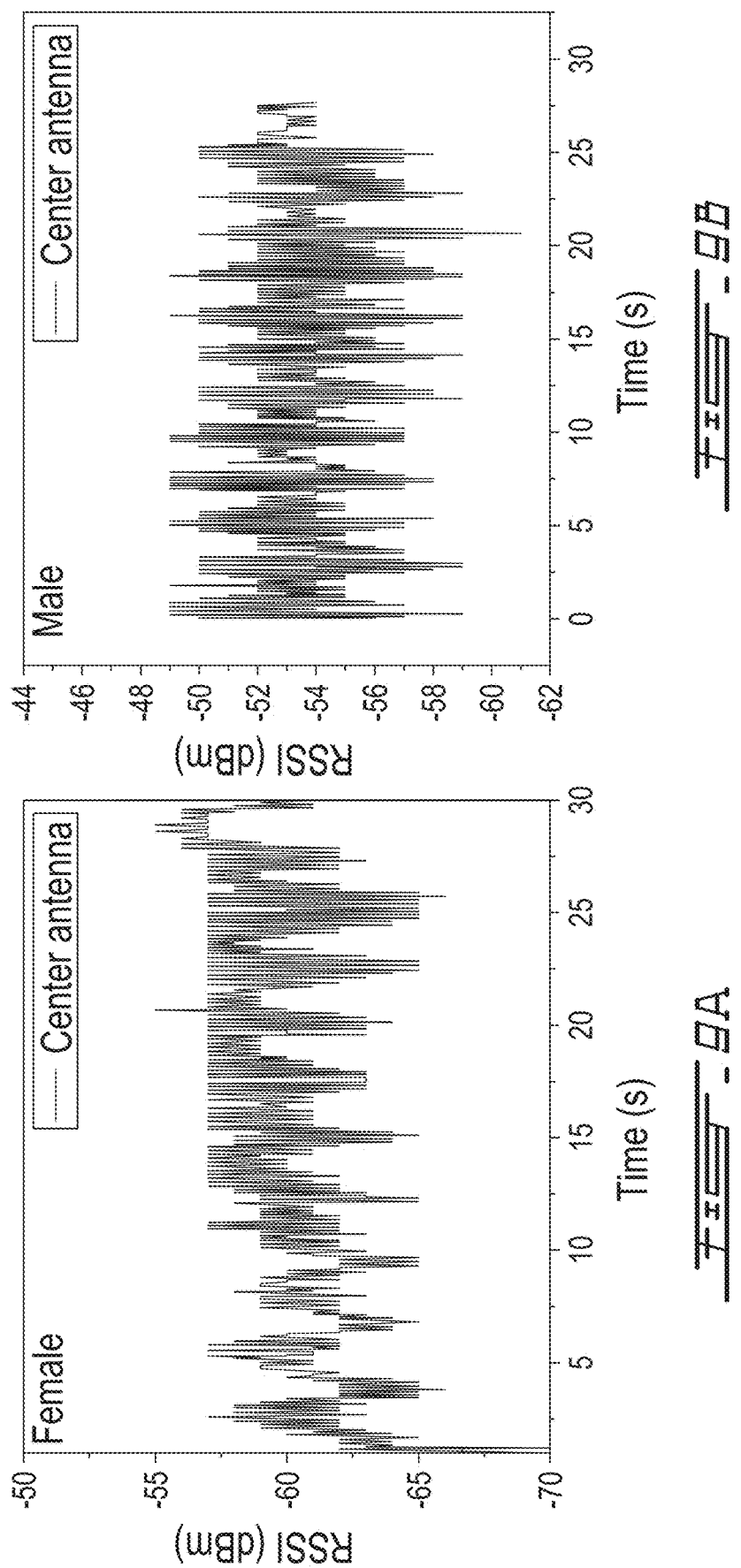

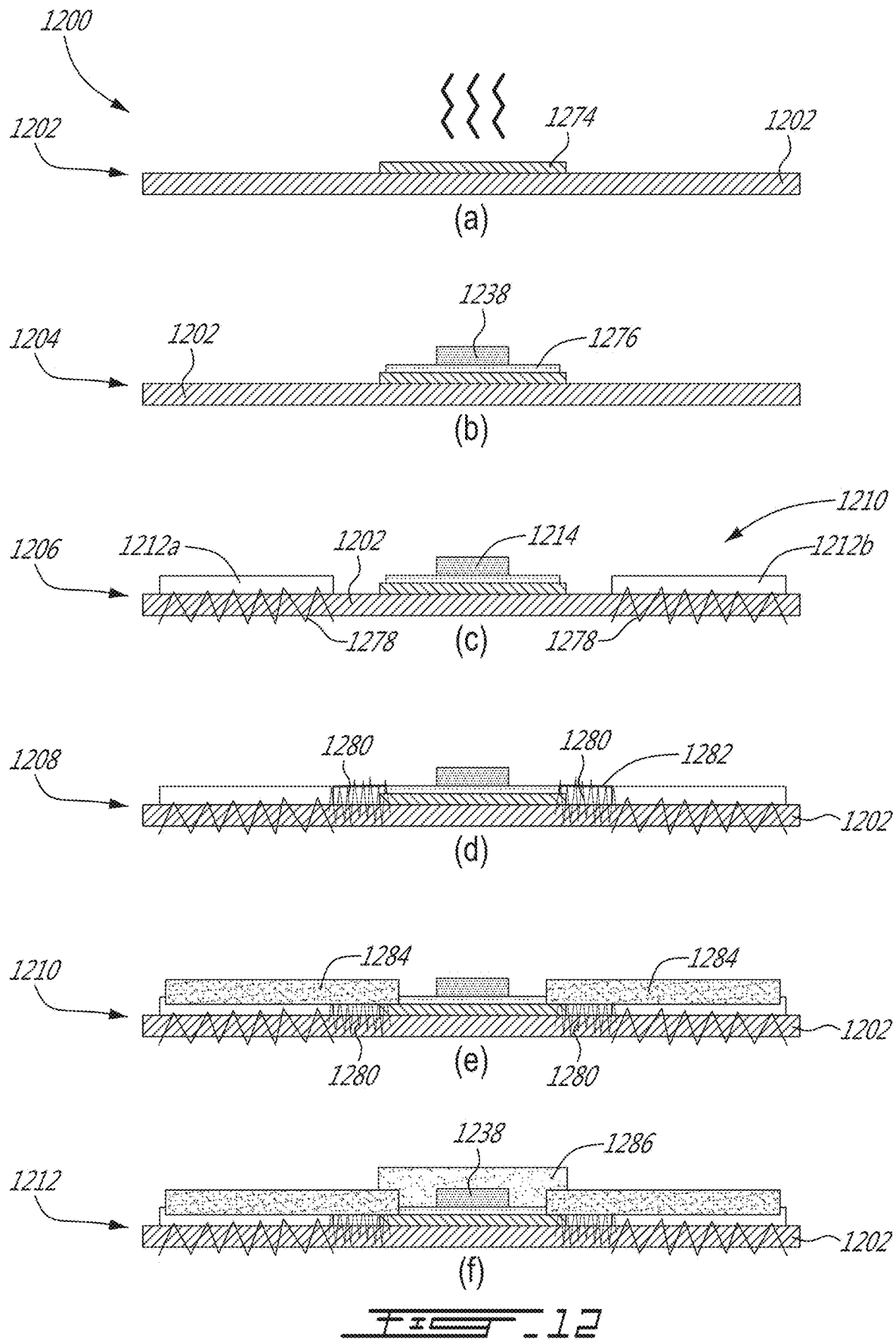

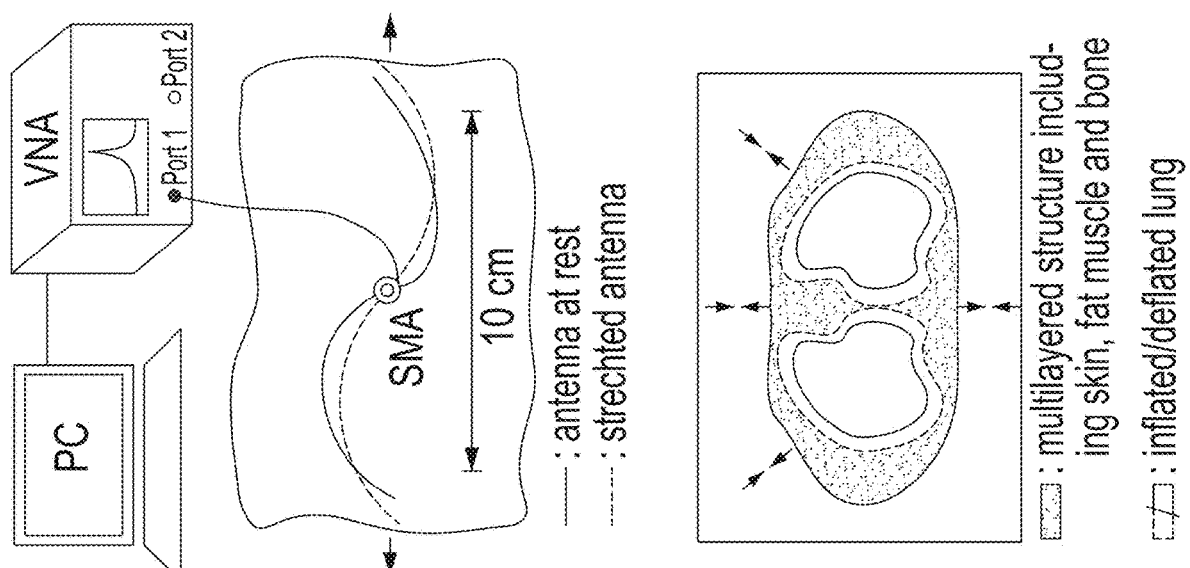
FIG. 16B
FIG. 16C
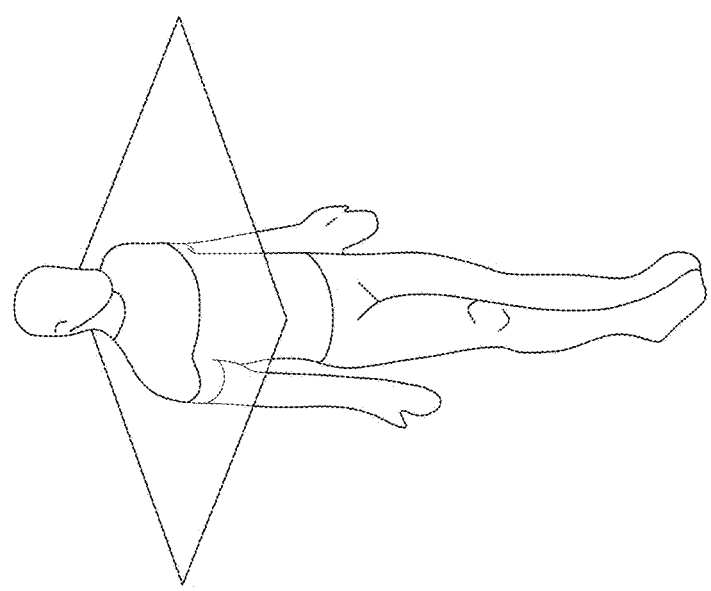
FIG. 16A

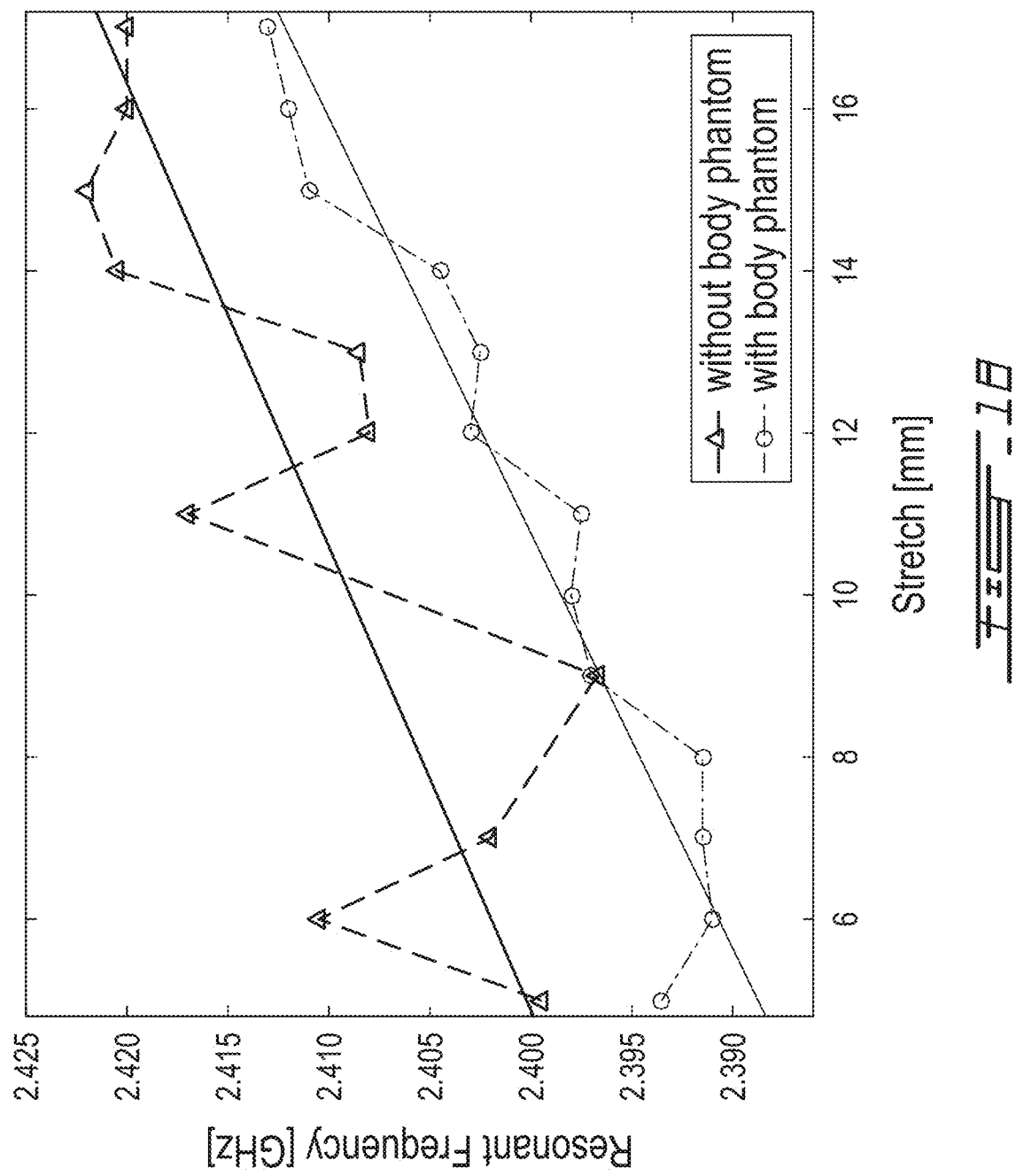

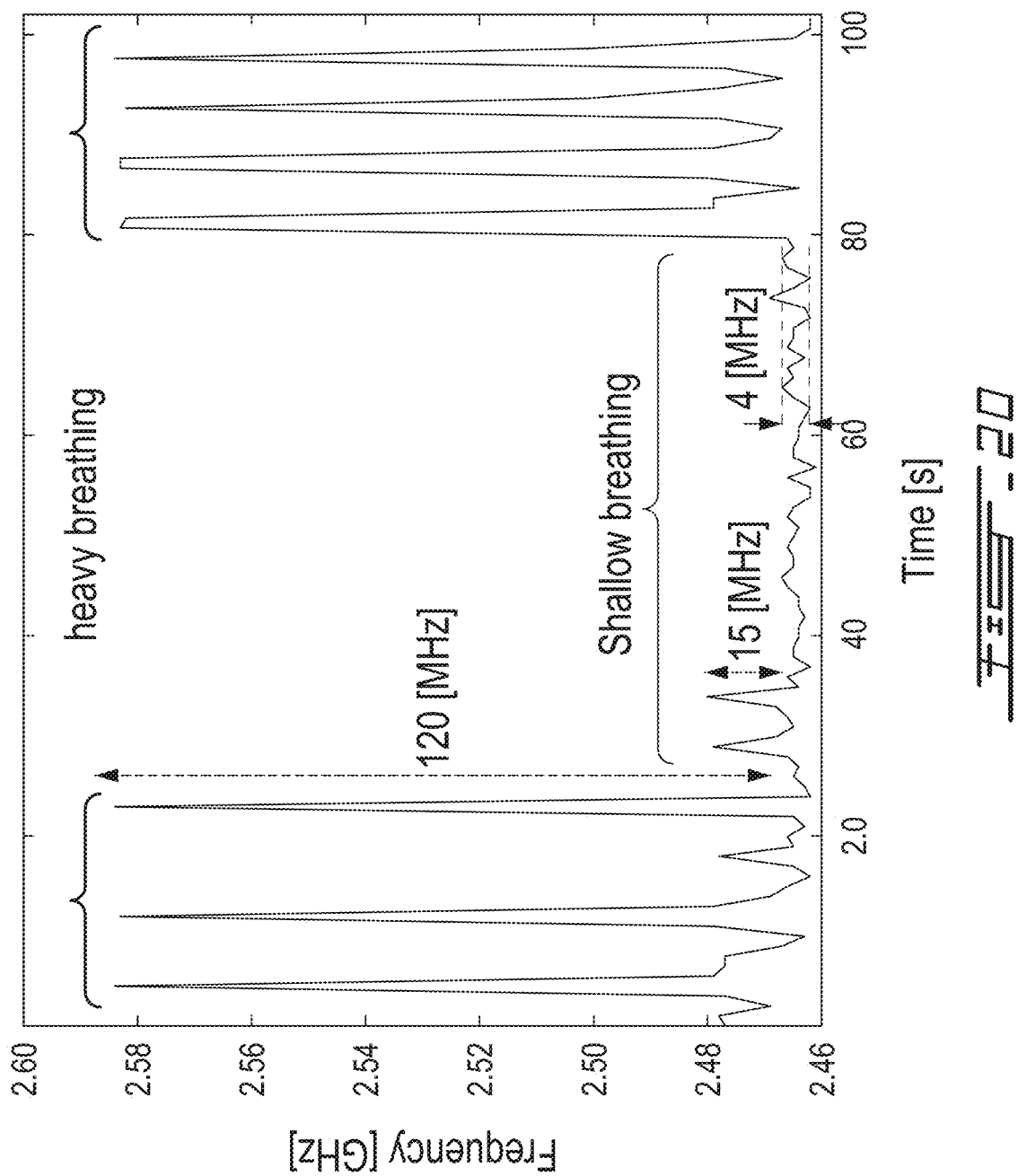

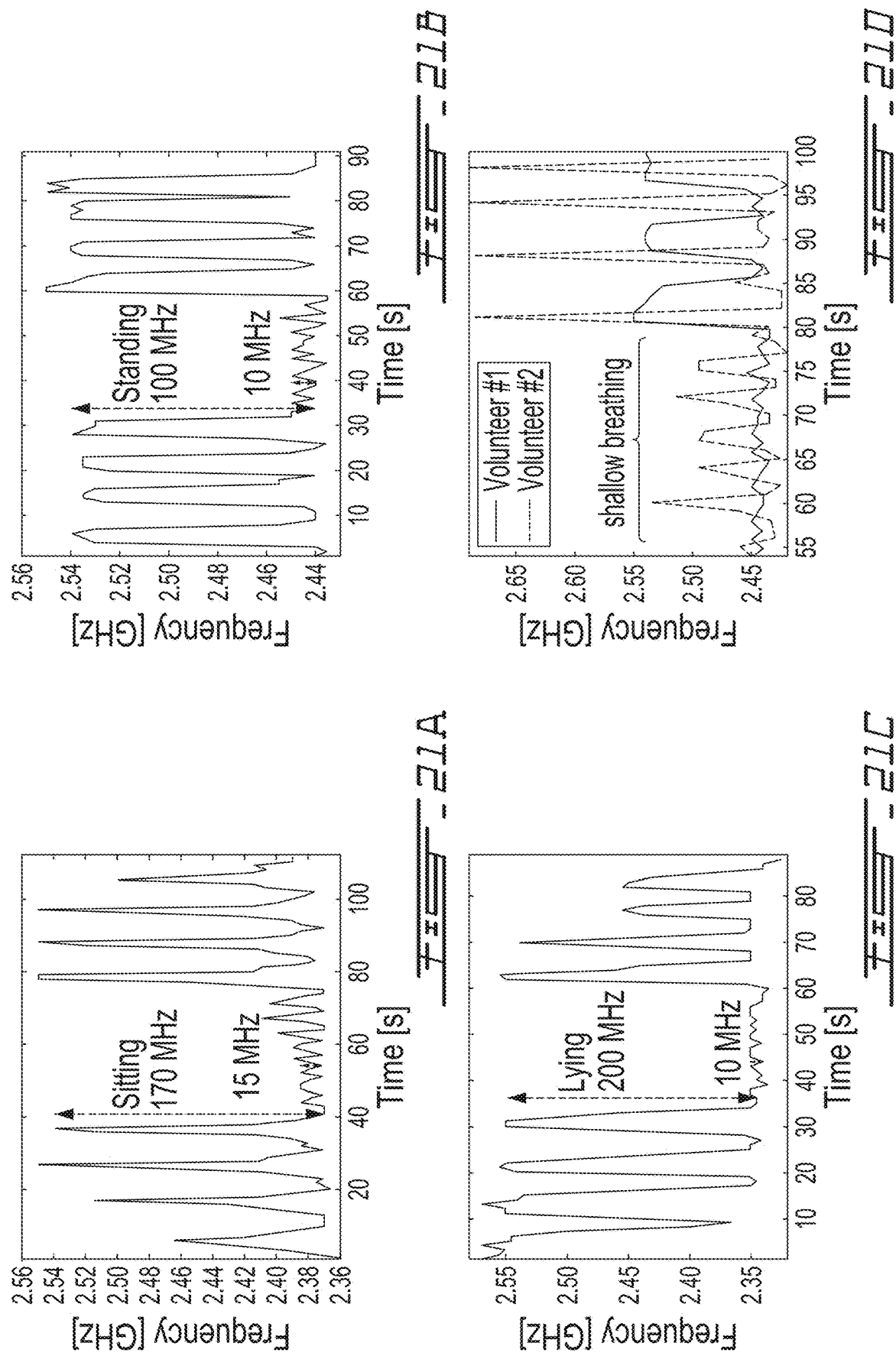

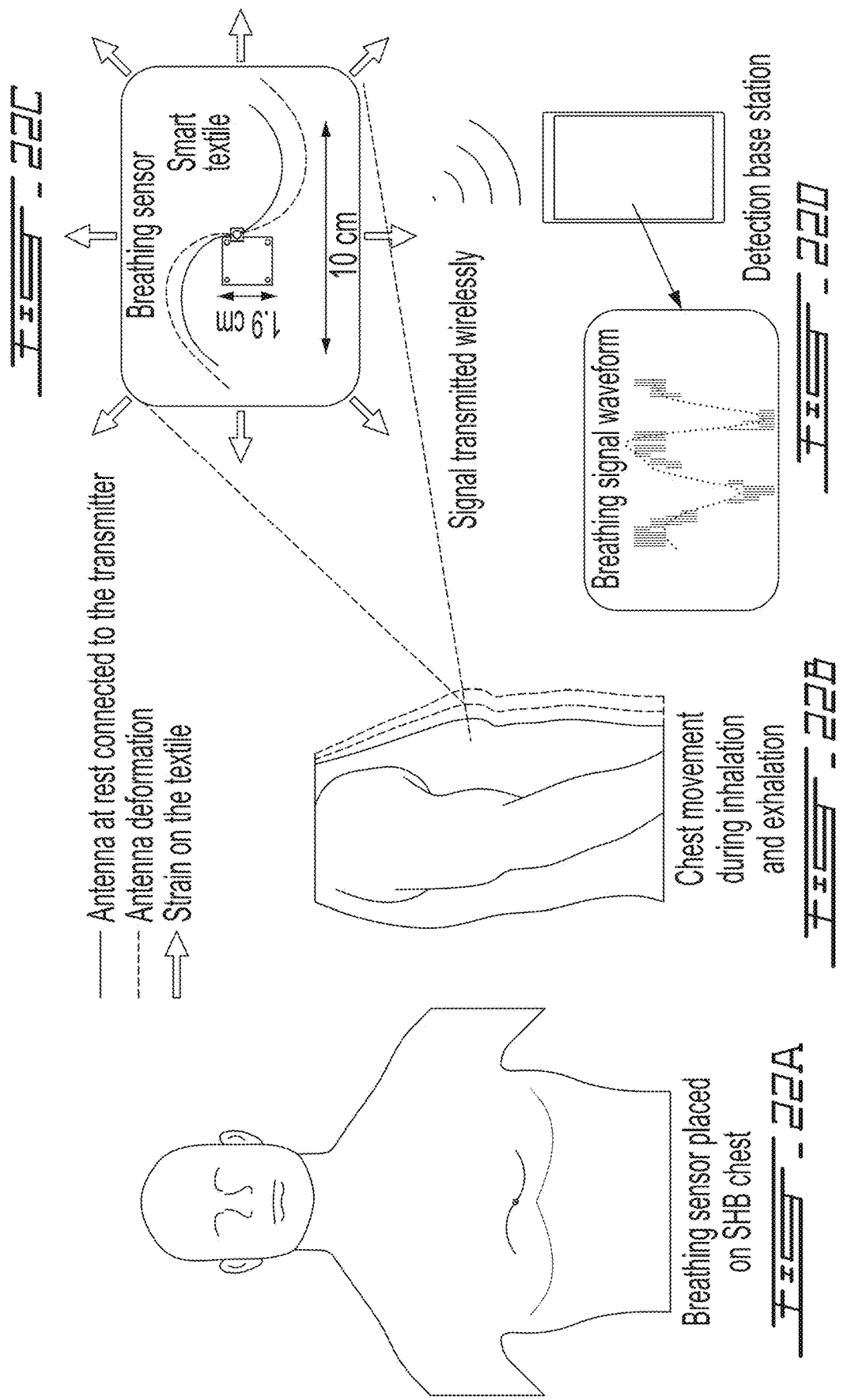

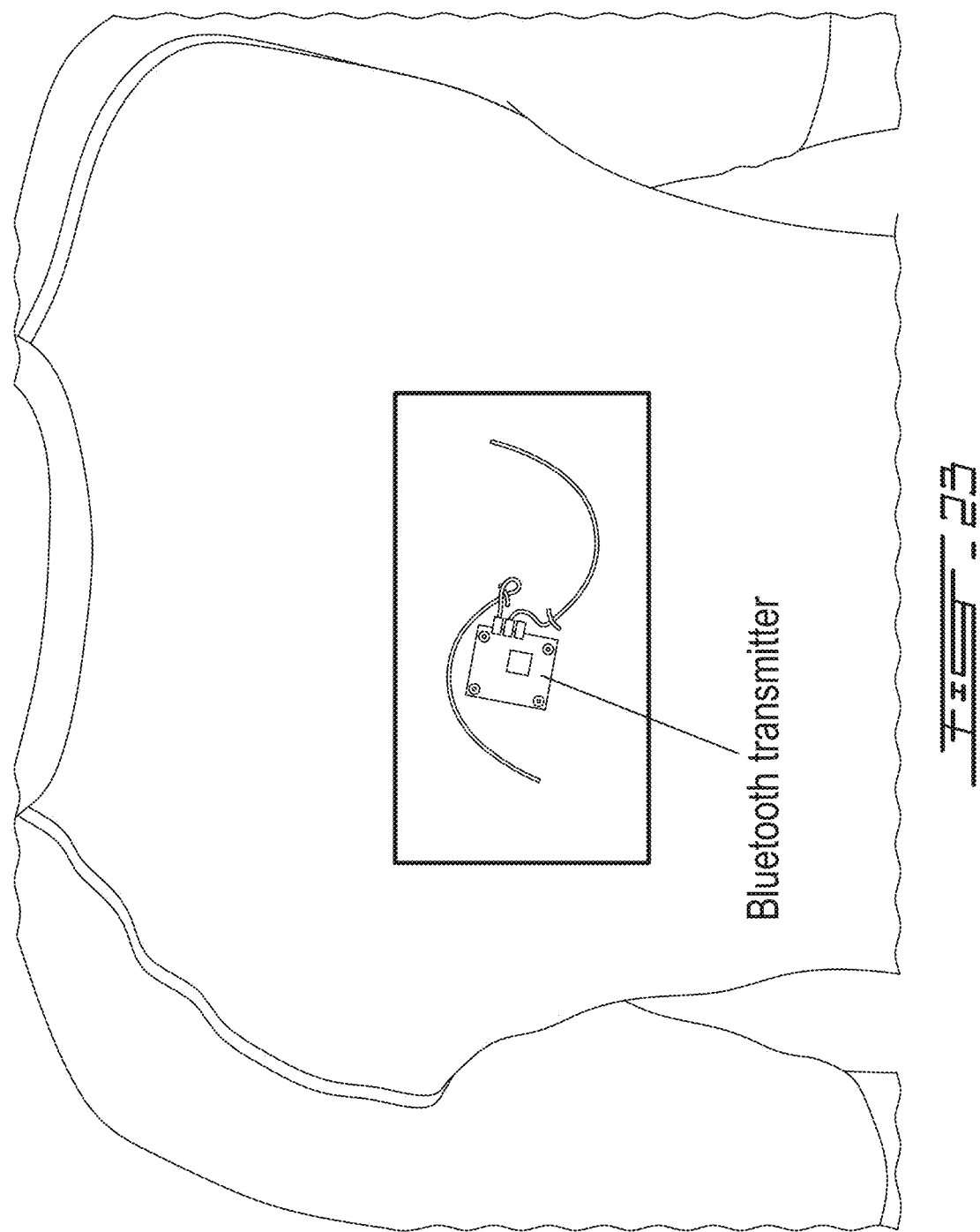

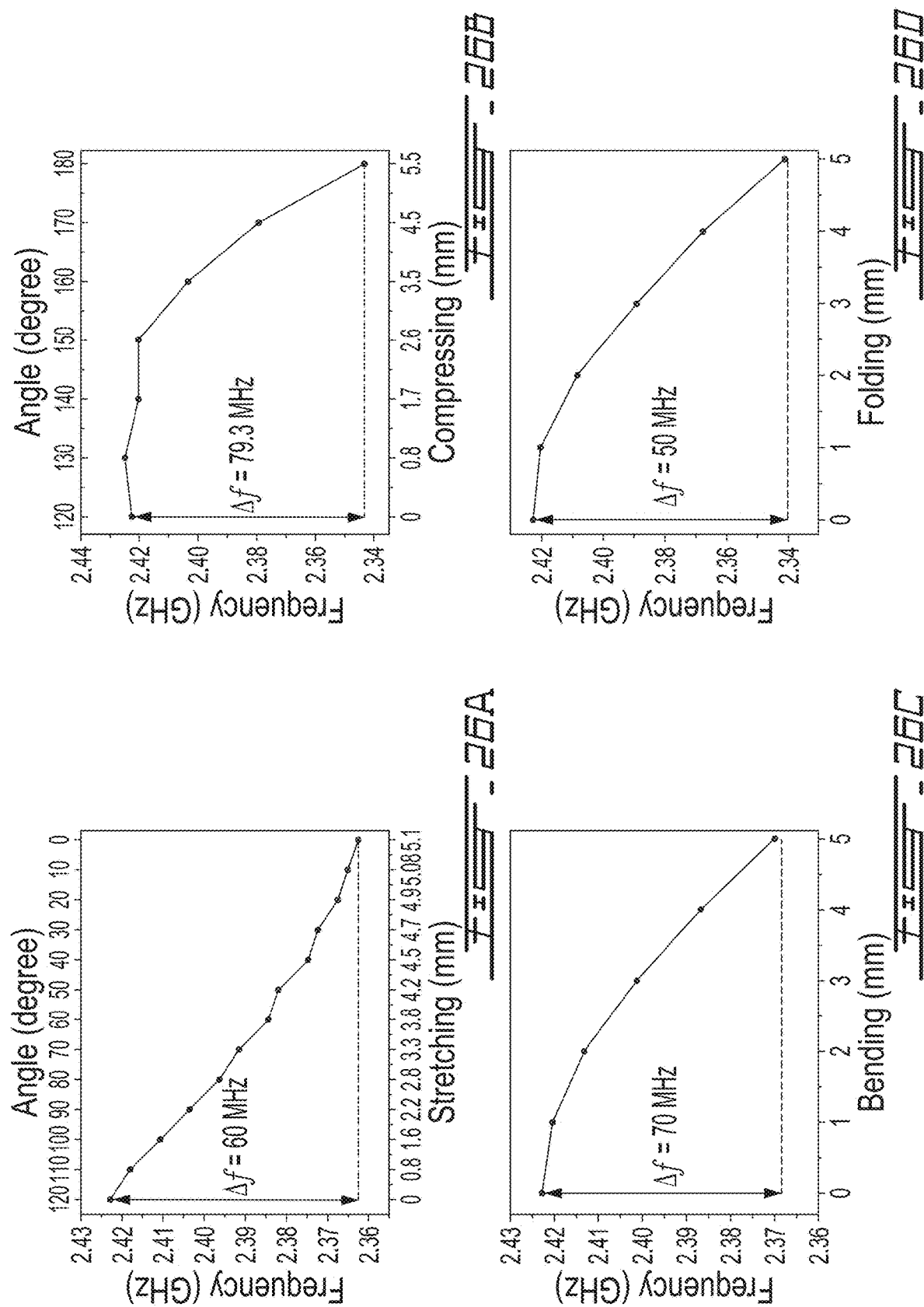

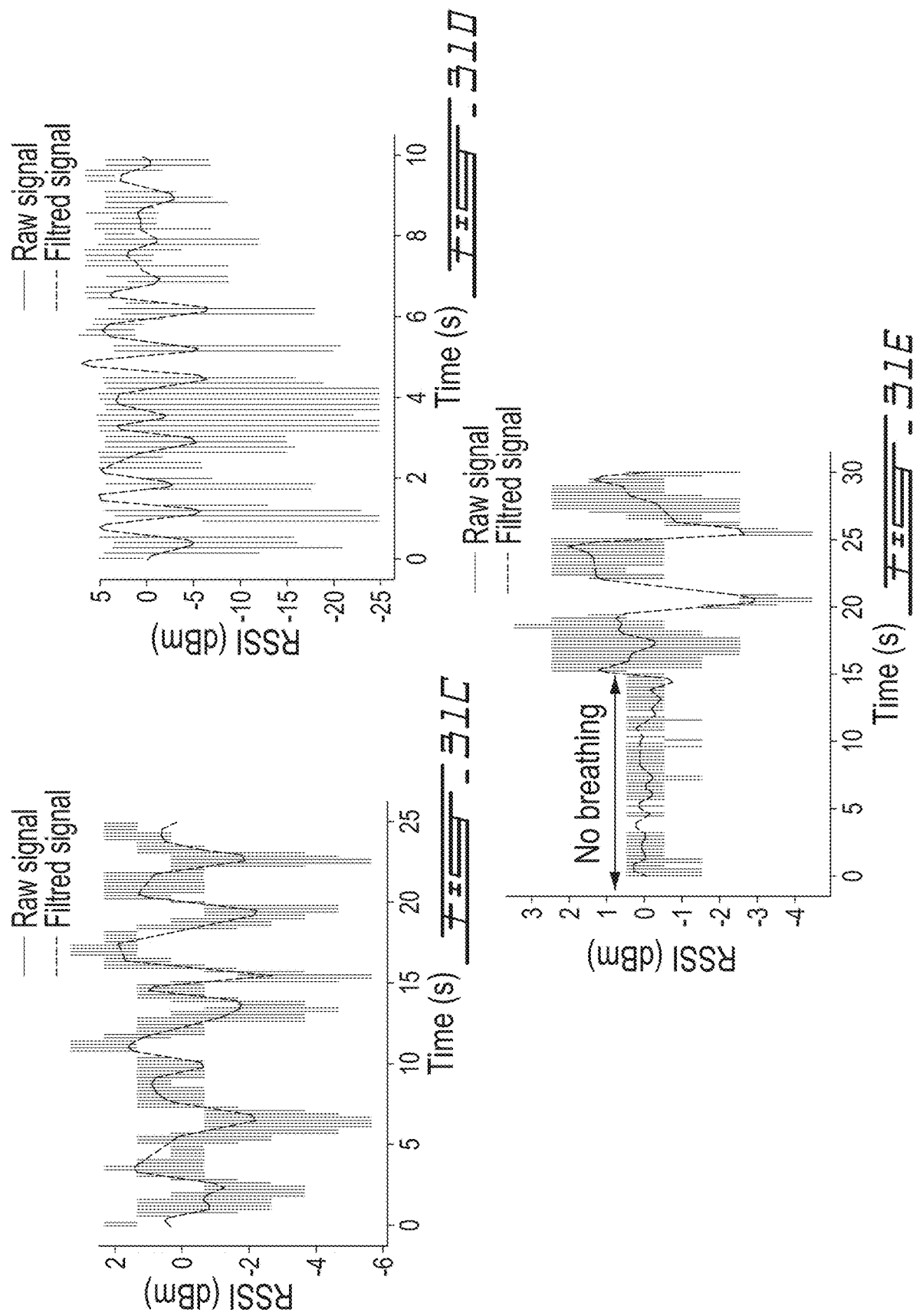

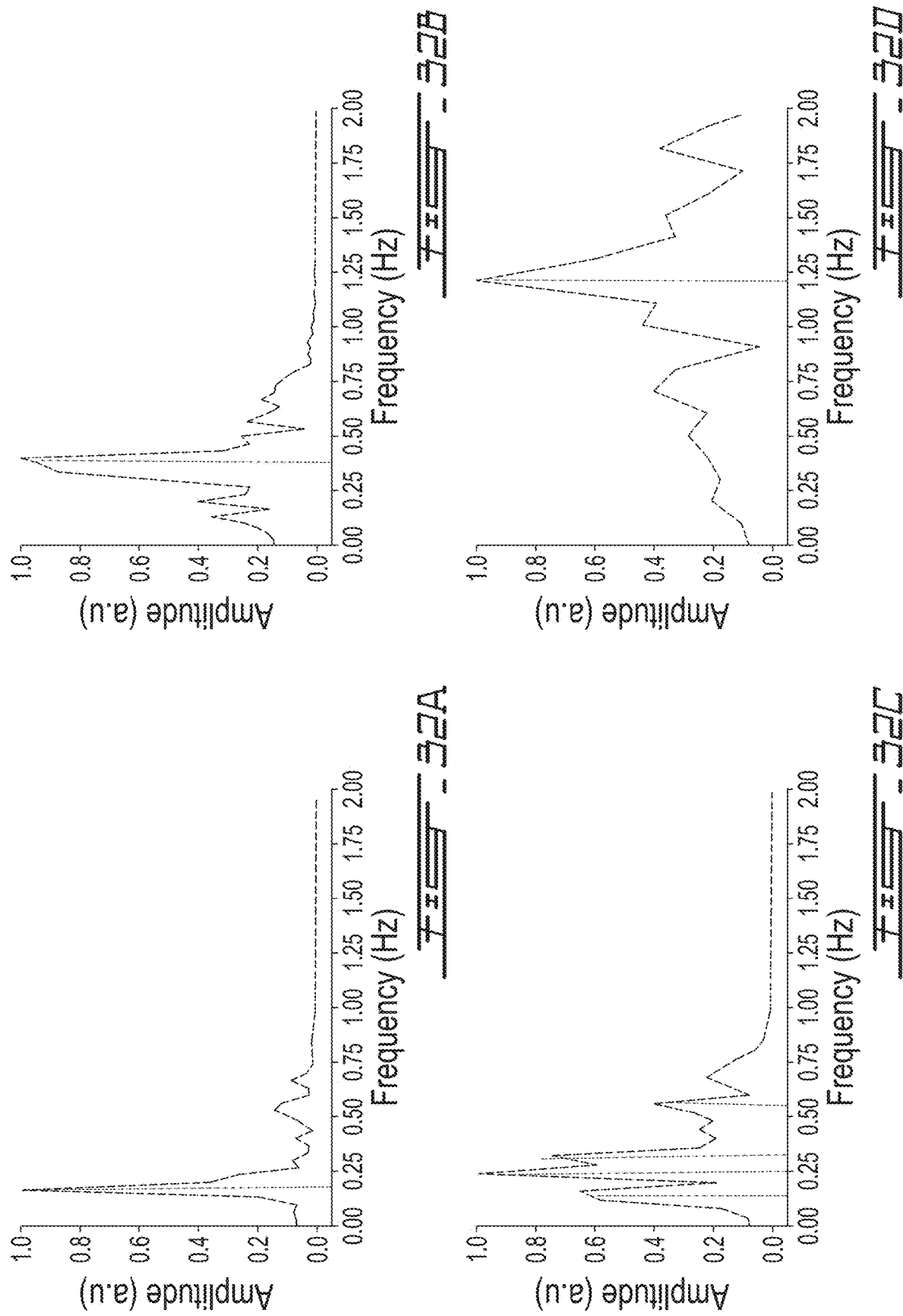

WEARABLE RESPIRATION SENSOR AND RESPIRATION MONITORING SYSTEM

FIELD

The improvements generally relate to the field of wearable sensors, and more specifically to wearable sensors to be worn around a user's torso for respiration sensing.

BACKGROUND

The respiration rate of a person is defined as the number of respirations or breaths the person takes per minute, i.e. bpm. Changes in the respiration rate can be considered to be an important indicator of major physiological and/or pathological conditions, such as cardiopulmonary disease, among others. For instance, in the case of adults at rest, a normal respiration rate can be about 14 bpm. However, categories of abnormal respiration rates for adults at rest can include hyperventilation when the respiration rate is sensed to be about 25 bpm, hypoventilation when the respiration rate is sensed to be about 10 bpm, and apnea when temporary cessation of respiration is sensed. Accordingly, many types of respiration sensors have been developed to monitor the respiration rate of a person.

Although existing respiration sensors are satisfactory to a certain degree, there remains room for improvement.

SUMMARY

In an aspect, there is described a wearable respiration sensor having a stretchable substrate configured to be worn around a user's torso. The respiration sensor has a dipole antenna with two flexible conductive elements extending in opposite directions from a center, relative to a dipole axis and being secured to the stretchable substrate. Each one of the two flexible conductive elements has a proximate end near the center, a distal end away from the center, and a curved portion curving away from and back towards the dipole axis between the proximate end and the distal end, in a plane of the stretchable substrate. The two flexible conductive elements are in a point reflection symmetry relative to one another relative to the center in a manner that, when the stretchable substrate is stretched along the dipole axis, the curved portions of the two flexible conductive elements are flattened and the distal ends are moved away from one another. The wearable respiration sensor has a receiving port being electrically connected to the two flexible conductive elements. In this way, when a signal is transmitted by the dipole antenna, a return signal, resulting from said transmission, can experience a variation as the dipole antenna is stretched in back and forth sequences as the user wearing the wearable respiration sensor breathes, and thus be indicative of the respiration rate of the user.

It was found that by using the respiration movement of the user's torso stretches the stretchable substrate so as to flatten the curve in the opposite flexible conductive elements and move the distal ends of the flexible conductive elements away or closer relative to one another as the user breathes, the way the dipole antenna works is altered. More specifically, the dipole antenna may work differently based on both the variation in shape of the dipole antenna and the variation in electromagnetic properties such as a permittivity of the user's torso as a function of the state of the lungs (e.g., full, intermediate, empty). Accordingly, an indication of the respiration of the user wearing the wearable respiration sensor can be obtained using an indication of the change in the return signal (e.g., a resonance frequency of the dipole antenna, a resonance frequency shift of the dipole antenna and/or a strength of the return signal). The change in the return signal stemming from the change in permittivity can be superposed, and therefore amplify rather than cancel the change in the return signal caused by change of geometry of the dipole antenna caused by its stretching and retraction.

In accordance with one aspect, there is provided a wearable respiration sensor comprising: a stretchable substrate configured to be worn around a user's torso; a dipole antenna having two flexible conductive elements extending in opposite directions from a center, relative to a dipole axis, and being secured to the stretchable substrate, each one of the two flexible conductive elements having a proximate end near the center, a distal end away from the center, and a curved portion curving away from and back towards the dipole axis between the proximate end and the distal end, in a plane of the stretchable substrate, the two flexible conductive elements being in a point reflection symmetry relative to one another relative to said center in a manner that, when the stretchable substrate is stretched along the dipole axis, the curved portions of the two flexible conductive elements are flattened and the distal ends are moved away from one another; and a receiving port being electrically connected to the two flexible conductive elements.

In accordance with one aspect, there is provided a respiration monitoring sensor comprising: a wearable respiration sensor having a stretchable substrate configured to be worn around a user's torso; a dipole antenna having two flexible conductive elements extending in opposite directions from a center, relative to a dipole axis, and being secured to the stretchable substrate, each one of the two flexible conductive elements having a proximate end near the center, a distal end away from the center, and a curved portion curving away from and back towards the dipole axis between the proximate end and the distal end, in a plane of the stretchable substrate, the two flexible conductive elements being in a point reflection symmetry relative to one another relative to said center in a manner that, when the stretchable substrate is stretched along the dipole axis, the curved portions of the two flexible conductive elements are flattened and the distal ends are moved away from one another; and a receiving port being electrically connected to the two flexible conductive elements; an interrogation system being communicatively coupled to the wearable respiration sensor, the interrogation system having an emitter configured to emit a signal for at least one of transmission and reception by the dipole antenna via the receiving port, and a receiver configured to, in response to said emission, receive a return signal varying as function of the stretching of the dipole antenna; and a controller being communicatively coupled to the interrogation system, the controller being configured to receive data concerning the return signal and to generate respiration data based on the received data.

In accordance with another embodiment, there is provided a wearable respiration sensor comprising a stretchable substrate to be worn around a user's torso; and a dipole antenna having two flexible conductive elements extending in opposite directions from a center, relative to a dipole axis, and being secured to the stretchable substrate, each of the two flexible conductive elements having a proximate end near the center, a distal end away from the center, and a curved portion curving away from and back towards the dipole axis between the proximate end and the distal end, the two flexible conductive elements being in a point reflection symmetry relative to one another relative to said center in a manner that, when the stretchable substrate is stretched along the dipole axis, the curved portions of the two flexible conductive elements are flattened and the distal ends are moved away from one another.

In a specific embodiment, the wearable respiration sensor is used for contactless monitoring of the respiration rate of a user wearing the wearable respiration sensor. The dipole antenna of the wearable respiration sensor includes two multimaterial curved fibers arranged in the form of spiral antenna and which are designed to operate at a frequency of 2.45 GHz frequency (e.g., Bluetooth, W-Fi). At least two complementary mechanisms can affect the way the dipole antenna works during respiration of the user. A first one of the two mechanisms is the modification of the geometry of the dipole antenna as the user breathes. A second one of the two mechanisms relates to the user's torso expansion and contraction which increases and decreases, respectively, the amount of air in the lungs, and affect the electromagnetic permittivity of the user's torso. Flexibility of the multimaterial curved fibers permits their integration into t-shirt (e.g., made of cotton) without compromising comfort or restricting movement of the user in this embodiment. Typical measured resonance frequency shifts for deep and shallow respiration was found to be in the range 120-200+ MHz and 10-15 MHz, respectively. In this embodiment, the dipole antenna is also shown to be suitable for short-range wireless communication, thus allowing real time or quasi real time respiration data transmission, for example via Bluetooth protocol to mobile handheld electronic devices.

It is intended that the wearable respiration sensor described herein can be used in different applications including, but not limited to: respiration monitoring of newborn infants in pediatric wards; respiration monitoring of elderly people; respiration monitoring of athletes and emergency first responders (e.g., firefighters, police officers); respiration monitoring of sleep clinic patients (e.g., sleep disordered breathing, obstructive sleep apnea); and any other suitable application where knowledge concerning respiration is sought.

It will be understood that the expression "worn around the torso" is not intended to be interpreted limitatively to mean "worn around an entire circumference of the torso". Indeed, in some embodiments, the stretchable substrate can be worn partially around the torso.

It will be understood that the expression 'computer' as used herein is not to be interpreted in a limiting manner. It is rather used in a broad sense to generally refer to the combination of some form of one or more processing units and some form of memory system accessible by the processing unit(s). Similarly, the expression 'controller' as used herein is not to be interpreted in a limiting manner but rather in a general sense of a device, or of a system having more than one device, performing the function(s) of controlling one or more device(s) such as an electronic device or an actuator for instance.

It will be understood that the various functions of a computer or of a controller can be performed by hardware or by a combination of both hardware and software. For example, hardware can include logic gates included as part of a silicon chip of the processor. Software can be in the form of data such as computer-readable instructions stored in the memory system. With respect to a computer, a controller, a processing unit, or a processor chip, the expression "configured to" relates to the presence of hardware or a combination of hardware and software which is operable to perform the associated functions.

Many further features and combinations thereof concerning the present improvements will appear to those skilled in the art following a reading of the instant disclosure.

DESCRIPTION OF THE FIGURES

In the figures,

FIG. 1 is a front view of an example of a wearable respiration sensor, in accordance with an embodiment;

FIG. 2 is a block diagram of an example of a respiration monitoring system having an wearable respiration sensor, an interrogation system and a controller, in accordance with an embodiment;

FIG. 3A is a schematic view of an example of the interrogation system of FIG. 2, with an emitter made integral to the wearable respiration sensor, in accordance with an embodiment;

FIG. 3B is a schematic view of another example of the interrogation system of FIG. 2, with a receiver made integral to the wearable respiration sensor, in accordance with an embodiment;

FIG. 4 is a block diagram of an example of the interrogation system of FIG. 3A, in accordance with an embodiment;

FIG. 5 is a schematic view of another example of the interrogation system of FIG. 2, with an emitter and receiver assembly being remote from the wearable respiration sensor, in accordance with an embodiment;

FIGS. 8A-C are front views of examples of different wearable respiration sensors being worn around a user's torso, in accordance with some embodiments;

FIGS. 9A-B are graphs showing a strength of a return signal transmitted by a dipole antenna of the wearable respiration sensor of FIG. 8A when worn by a woman on the left and by a man on the right;

FIG. 12 are side views of a wearable respiration sensor at different stages during manufacture, in accordance with an embodiment;

FIG. 16A is a schematic view of a user's torso wearing the wearable respiration sensor of FIG. 13, showing a transverse plane of the user;

FIG. 16B is a schematic view of a respiration monitoring system incorporating the wearable respiration sensor of FIG. 13, showing the stretching of the dipole antenna during respiration;

FIG. 16C is a sectional view of the user's torso taken along the transverse plane of FIG. 16A, showing the change of the air volume in the lungs during respiration;

FIG. 18 is a graph showing resonance frequency of the dipole antenna of the wearable respiration sensor of FIG. 13 as function of the induced stretch with and without a body phantom nearby the dipole antenna;

FIG. 20 is a graph showing the resonance frequency of the dipole antenna of the wearable respiration of FIG. 13 as function of time during breathing, showing respiration data associated to an adult male in a standing position;

FIG. 21A is a graph showing the resonance frequency of the dipole antenna of the wearable respiration of FIG. 13 as function of time during breathing, showing respiration data associated to an adult male in a sitting position;

FIG. 21B is another graph showing the resonance frequency of the dipole antenna of the wearable respiration of FIG. 13 as function of time during breathing, showing respiration data associated to an adult male in a standing position;

FIG. 21C is a graph showing the resonance frequency of the dipole antenna of the wearable respiration of FIG. 13 as function of time during breathing, showing respiration data associated to an adult male in a lying position;

FIG. 21D is a graph showing the resonance frequency of the dipole antenna of the wearable respiration of FIG. 13 as function of time during breathing, showing respiration data associated to two adult males which are superposed to one another;

FIG. 22A is a front view of another example of a wearable respiration sensor which is positioned on a chest of a simulated human body, in accordance with another;

FIG. 22B is a side view of the simulated human body of FIG. 22A, showing the wearable respiration sensor following the movements of the chest, inducing a deformation to a dipole antenna of the wearable respiration sensor of FIG. 22A during respiration;

FIG. 22C is a schematic view of an emitter being connected to the dipole antenna of the wearable respiration sensor of FIG. 22A;

FIG. 22D is a graph showing an example of respiration data as determined by a computer which is communicatively coupled to the emitter of FIG. 22C;

FIG. 23 is an image of the wearable respiration sensor of FIG. 22C, made from a polyimide-coated hollow-core silica fiber dipole antenna connected to a Bluetooth transmitter and integrated into a stretchable T-shirt, in accordance with an embodiment;

FIGS. 26A-D include graphs showing resonance frequency as function of stretching for the dipole antenna of FIG. 23, upon stretching, compressing, bending, and folding, respectively, using a simulation software;

FIGS. 31A-E include graphs showing respiration data obtained using the wearable respiration sensor of FIG. 23 for slow respiration, shallow respiration, irregular respiration, fast respiration, and a combination of no and deep long respirations, respectively;

FIGS. 32A-D include graphs showing an amplitude of fast Fourier Transform on the respiration data of FIGS. 31A-D, respectively;

DETAILED DESCRIPTION

Figure 6:
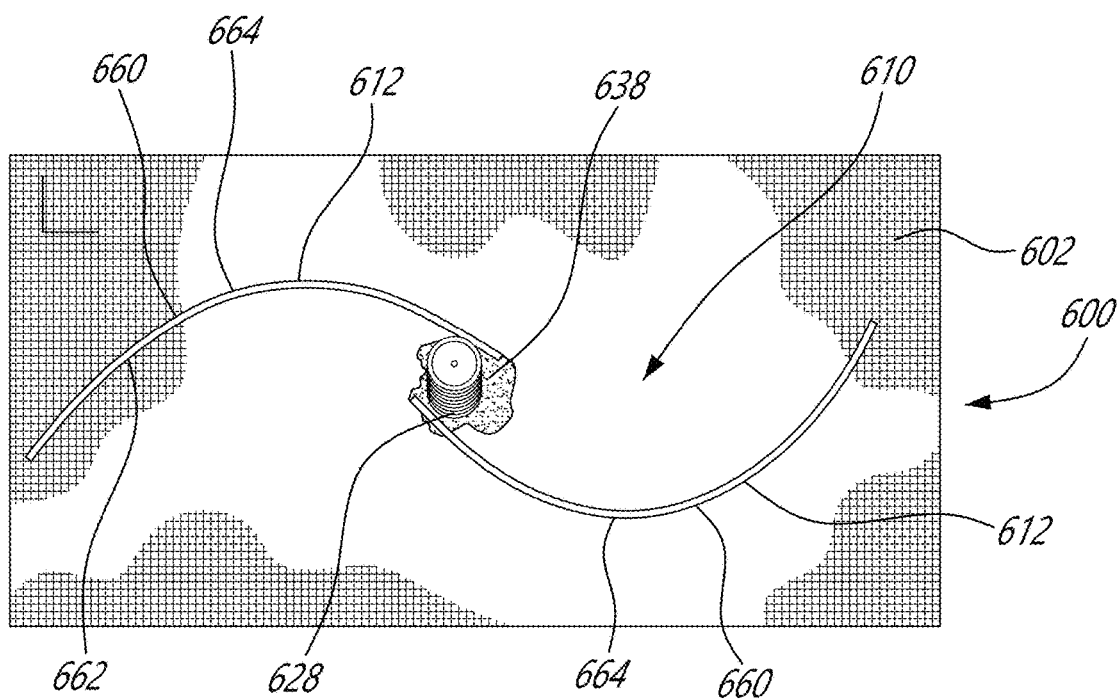
FIG. 6 is a front view of another example of a wearable respiration sensor, with a dipole antenna being glued to a stretchable substrate, in accordance with an embodiment.

FIG. 1 shows an example of a wearable respiration sensor 100, in accordance with an embodiment.

As depicted, the wearable respiration sensor 100 has a stretchable substrate 102 configured to be worn around a user's torso 104. The stretchable substrate 102 can be a textile, for instance, or an elastomeric material. The stretchability of the stretchable substrate 102 allows it to be stretched from a relaxed state to a stretched state when the stretchable substrate 102 is stretched by forces acting in opposition to each other, and back towards the relaxed state when the stretching is released. Examples of flexible stretchable textile 102 can include, but are not limited to, knits, wool, spandex, spandex blends, polyesters and the like.

In this specific embodiment, the stretchable substrate 102 is part of a garment 106 and more specifically as part of a t-shirt 108. However, in alternate embodiments, the stretchable substrate 102 can be provided in the form of any other garment such as a shirt, a women's or men's sports bra, a torso band and any other substrate which can be worn around the user's torso 104 and which is stretchable.

As illustrated, the wearable respiration sensor 100 has a dipole antenna 110 which is secured to the stretchable substrate 102. More specifically, the dipole antenna 110 has two flexible conductive elements 112 which extend in opposite directions from a center 114, relative to a dipole axis 116.

Each one of the two flexible conductive elements 112 has a proximate end 118 near the center 114, a distal end 120 away from the center 114, and a curved portion 122 curving away from and back towards the dipole axis 116 between the proximate end 118 and the distal end 120, in a plane 124 of the stretchable substrate 102. The plane 124 of the stretchable substrate 102 is meant to be interpreted broadly so as to encompass situations where the plane 124 is not always perfectly planar. For instance, the plane 124 of the stretchable substrate 102 can follow natural folds or curves that the stretchable substrate 102 may have during normal wearing conditions.

As depicted, the two flexible conductive elements 112 are in a point reflection symmetry relative to one another relative to the center 114. In other words, one of the flexible conductive elements 112 stems from a rotation of about 180° about the center 114 of the other one of the two flexible conductive elements 112, or vice versa. However, as will be understood, such point reflection symmetry described herein is meant to be interpreted broadly so as to encompass embodiments where the point reflection symmetry is not perfect.

As such, because the dipole antenna 110 is secured to the stretchable substrate 102, when the stretchable substrate 102 is stretched along the dipole axis 116, the dipole antenna 110 is also stretched in a manner that the curved portions 122 of the two flexible conductive elements 112 are flattened and the distal ends 120 are moved away from one another. Still referring to FIG. 1, dashed line 126 shows the exemplary flattening of the curved portions 122 of the two flexible conductive elements 122 and the exemplary movement of the distal ends 120 away from one another.

As can be understood, when the wearable respiration sensor 100 is worn around the user's torso 104, the dipole antenna 110 will be stretched and relaxed in a back and forth sequence between the stretched state and the relaxed state during respiration of the user. More specifically, the dipole antenna 110 is stretched from the relaxed state to the stretched state during an inspiration of the user whereas the dipole antenna 110 is relaxed back to the relaxed state during an expiration of the user.

As shown in this specific example, the wearable respiration sensor 110 has a receiving port 128 which is electrically connected to the two flexible conductive elements 112. In this specific example, the receiving port 128 is connected to the two flexible conductive elements 112 at their corresponding proximate ends 118, near the center 114. However, the receiving port 128 may be electrically connected away from the proximate ends 118 of the flexible conductive elements 112 in some other embodiments.

Depending on the embodiment, the receiving port 128 can be provided in the form of an exposed portion of the flexible conductive elements 112 to which at least an emitter can be electrically connected. Alternately, the receiving port 128 can be provided as electrical connector, such as a subminiature version A (SMA) connector and the like, to which a wire leading to at least an emitter can be connected.

As will be described in detail below, the flattening of the curved portions 122 of the two flexible conductive elements 112, the increasing of the distance d' between the distal ends 120 of the two flexible conductive elements 112, and/or the differing electromagnetic properties of the user's torso 104 during inspiration or during expiration can contribute to altering the way the dipole antenna 110 works, and thus allow the wearable respiration sensor 100 to monitor the respiration of the user wearing the wearable respiration sensor 100 around her/his torso 104.

FIG. 2 shows an example of a respiration monitoring system 130. As illustrated, the respiration monitoring system 130 has the wearable respiration sensor 100, an interrogation system 132 and a controller 134. The respiration monitoring system 130 is described with reference to the elements of FIG. 1 for ease of reading.

Broadly described, the interrogation system 132 is configured and adapted to interrogate the dipole antenna 110 of the wearable respiration sensor 100 worn around the user's torso 104, and the controller 134 is communicatively coupled to the interrogation system 132 so as to determine respiration data 136 based on said interrogation.

Typically, the interrogation system 132 has an emitter 138 configured to emit a signal 140 for transmission by the dipole antenna 110 via the receiving port 128, and a receiver 142 configured to, in response to said transmission, receive a return signal 144 varying as function of the stretching of the dipole antenna 110 of the wearable respiration sensor 100.

As will be described below, the signal 140 transmitted by the dipole antenna 110 is a radio frequency (RF) signal in this embodiment and can range from about 20 kHz to about 300 GHz. However, it was found convenient to design the dipole antenna 110 such as to transmit a signal 140 which lies in the industrial, scientific and medical (ISM) radio bands, and more specifically at 2.4 GHz.

Examples of interrogation systems are described below with reference to FIGS. 3, 4 and 5.

Still referring to FIG. 2, as discussed above, stretching of the dipole antenna 110 can alter the way the dipole antenna 110 works. Accordingly, the return signal 144 as received by the receiver 142 can vary as function of the stretching of the dipole antenna 110 during respiration of the user wearing the wearable respiration sensor 100. Data 146 concerning the return signal 144 can then be communicated to the controller 134, which can be used to determine the respiration data 136 (e.g., a respiration rate) based on the received data 146.

For instance, in some embodiments, the receiver 142 is configured to measure a resonance frequency value based on the return signal 144, where the resonance frequency value is indicative of a resonance frequency of the dipole antenna 110. In this embodiment, the data 146 received by the controller 134 can include the resonance frequency value and be used as a basis for determining the respiration data 136.

In some other embodiments, the receiver 142 is configured to measure a resonance frequency variation based on the return signal 144, where the resonance frequency variation is indicative of a variation of a resonance frequency of the dipole antenna 110 as the stretchable substrate 102 is stretched during respiration of the user wearing the wearable respiration sensor 100. In this case, the data 146 received by the controller 134 can include the resonance frequency variation and be used as a basis for determining the respiration data 136.

It is noted that in these latter embodiments, matching the impedance of the dipole antenna 110 to that of the emitter 138 may be useful to make the dipole antenna 110 resonant. To do so, a loading coil 148 or the like may be used to cancel the capacitive reactance of the dipole antenna 110. In most embodiments, the loading coil 148 is used to set the impedance of the dipole antenna 110 to 50 Ohms so as to be compatible with standard electronic components including the emitter 138 and, in some cases, the receiver 142.

In alternate embodiments, the receiver 142 is configured to measure a strength of the return signal 144 as the stretchable substrate 102 is stretched during respiration of the user wearing the wearable respiration sensor 100. In these embodiments, the data 146 received by the controller 134 can include the strength of the return signal 144 and be used as a basis for determining the respiration data 136.

As will be understood, the return signal 144 can be measured so as to monitor other fundamental properties of the dipole antenna 110 such as gain, radiation pattern, impedance, bandwidth and polarization from which the respiration data 136 may be determined.

It is noted that the controller 134 can be provided as a combination of hardware and software components. The hardware components can be implemented in the form of a computing device. Moreover, the software components of the controller can be implemented in the form of a software application.

More specifically, the computing device can have a processor, a memory, and I/O interface. Instructions for determining respiration data such as a respiration rate can be stored on the memory and accessible by the processor.

The processor can be, for example, a general-purpose microprocessor or microcontroller, a digital signal processing (DSP) processor, an integrated circuit, a field programmable gate array (FPGA), a reconfigurable processor, a programmable read-only memory (PROM), or any combination thereof.

The memory can include a suitable combination of any type of computer-readable memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface enables the computing device to interconnect with one or more input devices, such as the interrogation system 132, or with one or more output devices such as a user interface (not shown).

Each I/O interface enables the controller 134 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g. WMAX), SS7 signaling network, fixed line, local area network, wide area network, and others, including any combination of these.

FIG. 3A shows an example of an interrogation system 232A which is configured to interrogate the wearable respiration sensor 100 of FIG. 1, in accordance with an embodiment. As shown in this example, the interrogation system 232A includes an emitter 238 configured to emit a signal 240 for transmission by the dipole antenna 110. More specifically, the emitter 238 is made integral to the wearable respiration sensor 100 such that the emitter 238 is directly connected to the receiving port 128. In this way, the emitter 238 can emit a signal 240 to be transmitted in a surrounding environment 250 by the dipole antenna 110.

In this specific embodiment, the emitter 238 is a Bluetooth® emitter serial number nRF51822 (Nordics Semiconductor). However, any other suitable type of wireless emitter can be used in other embodiments.

As shown, a receiver 242 of the interrogation system 232A is configured to, in response to said transmission, receive a return signal 244 resulting from the transmission of the signal 240 by the dipole antenna 110. In this particular example, the receiver 242 is remote from the wearable respiration sensor 100. In other words, the receiver 242 is not made integral to the wearable respiration sensor 100 in this example. For instance, in some embodiments, the receiver 242 can be connected to, or be part of, a laptop computer, a smart phone, an electronic table or a smart watch. Advantageously, the respiration of the user wearing the wearable respiration sensor 100 can thus be remotely monitored.

In this embodiment, the receiver 242 is communicatively coupled to the wearable respiration sensor 100 via a wireless connection, which allows the receiver 242 to be distant from the wearable respiration sensor 100. However, in some other embodiments, the receiver 242 may be made integral to the wearable respiration sensor 100 also.

FIG. 3B shows an example of an interrogation system 232B which is configured to interrogate the wearable respiration sensor 100 of FIG. 1, in accordance with an embodiment. As shown in this example, the interrogation system 232B includes an emitter 238 configured to emit a signal 240 for reception by the dipole antenna 110. More specifically, in this example, the emitter 238 is remote from the wearable respiration sensor 238. For instance, the emitter 238 can be connected to, or be part of, an external electronic device such as a smart phone, an electronic tablet, a smart watch and the like. In this way, the emitter 238 can emit a signal 240 to be transmitted in a surrounding environment 250 and then received by the dipole antenna 110.

Still in this specific embodiment, the emitter 238 is a Bluetooth® emitter serial number nRF51822 (Nordics Semiconductor). However, any other suitable type of wireless emitter can be used in other embodiments.

As shown, a receiver 242 of the interrogation system 232B is configured to, in response to said reception, receive a return signal 244 resulting from the reception of the signal 240 by the dipole antenna 110. In this particular example, the receiver 242 is directly connected to the receiving port 128. In other words, the receiver 242 is made integral to the wearable respiration sensor 100 in this example. Advantageously, the respiration of the user wearing the wearable respiration sensor 100 can thus be remotely monitored.

In this embodiment, the emitter 238 is communicatively coupled to the wearable respiration sensor 100 via a wireless connection, which allows the emitter 238 to be distant from the wearable respiration sensor 100. However, in some other embodiments, both the emitter 238 and the receiver 242 may be made integral to the wearable respiration sensor 100 also.

As can be understood, in this example, the receiver 242 can be wiredly and/or wirelessly connected to the controller 134 so as to receive the data 146 concerning the return signal 146. For instance, in some embodiments, the controller 134 can be made integral to the wearable respiration sensor 100. In alternate embodiments, the controller 134 can be remote from the wearable respiration sensor 100 and from the receiver 242.

FIG. 4 shows a block diagram of an example respiration monitoring system 332, in accordance with an embodiment. As shown, the respiration monitoring system 332 has the wearable respiration sensor 110, a wireless emitter 338 (e.g., Bluetooth, Zigbee, XBee, Wi-Fi, RFID), and an impedance matching circuit 348 connecting the wireless emitter 338 to the dipole antenna of the wearable respiration sensor 100. The respiration monitoring system 332 includes circuit accessories such as oscillators, GPS, and a manual or automated control to turn on or off the emitter. Hardware user interface allowing programming, monitoring, controlling and communicating can also be provided. The controller includes a field-programmable gate array (FPGA), power management, manual or automated control to turn on or off the power management, and a portable and/or rechargeable power source.

FIG. 5 shows another example of an interrogation system 432 to interrogate the wearable respiration sensor 100, in accordance with an embodiment. As shown in this example, the interrogation system 432 includes an emitter 438 configured to emit a signal 440 for transmission by the dipole antenna 110. More specifically, the emitter 438 is remote from the wearable respiration sensor 100 such that the emitter 438 is remotely connected to the receiving port 128 via a conductive wire 452. As shown, the receiving port 128 is provided in the form of a female connector 454 which is configured and adapted to receive a corresponding male connector 456 of the conductive wire 452. In this embodiment, the emitter 438 can emit a signal to be communicated to the dipole antenna 110 for transmission thereof in the surrounding environment 250.

Again in this example, the receiver 442 is remote from the wearable respiration sensor 100, and is remotely connected to the receiving port 128 via the same conductive wire 452 to receive the return signal. As shown, the emitter 438 and the receiver 442 can be provided in the form of an emitter and receiver assembly 458 such as a vector network analyzer, for instance.

Referring back to FIG. 2, it is intended that the controller 134 and the interrogation system 132 can be made integral to the stretchable substrate 102 in some alternate embodiments. In these embodiments, the respiration data 136 determined by the controller 134 can be stored on a portable memory medium (e.g., a memory stick or micro SD card), transmitted wirelessly for storing on a remote memory via a network such as the Internet, and/or stored on a memory of the controller 134.

Figure 6A:
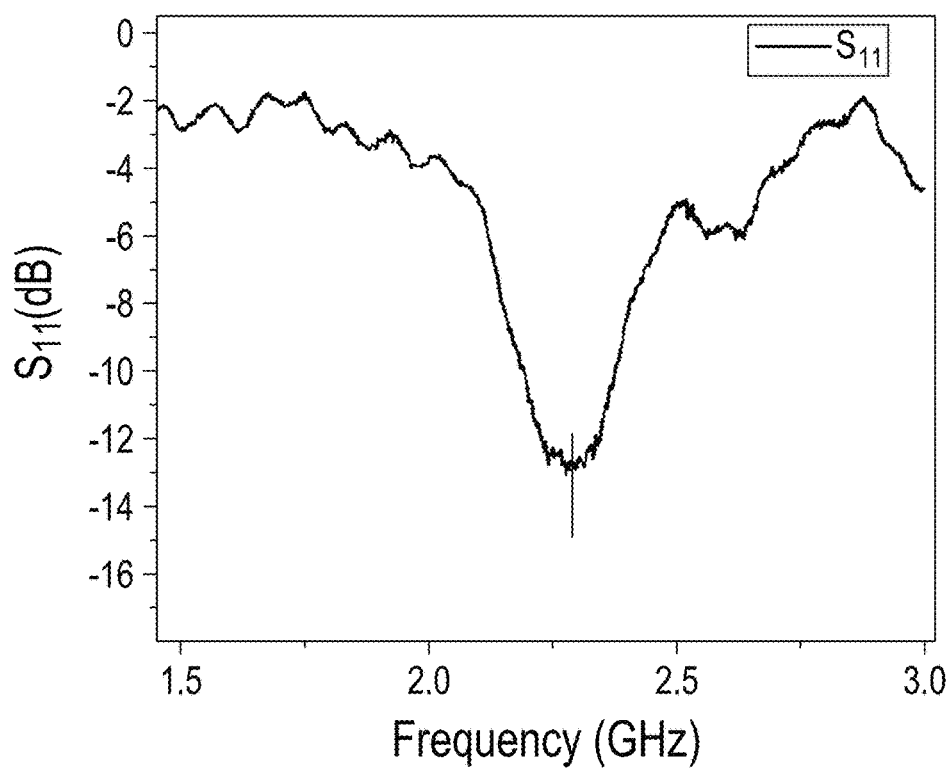
FIG. 6A is a graph showing a spectral response of the dipole antenna of FIG. 6, in accordance with an embodiment.

FIG. 6 shows an example of a wearable respiration sensor 600 whereas FIG. 6A shows a return loss $S_{11}$ of the dipole antenna 610 as function of frequency, showing a resonance frequency value associated to the dipole antenna 610.

In this specific embodiment, the dipole antenna 610 of the wearable respiration sensor 600 has two flexible conductive elements 612 similar to the ones of FIG. 1. An emitter 638 is directly connected to a receiving port 628 of the wearable respiration sensor 600. In this specific embodiment, the two flexible conductive elements 612 are hollow capillary fibers 660 made of polymer and having inner cavities coated with a conductive layer of silver. Accordingly, the layers of silver act as the conductor for transmitting the signal.

The dipole antenna 610 can be secured in many ways to the stretchable substrate 602. For instance, in this specific embodiment, the two flexible conductive elements 612 are secured to the stretchable substrate 602 using glue 662. Accordingly, the dipole antenna 610 is glued to the stretchable substrate 602. As can be understood, the glue 662 used to secure the dipole antenna 610 is chosen so as to be somewhat flexible, so as to allow the dipole antenna 610 to be satisfactorily stretched from the relaxed state to the stretched state during respiration of the user wearing the wearable respiration sensor 600.

In this embodiment, a polymer coating 664 has been provided to the dipole antenna. In this way, the polymer coating 664 can protect the dipole antenna 610 and/or the emitter 638, and the two corresponding flexible conductive elements 612, from humidity (e.g., sweat) that can surround or be generated by the user wearing the wearable respiration sensor 600. More specifically, the polymer coating 664 can include a superhydrophobic coating so as to repulse as much as possible humidity.

The flexible conductive elements 612 of this embodiment are made of the hollow core polymer capillaries in which silver layers were deposited. The silver thickness was measured to be 200±30 nm, and the electric resistance of the flexible conductive elements was measured to be 3.5±1 Ω/cm. These hollow-core polymer capillaries have an inner diameter of about 200 μm and an outer diameter of about 362 μm and they were fabricated in-house using a 12-meter drawing tour using polyethylene terephthalate glycol-modified (PETG) polymer tubing (available commercially).

Although PETG polymer has been used in this embodiment, it is noted that other polymers could as well have been used. Examples of such polymers can include, but not limited to, poly(methyl methacrylate) (PMMA) and/or polyimide materials. Such dipole antenna 610 based on polymer hollow-core fiber can be protected from any external perturbation such as moisture.

Figure 7:
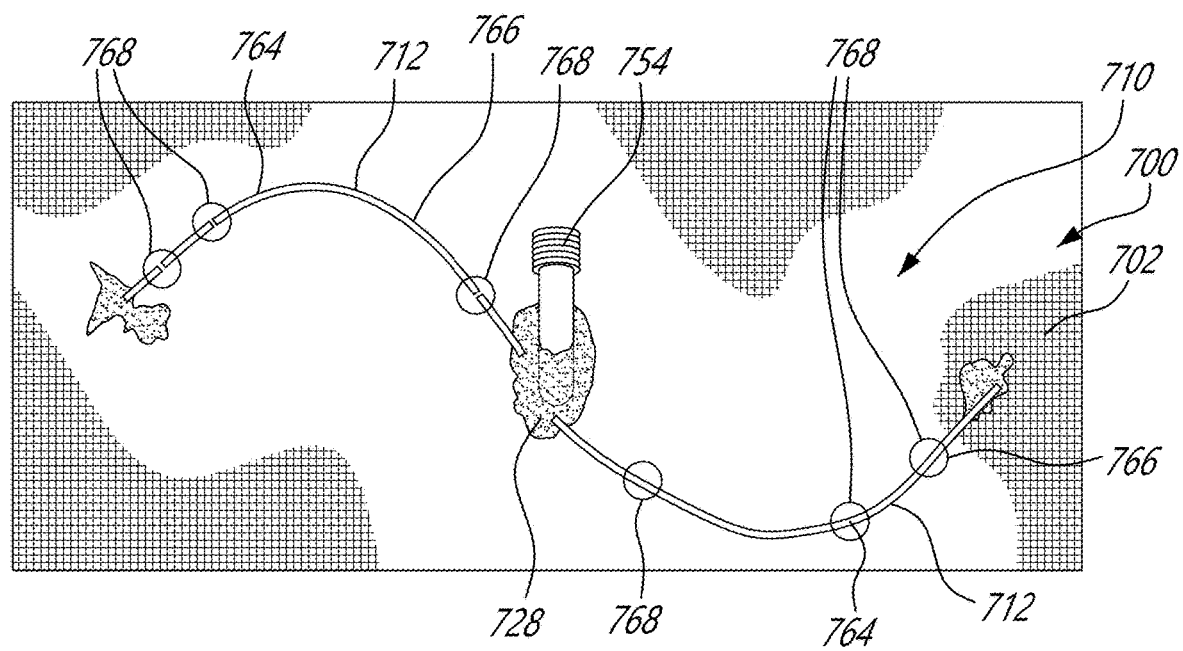
FIG. 7 is a front view of another example of a wearable respiration sensor, with a dipole antenna being stitched to a stretchable substrate, in accordance with an embodiment.
Figure 7A:
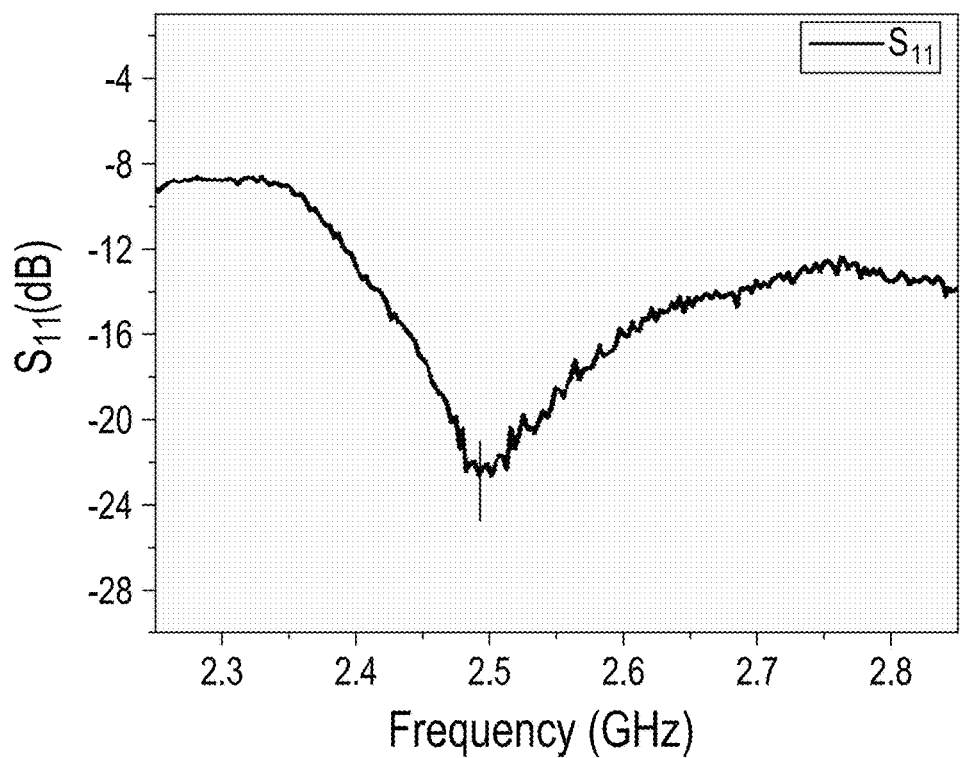
FIG. 7A is a graph showing a spectral response of the dipole antenna of FIG. 7, in accordance with an embodiment.

FIG. 7 shows another example of a wearable respiration sensor 700 whereas FIG. 7A shows a return loss $S_{11}$ of the dipole antenna 710 as function of frequency, showing a resonance frequency value associated to the dipole antenna 710.

In this specific embodiment, the dipole antenna 710 of the wearable respiration sensor 700 has two flexible conductive elements 712 similar to the ones of FIG. 1. An electrical connector 754 such as a SMA female connector is directly connected to a receiving port 728 of the wearable respiration sensor 700.

As shown, the two flexible conductive elements 712 are provided in the form of conductive yarns 766. More specifically, the conductive yarns 766 are made of stainless steel in this example. An example of such stainless steel yarns includes ADA306. The electrical resistance of these yarns has been measured at 1.3±0.1 Ω/cm.

Although the stainless steel conductive yarns have been used in this embodiment, any other suitable conductive yarn could as well have been used. For instance, examples of such conductive yarns can include, but not limited to, carbon conductive yarn, silver conductive yarn and the like. It can be convenient to use conductive yarn for the following reasons. First, the step of depositing conductive material onto a fiber can be omitted as the conductive yarns are de facto conductive. Also, such conductive yarns can be integrated into the stretchable substrate 702 more easily using classical industrial weaving process. The downside of using a pure conductive yarn could be its vulnerability to moisture. Thanks to recent developments in material science, the conductive yarns 766 can be made moisture-resistant by using a hydrophobic spray, or by covering the conductive yarn 766 with a hydrophobic polymer 764 using deep coating technique, depending on the embodiment.

In the illustrated embodiment, the two flexible conductive elements 712 are secured to the stretchable substrate 702 using stitches 768. Accordingly, the dipole antenna 710 is stitched to the stretchable substrate 702. As can be understood, the stiches 768 used to secure the dipole antenna 710 is sufficiently spaced-apart from one another so as to allow the dipole antenna 710 to be satisfactorily stretched from the relaxed state to the stretched state during respiration of the user wearing the wearable respiration sensor 700.

In some other embodiments, the flexible conductive elements 712 can be secured to the stretchable substrate 702 by weaving the flexible conductive elements 712 directly into the stretchable substrate 702.

The position and the orientation of the wearable respiration sensor relative to the user's torso when the wearable respiration sensor can differ from one embodiment to one another. For instance, FIGS. 8A-8C show three different embodiments.

FIG. 8A shows an example of a wearable respiration sensor 800A, in accordance with an embodiment. As shown, the stretchable substrate 802A is provided in the form of a t-shirt.

In this example, when the wearable respiration sensor 800A is worn around a user's torso 804, the dipole axis 816A of the dipole antenna 810A is disposed parallel to a transverse plane 870 of the user's torso 804 while the center 814A of the dipole antenna 810A is aligned with a sagittal plane 872 of the user's torso 804.

Moreover, the dipole antenna 810A is disposed at a specific location of the t-shirt so that the dipole antenna 810A is close to a user's chest, and lungs, when the wearable respiration sensor 800A is worn around the user's torso 804.

FIG. 8B shows another example of a wearable respiration sensor 800B, in accordance with an embodiment. As shown in this example, the stretchable substrate 802B is provided in the form of a shirt. Accordingly, in contrast with the embodiment of FIG. 8A, the center 814 of the dipole antenna 810B is spaced from the sagittal plane 872 of the user's torso 804.

Further, the dipole antenna 810B is disposed at a specific location of the shirt so that the dipole antenna 810B is close to a user's belly when the wearable respiration sensor 800B is worn around the user's torso 804 in this example.

FIG. 8C shows another example of a wearable respiration sensor 800C, in accordance with an embodiment. As depicted, the stretchable substrate 802C is provided in the form of a torso band. In contrast with the embodiments of FIGS. 8A and 8B, the dipole axis 816 of the wearable respiration sensor 800C extends parallel to the sagittal plane 872 of the user's torso 804 when the wearable respiration sensor 800C is worn around the user's torso 804. Additionally, the center 814 of the dipole antenna 810 is aligned with the sagittal plane 872 in this example.

It was found that sports type respiration can be best detected with the wearable respiration sensor being a bit higher, such as shown in FIG. 8A, and stomach type respiration can be best detected with the wearable respiration sensor a bit lower, such as shown in FIGS. 8B and 8C. Apparently, in some embodiments, the wearable respiration sensor can work better when it is positioned horizontally and around the center of the user's torso, or on the front of the user.

FIGS. 9A-B are graphs showing a strength of a return signal transmitted by a dipole antenna of the wearable respiration sensor 800A of FIG. 8A when worn by a woman on the left and by a man on the right. Respiration rates can be determined from these two graphs by the controller.

Figures 10A, 10B:
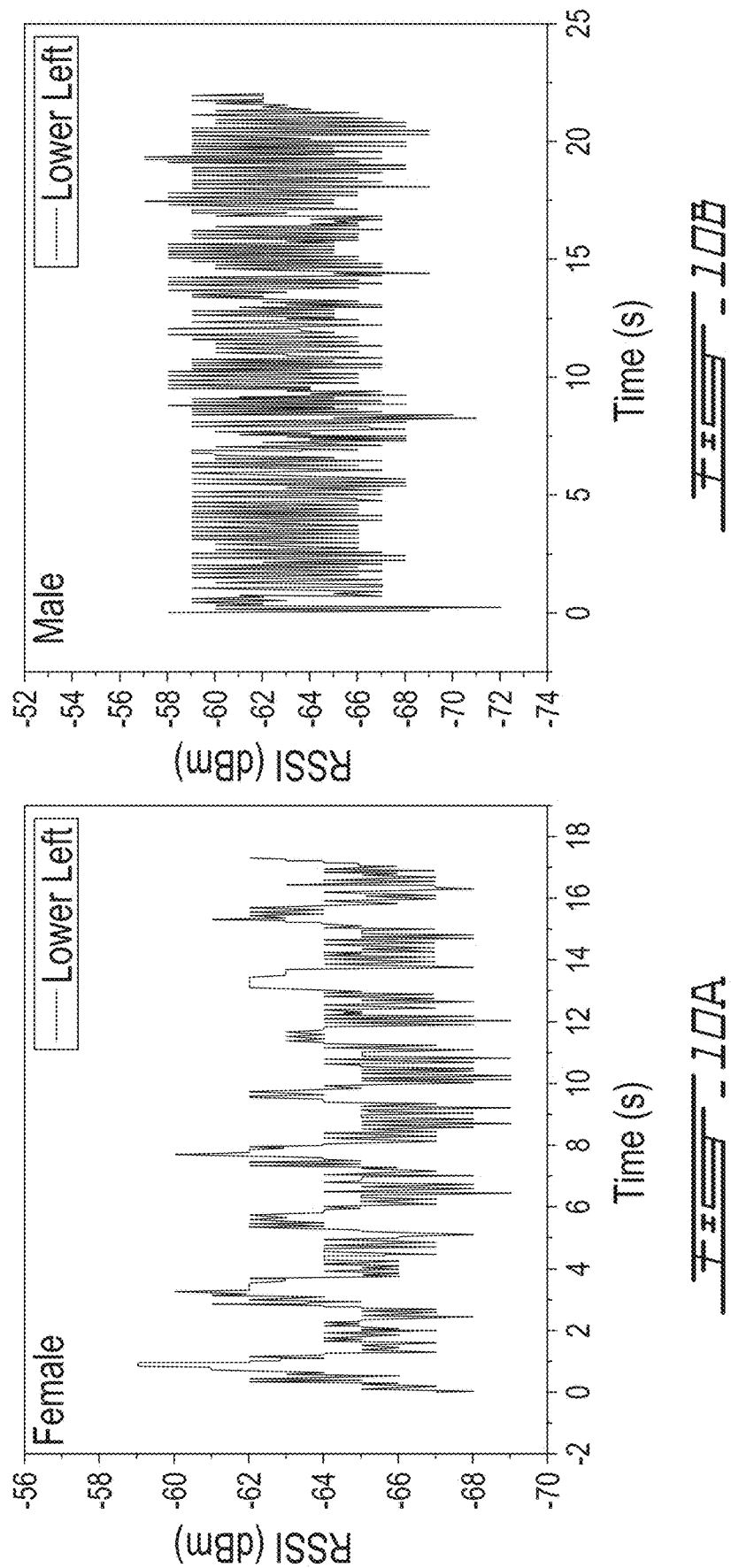
FIGS. 10A-B are graphs showing a strength of a return signal transmitted by a dipole antenna of the wearable respiration sensor of FIG. 8B when worn by a woman on the left and by a man on the right.

FIGS. 10A-B are graphs showing a strength of a return signal transmitted by a dipole antenna of the wearable respiration sensor 800B of FIG. 8B when worn by a woman on the left and by a man on the right. Respiration rate can be determined from the lefthand side one of the graphs whereas it is not possible for the righthand side one of the graphs. This can mean that this individual has no belly breath, i.e. he may be an athlete.

Figures 11A, 11B:
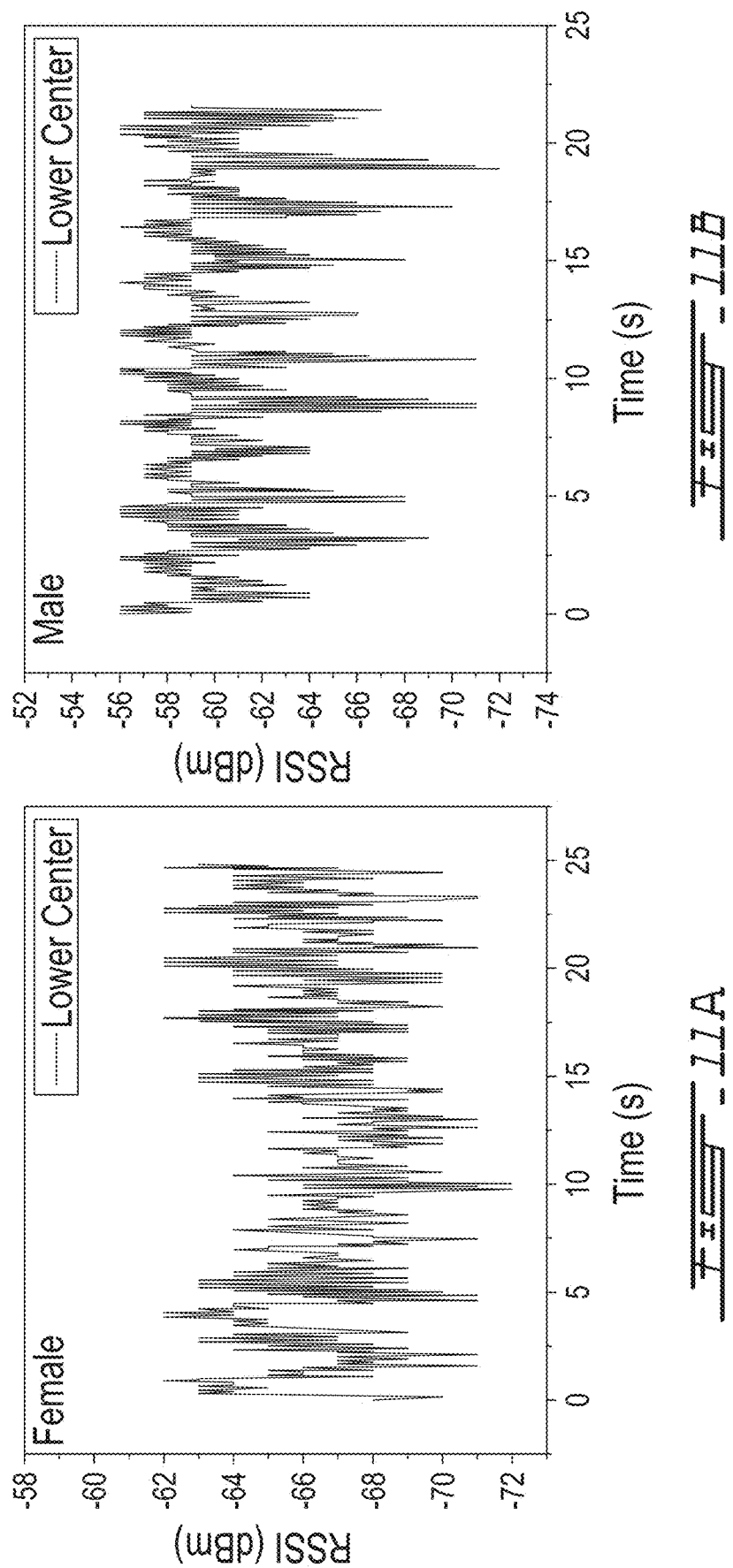
FIGS. 11A-B are graphs showing a strength of a return signal transmitted by a dipole antenna of the wearable respiration sensor of FIG. 8C when worn by a woman on the left and by a man on the right.

FIGS. 11A-B are graphs showing a strength of a return signal transmitted by a dipole antenna of the wearable respiration sensor 800C of FIG. 8C when worn by a woman on the left and by a man on the right.

FIG. 12 shows steps of a method 1200 of manufacturing an example of a wearable respiration sensor as a succession of manufacturing steps. A first step 1202 includes providing a stretchable substrate 1202, to which a thermoplastic polyurethane (TPU) film 1274 is adhered via heating using a steam iron. A second step 1204 includes adhering a flexible printed circuit board 1276 having an emitter 1238 (and optionally other electronic components) to the TPU film 1274. In this example, the position of the emitter 1238 defines a center 1214 of a dipole antenna 1210 which will be manufactured in subsequent steps. As such, a third step 1206 includes sewing a first flexible conductive element 1212a to the stretchable substrate 1202 on one side of the center 1214, and sewing a second flexible conductive element 1212b to the stretchable substrate 1202 on an opposite side of the center 1214. In this example, the first and second flexible conductive elements 1212a and 1212b are sewn through zigzag stitches 1278. A fourth step 1208 includes sewing conductive wires 1280 to the stretchable substrate 1202 in order to connect the flexible PCB 1276 and the two flexible conductive elements 1212a and 1212b to one another using straight stitches 1282. A fifth step 1210 of applying superhydrophobic polymer films 1284 over the two flexible conductive elements 1212a and 1212b and over the conductive wires 1280. In this example the superhydrophobic polymer films 1284 are applied using a press transfer molding machine. A sixth step 1212 includes encapsulating the emitter 1238 using a layer of polymer 1286 such as a layer of PDMS covering the gap between the superhydrophobic films 1284.

It was found that using the superhydrophobic layers (defined by a water contact angle of about 152° and a sliding angle of about 6°) can allow uninterrupted wireless communication of the wearable respiration sensor even when it is under direct water in some situations. Such superhydrophobic layers can be advantageously applied on the flexible conductive elements when they are made of hollow-core capillaries or of conductive yarns. In addition or alternately, for the conductive yarns, an enhanced protection can be applied by using thin polymer film using deep coating process onto the flexible conductive elements, which can be cheap and efficient.

Example 1—Wearable Contactless Respiration Sensor Based on Multi-Material Fibers Integrated into Textile In this example, a report on a wearable respiration sensor for the contactless monitoring of the respiration rate is presented. The wearable respiration sensor is made from flexible conductive elements provided in the form of multi-material fibers arranged in a spiral antenna designed for operating at a central frequency of 2.45 GHz. In this example, high flexibility of the used composite metal-glass-polymer fibers can permit their integration into a cotton t-shirt without compromising comfort or restricting movement of the user. At the same time, change of the antenna geometry, due to the chest expansion and the displacement of the air volume in the lungs, is found to cause a certain shift of the antenna operational frequency, thus allowing respiration detection. In contrast with many existing sensors, respiration is detected without attachment of the electrodes of any kind to the user's body, neither direct contact of the fiber with the skin is required. Respiration patterns for two male volunteers were recorded with the help of a sensor prototype integrated into standard cotton t-shirt in sitting, standing, and lying scenarios. The typical measured frequency shift for the deep and shallow breathing was found to be in the range 120-200 MHz and 10-15 MHz, respectively. The same spiral fiber antenna is also shown to be suitable for short-range wireless communication, thus allowing respiration data transmission, for example, via the Bluetooth protocol, to mobile handheld devices.

It is known that monitoring vital signals and various activity types using "wearable" electronic devices has become an increasingly attractive field of research, especially in the recent years, appealing to the health and overall well-being concerns of the general public. Consequently, many solutions have surfaced over the last few years, including numerous "smart" watches and fitness trackers. Some of them are aimed at health monitoring, while others focus on recreational usage.

Numerous studies [1-3] show that routine monitoring of basic vital parameters, such as blood pressure, heart rate, body temperature, and respiration rate are extremely useful to expose various medical dysfunctions. While in the present day there are multiple solutions capable, for example, of continuous heart rate monitoring, only a very few [4,5] can also provide respiration rate information. This information, however, can be vital for prevention of many respiration disorders. One could think of asthma, pneumonia, chronic obstructive pulmonary disease (COPD), and sleep apnea, as diseases that benefit from the supervision of the breathing rate for improved diagnostics.

Modern techniques used to monitor the respiration rate include pneumography [6], which uses impedance change to monitor the chest movement with the use of electrodes attached to the body, or standard pulse oximetry [7], which allows measurement of the respiration rate through the absorption of infrared light and requires a probe to be linked to the patient's finger. The respiration rate can also be derived from the measurements given by an electrocardiogram (ECG) [8], which also requires the installation of electrodes on the patient's body. In the domain of remote biosensing, impulse radio (IR) UWB (ultra-wideband) wireless systems [9] have attracted a lot of interest. These systems rely on the transmission and reception of sub-nanosecond RF (Radio Frequency) pulses for movement detection, including patient's chest movement which, in turn, allows heartbeat and respiration rate measurements. Such systems do not require any electrodes to be attached to the patient's body. However, they can require complex measurement equipment and signal analysis and, most importantly, can restrict the patient to remain in a certain operating zone, i.e., lying in bed.

On the other hand, in the past decades textiles have become a popular platform for integration of various sensors providing active functionalities to the previously passive textiles. As such, gloves have been developed to detect hand posture [10] and gesture language recognition; pants, to monitor lower body movement [11]; and several shirts, to record ECG [12], electromyography (EMG) [13], electroencephalography (EEG) [14], and breathing rate [5]. Recently there have been attempts to adopt the above-mentioned IR UWB technology into smart textiles [15]. However, these solutions still rely on patch antenna designs, made of conductive threads or fabrics and, thus, according to antenna theory [16], require rather thick (6-7 mm) substrates. Thus, with the development of the smart textiles domain came the realization that conventional microelectronic devices do not satisfy the user-comfort requirements for many practical applications and, hence, emerged the need to develop solutions integrated into threads and fibers composing the textiles. Proposed solutions involve conductive yarn [17], optical fibers [4], conductive polymer [18] or multi-material fibers [19,20], that can be used as sensors [21], antennas [22], or circuit designs [14] incorporated into textiles to monitor various activities.

Naturally, many smart textile applications are aiming towards medical monitoring. For example, fiber Bragg grating (FBG)-based sensors [4], have been integrated into a cushion to monitor vibrations due to respiration and heart rate. While FBG sensors demonstrate very high precision and are capable of monitoring ECG and respiration rate simultaneously, their most considerable drawback is, however, similar to the IR UWB method: the necessity to use a laser source and often complicated signal reconstruction procedures. That leads to restricted mobility of the user, which can be tolerated in certain applications, for example, during MRI scanning [4].

Alternatively, a great variety of various "patch" monitors for long-term ECG measurements [23] has been already proposed. Including piezoelectric elements integrated into a shirt that can provide the breathing rate information [5], and conductive textile patches [24]. However, such solutions often still require either a control unit located somewhere on the shirt or involve the use of probes or electrodes that should be securely attached to the user's body and can cause certain discomfort. While in some cases uneasiness can be tolerated, for specific applications user comfort is the topmost priority. In particular, it was shown that around 10% of newborn infants require respiratory assistance [25], facing neonatal respiratory disorders. Monitoring the breathing rate of the newborns plays an important role toward the reduction of the interventions needed to assure their wellbeing and is challenging with many classical methods, such as the cardiopulmonary monitor to which newborns are connected via electrodes. This motivated us to focus on the non-invasive respiration monitoring without using any electrodes/probes attached to the body or bulky control units compromising comfort.

Respiration is made possible by the diaphragm and the external intercostal muscles. During inhalation, the diaphragm contracts itself and moves downward producing a pressure difference causing air to enter the lungs. The contraction of the intercostal muscles causes the ribs to elevate which results in the expansion of the chest cavity allowing a greater volume of air to enter. Typically, the tidal volume which is the volume inhaled during normal breathing is 7 mL/kg [26]. This amount of air penetrates the lungs causing an expansion of 7.37 cm [27] for men aged 25-34 taking deep breaths. The proposed solution in this example takes advantage of the both mechanisms: the physical chest expansion and the change of the air volume in the lungs.

In this example, a prototype garment designed to monitor the breathing rate of an adult is proposed. The prototype is made via the integration of the previously-reported multi-material fibers [21,22] in the form of a spiral antenna designed to radiate at 2.45 GHz. The key feature of such antenna is the central frequency shift exhibited due to the lung volume change and textile stretching under the chest movement. This can allow providing respiratory data information to a remote PC in real-time in this embodiment. The prototype dipole antenna was first characterized in terms of return loss ($S_{11}$), gain, and radiation pattern to assess its performance for the short-range wireless communications. Next, the textile prototype with an integrated antenna was submitted to stretching tests reproducing the respiration movement with and without a body phantom. Finally, on-body measurements were performed to monitor the breathing rate of the two volunteers.

Figures 13, 13A:
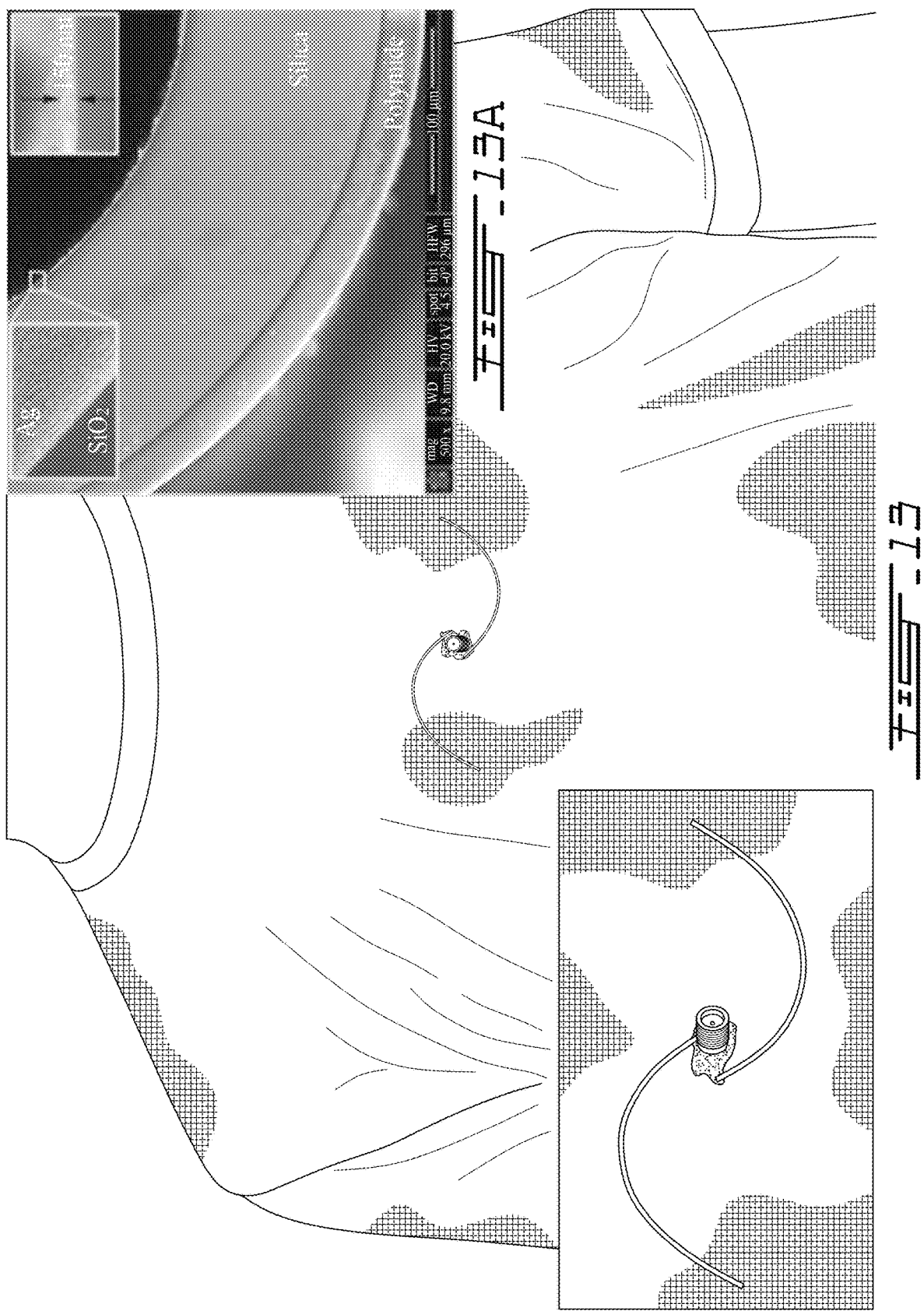
FIG. 13 is an image of an example of a wearable respiration sensor worn on a user's torso via a cotton shirt, in accordance with an embodiment.
FIG. 13A is a scanning electron microscope of a section of a flexible conductive element of a dipole antenna of the wearable respiration sensor of FIG. 14.

The spiral dipole antenna is made of multi-material fibers consisting of polyimide-coated hollow-core silica glass capillaries (commercially available from Polymicro Technologies, Phoenix, Ariz., USA) in which silver layer was deposited using the liquid state deposition technique based on the Tollen's reaction [28], as described in [21]. The inset of FIG. 13A shows the SEM images of the resulting fiber (200 µm inner and 362 µm outer diameter with an 18 µm thick polyimide layer). The inner silver coating layer has a thickness of 150±30 nm, which grants the fibers an electric resistance of 3±1 Ω/cm. The use of multi-material fibers allowed designing an antenna that follows the shape of a half-turn Archimedean spiral.

As can be seen in FIG. 13, position of the spiral elements was adjusted to allow installation of an SMA connector that was used for interrogation purposes. Electrical connections were done manually using copper wires (127 µm in diameter). The antennas were integrated into a 20 cm×10 cm cotton patch (for off-body characterization) and into a cotton t-shirt (for on-body measurements) with cyanoacrylate glue that offers reasonable flexibility. In all experiments, the resonant frequency shift was continuously measured using an interrogation system comprising a HP Agilent 8722ES network analyzer connected to a controller (e.g., a personal computer) via a general purpose interface bus (GPIB) interface. The data acquisition was done with a custom LabVIEW interface using the controller.

One of the advantages of the wearable respiration sensor is that the same fiber antenna could be used to acquire respiration data and to transmit it, for example, to external mobile devices. Thus, the antenna has been characterized in terms of its radiation performance (e.g., return loss, radiation pattern and gain) in free-space; and then studied for respiration rate detection mechanisms with the help of human body phantoms and two male volunteers.

The proposed wearable respiration sensor demonstrates hybrid RF-emissive properties between a multi-turn spiral and a dipole antenna, which can be particularly well seen from the radiation pattern measurements. Hence, the term "spiral" is used for simplicity in this example.

Figure 14:
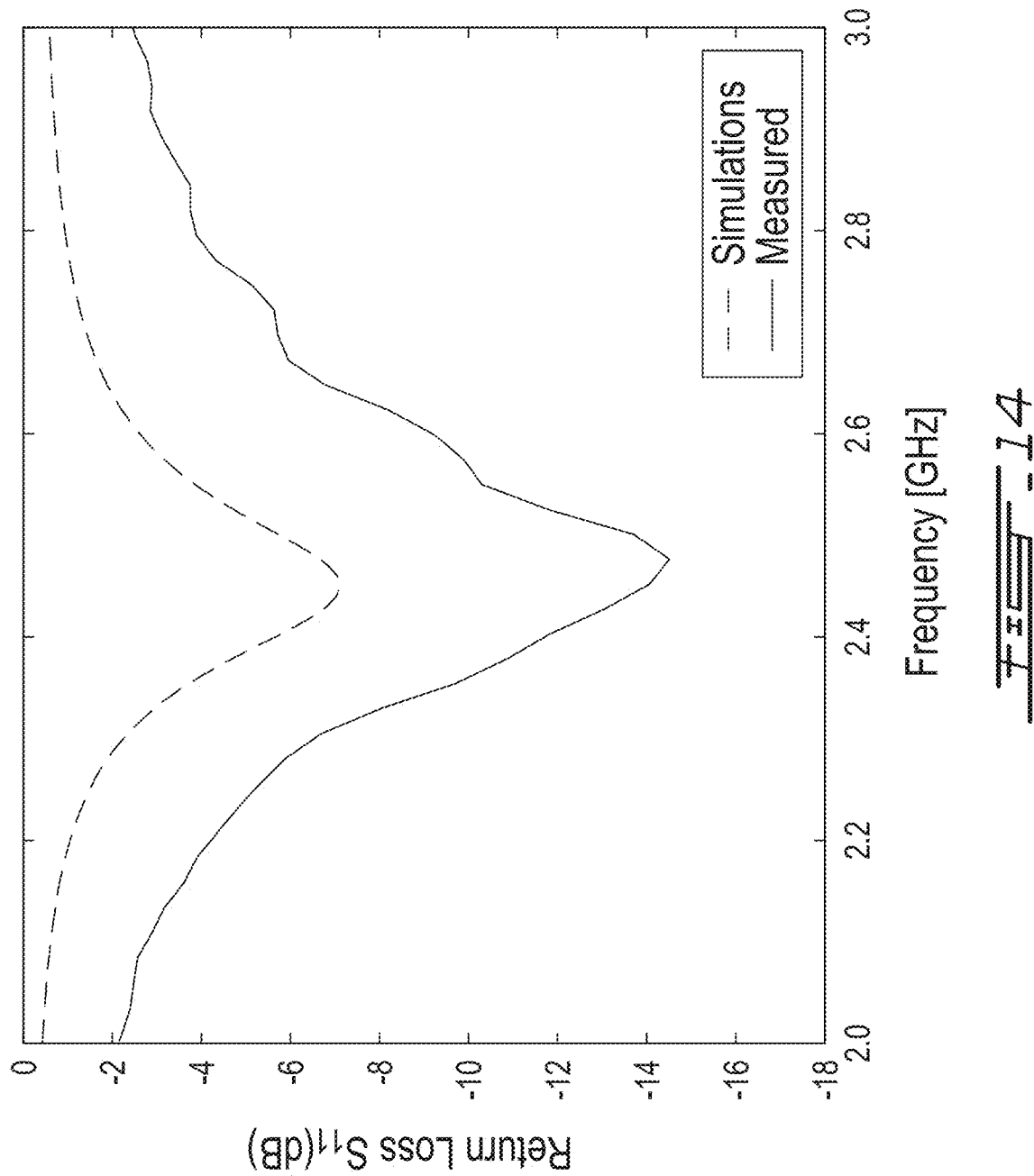
FIG. 14 is a graph showing return loss for the dipole antenna of the wearable respiration sensor of FIG. 13, with the measure return loss in solid line and the simulated return loss in dashed line.

The concept of scattering (S) parameters, representing input-output relationship between ports (or terminals) of an electrical system, is widely used [29] to characterize frequency responses of the antennas (see FIG. 14). The 2.45 GHz operating frequency belongs to the ISM (industrial, scientific, and medical) band and was chosen according to the requirements of the medical monitoring applications. Numerical simulations, shown by the dashed line in FIG. 14, were done using industry-standard ANSYS HFSS software. The difference between simulations and experimental measurements can probably be attributed to the limitations of the antenna model, since certain assumptions about the material and structure are inevitably made.

Figure 15B:
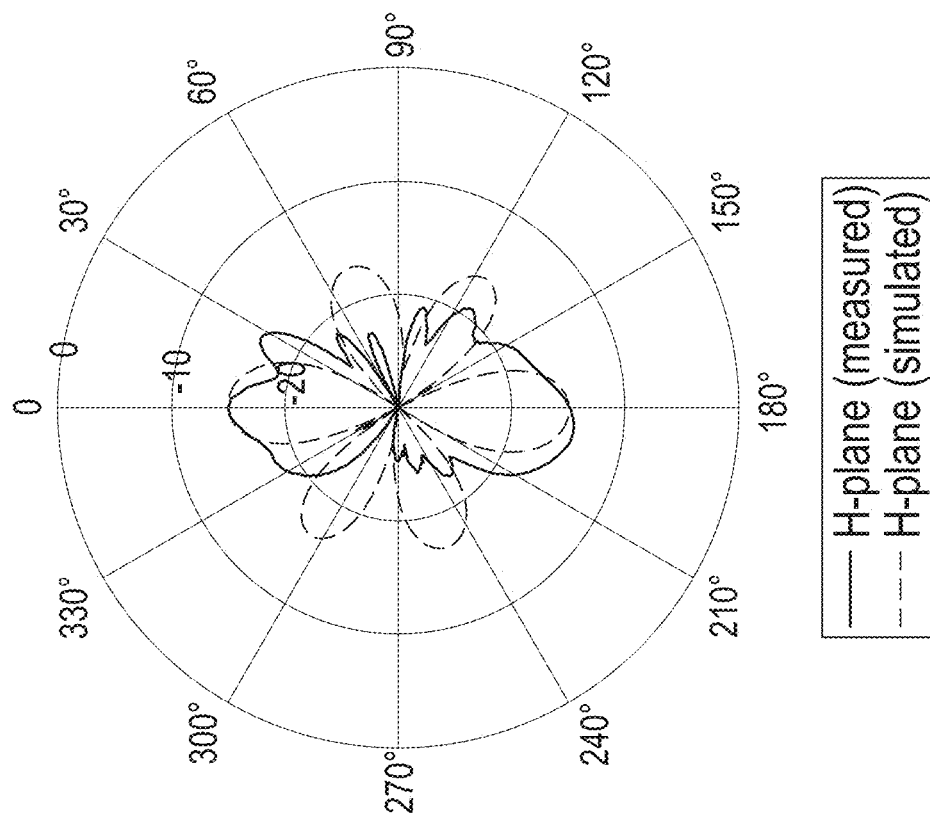
FIG. 15B is a graph showing a radiation pattern H-plane of the dipole antenna of the wearable respiration sensor of FIG. 13 operating at a frequency of 2.4 GHz, with the measured radiation pattern plane in solid line and the simulated radiation pattern plane in dashed line.
Figure 15A:
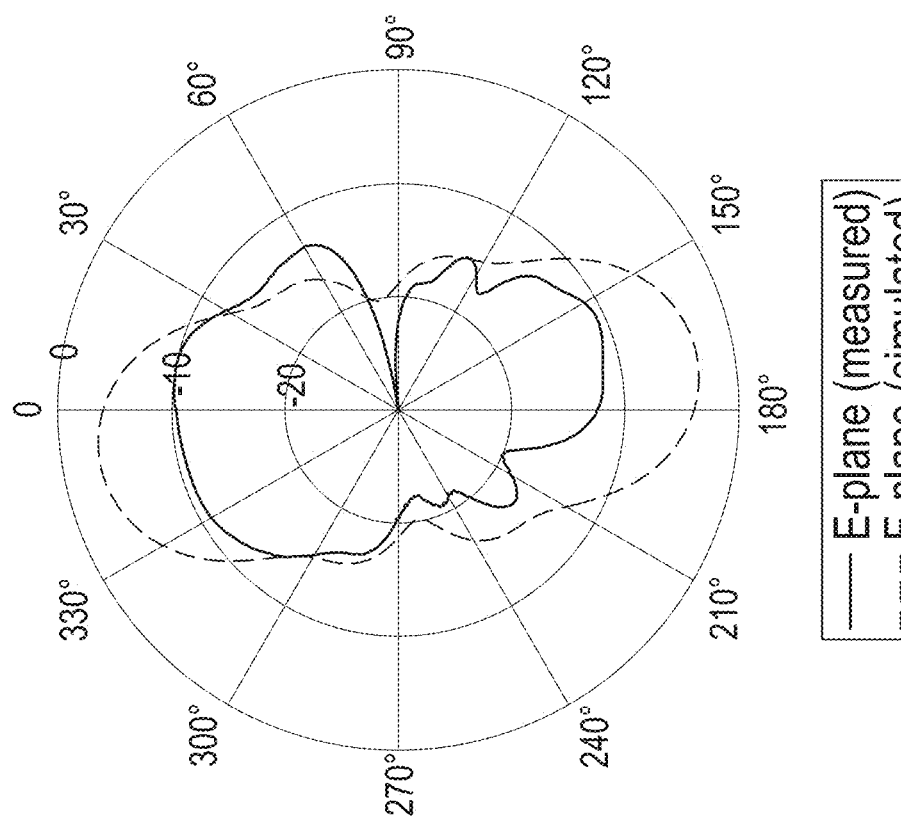
FIG. 15A is a graph showing a radiation pattern E-plane of the dipole antenna of the wearable respiration sensor of FIG. 13 operating at a frequency of 2.4 GHz, with the measured radiation pattern plane in solid line and the simulated radiation pattern plane in dashed line.

The radiation pattern refers to the directional dependence of the power emitted (or received) by the antenna and is dependent on many factors: antenna configuration, operating frequency, presence of the other objects, etc. In this case, radiation pattern (see FIGS. 15A-B) of the textile integrated spiral antenna demonstrates a combination of the classical have-wave dipole radiation pattern and the one of multiple-turns spiral. Experimental measurements were conducted in an anechoic chamber using a known source on the transmission side and textile integrated antenna under study as a far-field receiver. The radiation patterns were measured in an anechoic chamber using wide-band (700 MHz-6 GHz) log-periodic directional antenna (Aaronia HyperLOG-7060 from Aaronia USA, Seneca, USA) and a tunable signal generator at the transmission side with the textile-integrated fiber antenna, fixed on a dielectric holder, acting as the far-field receiver.

The efficiency of an antenna (η) is related to its gain (G) and directivity (D) as G=ηD and it is defined as the power radiated relative to the power delivered to the antenna. It can be measured experimentally using the method based on Friis transmission equation [30] described in full details, for example, in a previous publications [22]. The line-of-site transmission measurements were performed in an unobstructed lab environment over the distance R=142 cm, with the antennas placed 1 m above the ground an RF absorber to prevent multipath reflections. Both antennas were connected to the network analyzer and gain values determined using the following equation:

$$|S_{21}|^2 = (1-|S_{11}|^2)(1-|S_{22}|^2) G_T G_R \left(\frac{c}{4\pi Rf}\right)^2 \qquad (1)$$

where $G_T$ and $G_R$ correspond to the gain and $S_{11}$ and $S_{22}$ to the return loss of the transmitting and receiving antennas, respectively. In this case, $S_{21}$ scattering parameters represents the power transmitted from one antenna to the other at certain frequency, f, and c is the speed of light. In this case, an antenna with a known gain, $G_T$, (Aaronia HyperLOG-7060 from Aaronia USA, Seneca, USA) was used on the transmission side. Thus, from Equation (1) it becomes possible to determine gain of the discussed spiral antenna, which equals 3.41 dBi. This value is directly comparable to the 3.45 dBi gain of a common rubber ducky antenna, in this example purchased from Bplus Technology Co. Ltd (Taipei, Taiwan).

As it was mentioned above, detection of the respiration rate with the proposed wearable respiration sensor relies on two mechanisms that are schematically shown in FIGS. 16A-C. The first mechanism refers to the geometry of the antenna, the second one to the change of dielectric properties of the human torso during breathing.

The fiber spiral antenna was integrated into a fitted cotton shirt at the mid-chest position (FIG. 16A), allowing the chest expansion to slightly stretch the antenna as shown in FIG. 16B. It is important to note that such stretching does not cause any elongation or deformation of the metal-glass-polymer fibers themselves, only the radii of the spiral. At the same time, when a person inhales or exhales air from their lungs, the dielectric properties of the whole torso are noticeably changed. For example, the relative permittivity, $\varepsilon_r$, of the inflated lungs at 2.45 GHz equals to 20.51 while the relative permittivity of deflated lungs at the same frequency equals to 48.45 [31]. The performance of the antenna is affected by this variation of the dielectric properties of its surroundings [32], which again results in the central frequency shift. In the next sections, these two mechanisms will be studied with the help of custom mechanical stretching setup and body phantoms.

Figure 17:
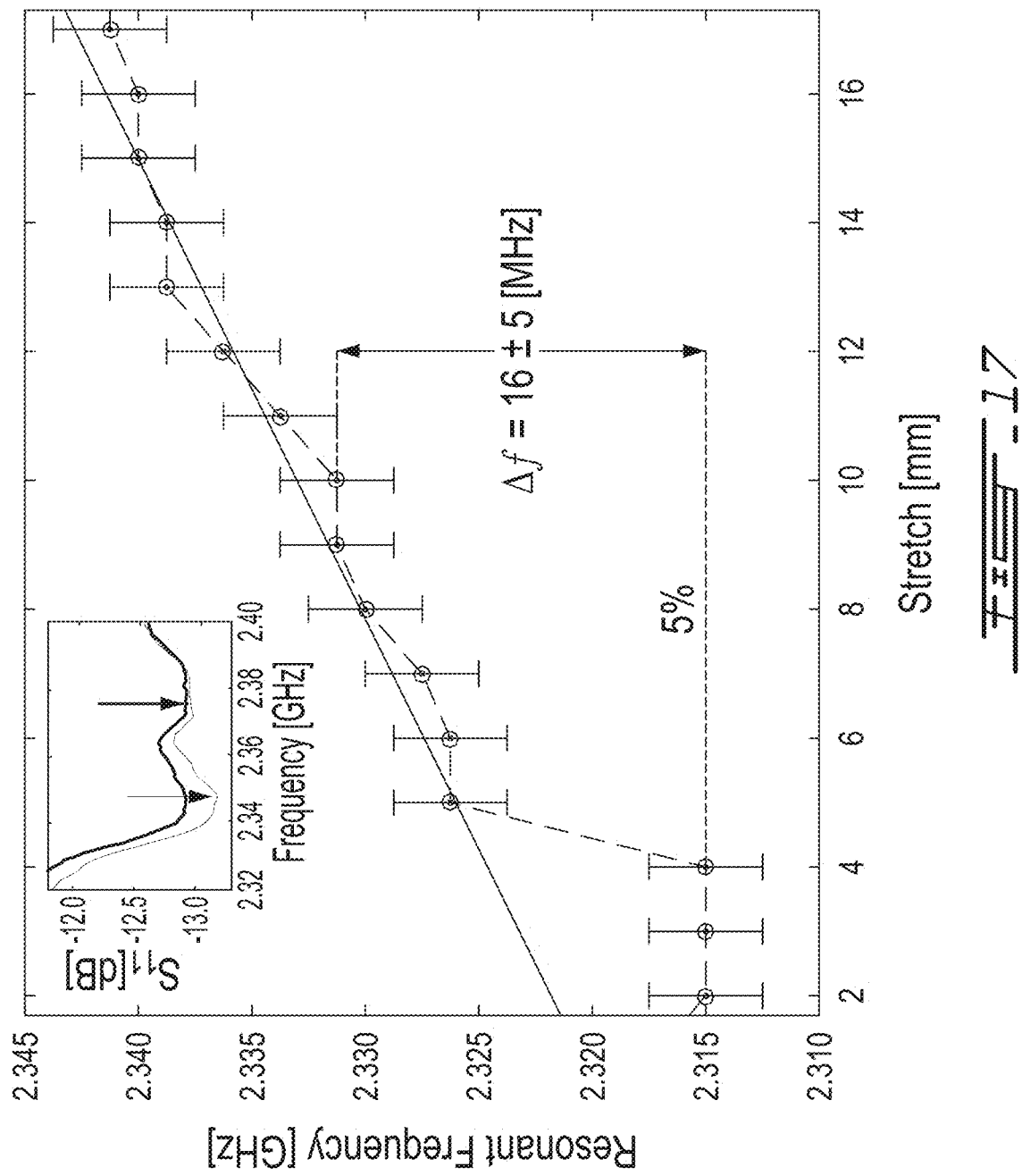
FIG. 17 is a graph showing resonance frequency of the dipole antenna of the wearable respiration sensor of FIG. 13 as function of the induced stretch in an off-body scenario.

In order to assess performance of the multi-material fiber spiral antenna under stretching load it was integrated into 20 cm×10 cm cotton patch, one side of the patch was fixed by a clamp while the other one was attached to the manual translation stage (1 mm step). The $S_{11}$ graphs were measured for every millimeter the textile patch was stretched. Behavior of the resonant frequency of the antenna as a function of the induced stretch is shown in FIG. 17. The abrupt change in the 6-8 mm stretch range is explained by the concurrence of the two relative minimums in the $S_{11}$ parameter graph as shown in the inset in FIG. 17. At the same time, the linear approximation of the 5-16 mm stretch region allows estimation of the respiration sensor sensitivity as 1.4 MHz/mm. It can be seen that 5% stretch (based on the initial 10 cm length of the sample), that corresponds to the expected chest expansion [27], leads to the 16.2 MHz resonant frequency shift.

The close proximity of the human body can significantly alter performance of any antenna [33]. This effect is well known in the field of implantable antennas [34], particularly the downshift of the resonant frequency. Since the sensing mechanism of the proposed spiral fiber antenna also relies on the resonant frequency shift, it becomes crucial to investigate its performance in the proximity of a human body phantom. Therefore, the stretching test described above was repeated in the presence of a 17 cm×12 cm×3 cm body phantom at 6 mm distance from the textile sample plane. While the 6 mm distance originates from the physical constraints of the experimental setup, it also seems reasonable for a standard scenario of a normal shirt on the torso of a user. The human body is a very complex, inhomogeneous, layered structure with different tissues having different dielectric properties [31] and the great variety of corresponding models have already been developed [35]. In this case, a body phantom representing only muscle tissue was used. It was fabricated according to the guidelines found in the literature [36], particularly 60% (by weight) of deionized water, 40% of sugar, and 2 g of gelatin powder per 100 mL.

In FIG. 18, the resonant frequency shift of the textile integrated spiral fiber antenna as a function of the induced stretch with and without the body phantom is shown. It can be seen that although the absolute frequency value with body phantom is lower, the relative frequency shift is still easily detectable and for the 5% stretch equals to approximately 6 MHz. The results shown in FIGS. 17 and 18 were obtained with different prototypes (of the same design) and, thus, there is a certain variation in the resonant frequency, which is not crucial since the sensing mechanism depends on its change rather than absolute value.

Figure 19A:
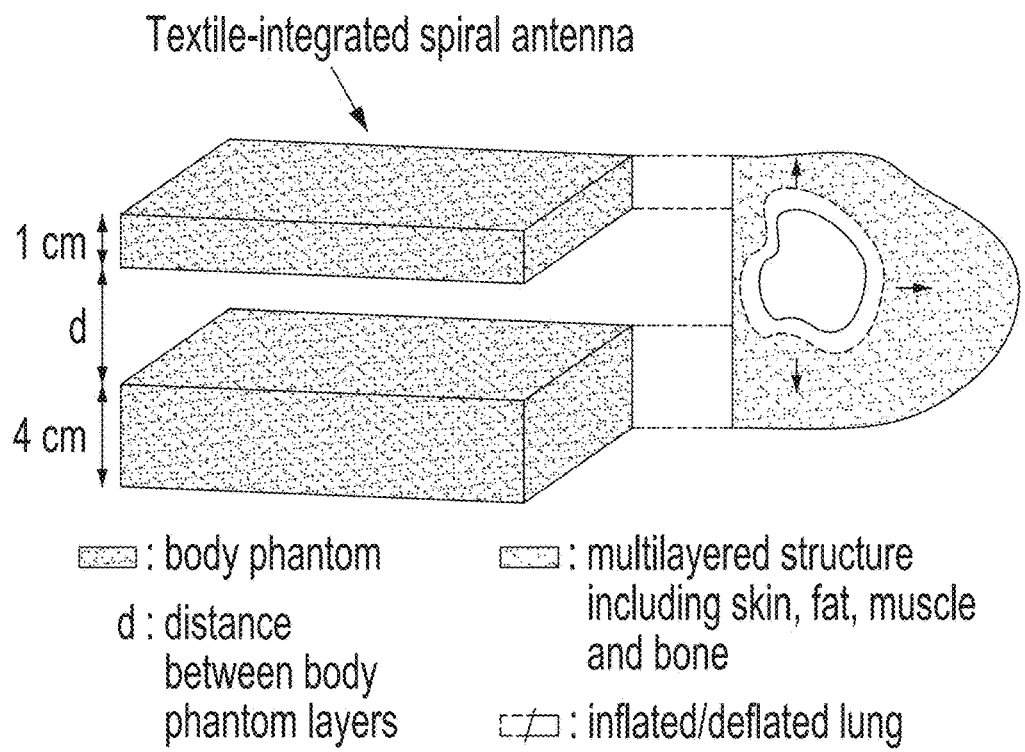
FIG. 19A is a schematic view of a two-layer human body phantom setup to replicate chest movement during breathing, for simulation purposes.

The second mechanism involved into respiration sensing with the proposed spiral antenna is related to the change of the air volume inside the lungs and inner configuration of the thoracic cage. In order to investigate this mechanism another experiment was conducted, this time using the two-layer body phantom as shown in FIG. 19. This setup was aimed to reproduce the breathing movement when the back of the subject would remain steady and contraction of the intercostal muscles would force the expansion of the chest. It should be noted that this is of course an oversimplification of the real situation as the setup does not take into account the real structure of the thoracic cage and displacement distance will be different for each user and depend on the position of the antenna on the user's chest. However, this kind of measurements still can be used to illustrate the discussed effect.

Figure 19B:
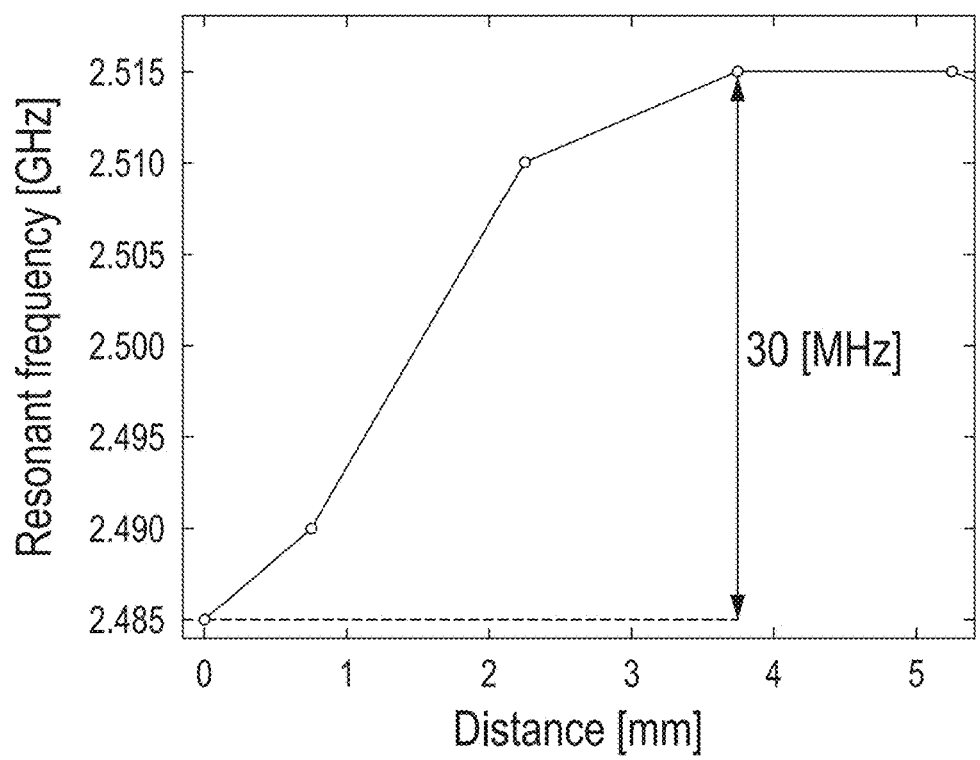
FIG. 19B is a graph showing the resonance frequency of the dipole antenna of the wearable respiration sensor of FIG. 13 as function of a distance d between the two layers of the human body phantom of FIG. 19A.

The shift of the spiral antenna resonant frequency depending on the displacement of the second phantom layer is shown in FIG. 19B. It can be seen that, for example, the displacement of 3.6 mm leads to the significant shift of 30 MHz. The same increase in the chest diameter, if considering the lungs as two cylinders with the height of 20.5 cm and a volume of 2262 cm³, as reported in [37], will result in the 312 mL volume change. While, tidal volume intakes are often estimated as 7 mL/kg [26], which for a 75 kg body mass yields 525 mL. This is, of course, a very rough estimation, which is only meant to provide a reference point. From one side, the real human body is a much more complex and inhomogeneous structure. From the other, the discussed frequency shift occurs towards the higher frequencies, the same as in the case of pure mechanical stretching (see FIG. 18). Therefore, it is reasonable to expect that these two mechanisms combined together in the real-world scenario will result in a greater frequency shift, thus increasing sensitivity of the proposed sensor.

Finally, real-world respiration tests were conducted with the help of two male volunteers. The volunteer whose breathing pattern is presented in FIG. 20 was sitting steadily during the recording and could not see the data being recorded. The volunteer was asked to take four deep breaths, followed by one minute of relaxed, shallow breathing, and four more deeps breaths. As before, the resonant frequency shift was continuously measured using a HP Agilent 8722ES network analyzer connected to a PC via a GPIB interface. The acquisition rate was set to provide one measurement per second.

From FIG. 20 it can be seen that the two mechanisms, combined, result in a noticeable frequency shift that allowed the correct detection of the breathing pattern of the volunteer.

For deep breathing, frequency shifts as large as 120 MHz were detected, while relaxed, shallow breathing led to smaller, 4-15 MHz, but still detectable, frequency shifts. The measurements were also repeated in sitting and lying positions, as well as with the help of a second male volunteer, as shown in FIGS. 21A-D, respectively. From the obtained results, several important conclusions can be made. First, the absolute value of the frequency shift is different for different scenarios. For example, shallow breathing peaks (15 MHz) are clearly more pronounced in the sitting position (FIG. 21A) and deep breathing peaks are almost twice as large in in the lying position (200 MHz, see FIG. 21C) as in the standing (100 MHz) scenario (FIG. 21B). This can be explained both by the change in the configuration and position of the sensor and by the change in the user's chest movement while breathing. Still, the breathing pattern itself (four deep breaths, eight shallow breaths, four more deep breaths) was unmistakably detected in all the test scenarios. Second, by comparing two graphs obtained for two volunteers (FIG. 21D) the differences in breathing patterns can be observed (the second volunteer has a larger volume of the lungs and generally takes sharper breaths).

The goal of this example is to validate the proposed wearable respiration sensor based on multi-material fibers, integrated into a standard cotton shirt in the spiral antenna arrangement, for the respiration rate detection. Head-to-head comparison with the gold standard of spirometry or pneumography measurements, as well as additional tests, for example, on patients with respiratory problems, requires input from the qualified medical personnel and special equipment, and should become a subject of the future work. One advantage of the proposed approach can consist of high user comfort associated with the traditional garments, as it does not require direct skin contact or attachment of the electrodes of any kind. This can become particularly important in such cases as monitoring of the respiration rate of the newborn infants. In the experiments reported in this paper the $S_{11}$ graphs and, thus, resonant frequency of the spiral fiber antenna, were continuously measured using a vector network analyzer. However, for mobile applications another detection schemes can be used, for example, based on the measurement of the power transmitted through the narrow band filter over wireless communication network belonging to the ISM band, such as Bluetooth.

In conclusion of this example, contactless textile integrated respiration sensor suitable for detection, and simultaneous transmission over civilian wireless networks, of the wide range of breathing patterns was demonstrated. The sensor was made using multi-material metal-glass-polymer fibers in the arrangement of a spiral antenna designed to operate at 2.4 GHz frequency. Off- and on-body measurements have shown that the breathing detection is made possible by the two mechanisms: the change of the antenna configuration due to mechanical stretching, and the change of dielectric properties of the human torso during the respiration. Both effects contribute to the shift of the antenna resonant frequency toward higher frequency range. Respiration patterns for two male volunteers were recorded with the help of a sensor prototype integrated into standard cotton t-shirt in sitting, standing and lying scenarios. Typical measured frequency shifts for the deep breathing lies in the range of 120-200 MHz, and 10-15 MHz for shallow breathing. Future work will aim the adaptation of the technology to newborn infants where comfort is a priority.

1. Hung, K.; Lee, C. C.; Choy, S.-O. Ubiquitous Health Monitoring: Integration of Wearable Sensors, Novel Sensing Techniques, and Body Sensor Networks. In Mobile Health; Sasan A., Ed.; Springer International Publishing: Cham, Switzerland, 2015; pp. 319-342.
2. Shyamal, P.; Hyung, P.; Paolo, B.; Leighton, C.; Mary. R. A Review of Wearable Sensors and Systems with Application in Rehabilitation. J. NeuroEng. Rehabil. 2012, 9, 1-17.
3. Kay, M.; Santos, J.; Takane, M. Mhealth: New Horizons for Health through Mobile Technologies; World Health Organization: Geneva, Switzerland, 2011; Volume 64, p. 66.
4. Dziuda, L.; Skibniewski, F. W.; Krej, M.; Lewandowski. J. Monitoring Respiration and Cardiac Activity Using Fiber Bragg Grating-Based Sensor. IEEE Trans. Biomed. Eng. 2012, 59, 1934-1942.
5. Guo, L.; Berglin, L.; Li, Y. J.; Mattila, H.; Mehrjerdi, A. K.; Skrifvars, M. Disappearing Sensor-Textile Based Sensor for Monitoring Breathing. In Proceedings of the 2011 International Conference on Control, Automation and Systems Engineering (CASE), Singapore, 30-31 Jul. 2011.
6. Grenvik, A.; Ballou, S.; McGinley, E.; Millen, J. E.; Cooley, W. L.; Safar, P. Impedance Pneumography: Comparison between Chest Impedance Changes and Respiratory Volumes in 11 Healthy Volunteers. Chest 1972, 62, 439-443.
7. Leonard, P.; Beattie, T.; Addison, P.; Watson, J. Standard Pulse Oximeters Can Be Used to Monitor Respiratory Rate. Emerg. Med. J. 2003, 20, 524-525.
8. Boyle, J.; Bidargaddi, N.; Sarela, A.; Karunanithi, M. Automatic Detection of Respiration Rate from Ambulatory Single-Lead Ecg. IEEE Trans. Inf. Technol. Biomed. 2009, 13, 890-896.
9. Lazaro, A.; Girbau, D.; Villarino, R. Analysis of Vital Signs Monitoring Using an Ir-Uwb Radar. Prog. Electromagn. Res. B 2010, 100, 265-284.
10. Lorussi, F.; Scilingo, E. P.; Tesconi, M.; Tognetti, A.; De Rossi, D. Strain Sensing Fabric for Hand Posture and Gesture Monitoring. IEEE Trans. Inf. Technol. Biomed. 2005, 9, 372-381.
11. Yang, C. M.; Wu, C. C.; Chou, C. M.; Yang, T. L. Vehicle Driver's Ecg and Sitting Posture Monitoring System. In Proceedings of the 9th International Conference on Information Technology and Applications in Biomedicine, Larnaca, Cyprus, 4-7 Nov. 2009.
12. Cheng, J.; Amft, O.; Lukowicz, P. Active Capacitive Sensing: Exploring a New Wearable Sensing Modality for Activity Recognition. In Proceedings of the 8th International Conference on Pervasive Computing; Springer: Berlin, Germany, 2010; pp. 319-336.
13. Torsten, L.; Lena, G.; Geert, L. Contactless Emg Sensors Embroidered onto Textile. In 4th International Workshop on Wearable and Implantable Body Sensor Networks (Bsn 2007); Steffen, L., Thomas, F., Petri, M., Eds.; Springer: Berlin, Germany, 2007; pp. 29-34.
14. Chi, Y. M.; Cauwenberghs, G. Wireless Non-Contact Eeg/Ecg Electrodes for Body Sensor Networks. In Proceedings of the 2010 International Conference on Body Sensor Networks (BSN), Singapore, 7-9 Jun. 2010.
15. Singh, N.; Singh, A. K.; Singh, V. K. Design and Performance of Wearable Ultrawide Band Textile Antenna for Medical Applications. Microway. Opt. Technol. Lett. 2015, 57, 1553-1557.
16. Kumar, G.; Ray, K. P. Broadband Microstrip Antennas; Artech House: London, U K, 2003.
17. Huang, C. T.; Tang, C. F.; Shen, C. A Wearable Textile for Monitoring Respiration, Using a Yarn-Based Sensor. In Proceedings of the 2006 10th IEEE International Symposium on Wearable Computers, Montreux, Switzerland, 11-14 Oct. 2006.
18. Lanlin, Z.; Zheyu, W.; Volakis, J. L. Textile Antennas and Sensors for Body-Worn Applications. Antennas Wrel. Propag. Lett. IEEE 2012, 11, 1690-1693.
19. Sorin, F.; Abouraddy, A. F.; Orf, N.; Shapira, O.; Viens, J.; Arnold, J.; Joannopoulos, J. D.; Fink, Y. Multimaterial Photodetecting Fibers: A Geometric and Structural Study. Adv. Mater. 2007, 19, 3872-3877.
20. Egusa, S.; Wang, Z.; Chocat, N.; Ruff, Z. M.; Stolyarov, A. M.; Shemuly, D.; Sorin, F.; Rakich, P. T.; Joannopoulos, J. D.; Fink, Y. Multimaterial Piezoelectric Fibres. Nat. Mater. 2010, 9, 643-648.
21. Gorgutsa, S.; Blais-Roberge, M.; Viens, J.; LaRochelle, S.; Messaddeq, Y. User-Interactive and Wireless-Communicating RF Textiles. Adv. Mater. Technol. 2016, 1, 1600032.
22. Gorgutsa, S.; Khalil, M.; Belanger-Garnier, V.; Viens, J.; Gosselin, B.; LaRochelle, S.; Messaddeq, Y. Emissive Properties of Wearable Wireless-Communicating Textiles Made from Multimaterial Fibers. IEEE Trans. Antennas Propag. 2016, 64, 2457-2464.
23. Lobodzinski, S. S. Ecg Patch Monitors for Assessment of Cardiac Rhythm Abnormalities. Prog. Cardiovasc. Dis. 2013, 56, 224-229.

24. Lee, Y.-D.; Chung, W.-Y. Wireless Sensor Network Based Wearable Smart Shirt for Ubiquitous Health and Activity Monitoring. Sens. Actuators B Chem. 2009, 140, 390-395.
25. Warren, J. B.; Anderson, J. M. Newborn Respiratory Disorders. Pediatr. Rev. 2010, 31, 487.
26. Beardsell, I.; Bell, S.; Robinson, S.; Rumbold, H. Get through Mcem Part A: Mcqs; Hulbert, D., Ed; CRC Press: Boca Raton, Fla., USA, 2009.
27. Moll, J. M.; Wright, V. An Objective Clinical Study of Chest Expansion. Ann. Rheum. Dis. 1972, 31, 1-8.
28. Benet, W. E. The Mechanism of the Reaction of the Tollen Reagent. J. Chem. Res. 2011, 35, 675-677
29. Dicke, R. H. A Computational Method Applicable to Microwave Networks. J. Appl. Phys. 1947, 18, 873-878.
30. Shaw, J. A. Radiometry and the Friis Transmission Equation. Am. J. Phys. 2013, 81, 33-37.
31. Camelia, G.; Sami, G. Compilation of the Dielectric Properties of Body Tissues at Rf and Microwave Frequencies; Brooks Air Force Base, Texas, Armstrong Laboratory (AFMC), Occupational and Environmental Health Directorate, Radiofrequency Radiation Division: San Antonio, Tex., USA, 1998.
32. Ida, N. Engineering Electromagnetics; Springer International Publishing: Cham, Switzerland, 2015.
33. Moore, R. K. Effects of a Surrounding Conducting Medium on Antenna Analysis. Antennas Propag. IEEE Trans. 1963, 11, 216-225.
34. Jaehoon, K.; Rahmat-Samii, Y. Implanted Antennas inside a Human Body: Simulations, Designs, and Characterizations. Microw. Theory Tech. IEEE Trans. 2004, 52, 1934-1943.
35. Ito, K. Human Body Phantoms for Evaluation of Wearable and Implantable Antennas. In Proceedings of the Second European Conference on Antennas and Propagation, EuCAP 2007, Edinburgh, UK, 11-16 Nov. 2007.
36. Karacolak, T.; Hood, A. Z.; Topsakal, E. Design of a Dual-Band Implantable Antenna and Development of Skin Mimicking Gels for Continuous Glucose Monitoring. Microw. Theory Tech. IEEE Trans. 2008, 56, 1001-1008.
37. Kramer, G. H.; Capello, K.; Bearrs, B.; Lauzon, A.; Normandeau, L. Linear Dimensions and Volumes of Human Lungs Obtained from Ct Images. Health Phys. 2012, 102, 378-383.

Example 2—A Portable Wireless Communication Platform Based on a Multi-Material Fiber Sensor for Real-Time Breath Detection In this example, a new mobile wireless wearable respiration sensor for real-time monitoring of an individual's breathing rate. The platform takes the form of a wearable stretching T-shirt featuring a sensor and a detection base station. The sensor is formed by a spiral-shaped antenna made from a multi-material fiber connected to a compact transmitter. Based on the resonance frequency of the antenna at approximately 2.4 GHz, the breathing sensor relies on its Bluetooth transmitter. The contactless and non-invasive sensor is designed without compromising the user's comfort. The sensing mechanism of the system is based on the detection of the signal amplitude transmitted wirelessly by the sensor, which is found to be sensitive to strain. Capabilities of the platform to detect the breathing rates of four male volunteers who are not in movement have been demonstrated. The breathing pattern is obtained through the received signal strength indicator (RSSI) which is filtered and analyzed with home-made algorithms in the portable system. Numerical simulations of human breath are performed to support the experimental detection, and both results are in a good agreement. Slow, fast, regular, irregular, and shallow breathing types are successfully recorded within a frequency interval of 0.16-1.2 Hz, leading to a breathing rate varying from 10 to 72 breaths per minute.

Changes in breathing rate are considered to be an important indicator of major physiological and pathological instabilities, such as cardiopulmonary disease, among others [1]. The breathing rate is the number of breaths a person takes per minute. The normal breathing rate of an adult at rest is about 14 breaths/min (bpm) [2], while a newborn's breathing rate is 37 bpm [3]. Abnormal respiration rates for adults can be categorized as hyperventilation (bpm 24), hypoventilation (bpm 10), or apnea [4]. The lack of tools for continuous and accurate monitoring open up huge opportunities for novel sensor development [5,6]. Existing respiration monitoring systems are usually contact-based methods. Manual methods are most commonly used for measuring breathing rate. However, these methods are unreliable and prone to error. A thermistor-based method and a technique using strain-gage pressure sensors incorporated in a strap to detect chest and abdominal movements were proposed [7,8]. Also, a capacitive sensor was utilized to determine respiratory patterns through chest expansion [9,10]. A contactless breath monitoring approach can provide an attractive alternative for monitoring breathing rate. In this line of research, infrared thermography based on wavelet decomposition [11], thermal sensors [12], thermal imaging [13], camera-based systems [14], real-time vision-based methods [15], narrow-band radars [16], ultra-wide band (UWB) radars [17], and passive radar techniques [18] were proposed. Furthermore, advances in computing technology have resulted in the development of complex algorithms for respiration monitoring. For example, a three-dimensional (3D) vision tracking algorithm has been developed to measure the breathing rate [19]. Although these methods have the advantage of being contactless, they require complex measurement equipment and signal analysis, and suffer from difficulty of usage and inaccuracy according to Al-Khalidi et al. [20]. Textile based sensors or smart textiles are other important technologies which provide more comfortable and user-friendly approaches for respiration monitoring. The sensors are integrated into the threads and fibers comprising the textiles, such as conductive yarn [21], and conductive polymers [22], or are incorporated into textiles in the form of piezoelectric sensors [23], fiber optic sensors [24], fiber Bragg grating-based sensors [25,26], multi-material fiber sensors [27], and antennas [28]. Recently, Ravichandran et al. developed a wireless system operating at a 2.4-GHz frequency to estimate the respiration rate [29]. Although the presented system was able to track the breathing of an individual with an accuracy of 1.54 bpm, the authors stressed the limitations in the detection algorithms for accurately estimating the respiration rate. Other techniques monitored breathing rate by measuring the received signal strength indicator (RSSI) in wireless networks using numerous sensors [30] or a single transmitter-receiver pair [31,32]. In both cases the signal processing requires heavy mathematical treatment and the patient is limited to lying in the bed.

To overcome all these problems, the inventors developed a novel non-invasive sensor for contactless monitoring of the breathing rate [27,33]. The sensor is a spiral antenna made from a multi-material metal-glass-polymer fiber emitting and receiving at 2.4 GHz. It is positioned on the volunteer's chest. The sensor is integrated into a standard cotton T-shirt, and records the respiration patterns through the continuous measurement of the return loss $S_{11}$ and the resonant frequency shift of the fiber antenna using a vector network analyzer (VNA).

In this example, a new mobile platform prototype for real-time breath detection by measuring the RSSI signal through IEEE 802.15.4 and a Bluetooth protocol at 2.4 GHz is proposed. The breath sensor consists of the spiral-shaped fiber antenna connected to a miniaturized Bluetooth transmitter. The fiber antenna is designed to transmit data over wireless communication networks at 2.4 GHz. When a person wearing the T-shirt starts breathing, the antenna shape changes and so does the resonance frequency and the transmitted signal strength. The strength of the signal depends upon the chest movement. Breathing signals of four male volunteers (who were not in motion) were successfully recorded with regular breathing rates at different distances from the base station. Using ANSYS HFSS software, numerical breath calculations of a simulated human body (SHB) were performed and the results support the experimental breathing rate detected by the sensor. It is important to emphasize that for medical applications, the detection of changes in a patient's breathing pattern and respiration rate is far more important than just determining the respiration rate [34,35]. For example, respiratory distress could be diagnosed from a significant change in respiration rate or repetitive shallow breaths of an individual. Also, detection of time periods where there is no breathing signal or discontinuities in the breathing signal can help in the diagnosis of sleep apnea. Using this designed platform, different classes of breathing have been successfully detected such as: slow, fast, shallow, and irregular patterns and rates with frequencies varying from 0.16 to 1.2 Hz.

The proposed portable platform to monitor the respiration is composed of four parts: a spiral fiber antenna integrated into a textile, a transmission module, an energy harvesting module, and a base station. The working mechanism of the platform can be explained in three main steps as reported schematically in FIGS. 22A-D: (1) the breathing sensor is stitched on an elastic T-shirt worn by a volunteer and placed horizontally in the pectoral region of the chest; (2) breathing causes significant chest movement; and (3) the transmitted signal from the sensor is sensitive to strain caused by the chest movement, so it can be used for monitoring the breathing signal. The size of the T-shirt was chosen to fit all the volunteers body shapes.

The antenna is fabricated from multi-material fibers consisting of polyimide-coated hollow-core silica capillaries with an inner radius of 100 m and outer radius of 181 m, with an 18-m-thick polyimide layer. A thin silver layer was plated on the inner surface of the hollow core [27]. An electrical DC resistance of 3.8±1 Ω/cm was measured for the inner silver layer. When the length of the antenna is 10 cm, good impedance matching (50Ω) with the standard electronic components is achieved. Using the silver-doped hollow-core fiber, a half-turn spiral antenna was fabricated as shown in FIG. 23. The spiral shape of the antenna provides higher sensitivity versus the deformation of the human chest during respiration.

The transmission module is a Bluetooth transceiver (Nordic Semiconductors SoC nRF51822) transmitting and receiving at a band rate of 250 kbps. The transmitter is a compact low energy-consuming device. It was stitched into a T-shirt and soldered to the antenna legs as shown in FIG. 23.

With environmental concerns expressed in headlines worldwide, the focus is to equip the transmitter with a durable power source that would recharge itself while in use. The energy harvesting is achieved through BQ25570 chip (Texas Instruments, Texas, USA). This chip is connected simultaneously to a solar panel and a small flexible rechargeable battery. The solar energy is harvested from two small commercially available solar cells (1.2 V, 200 mW). The solar cells are connected to the rechargeable battery to recharge it when the battery voltage goes below 3 V up until it reaches 4.3 V. The output voltage is regulated by the power management chip. Efficient charging is observed when the solar cell is exposed to 3021 lux (source light radius is 3 cm and solar cell light source distance is 10 cm). The collected power is sufficient for the battery to stay charged at all times. The collected energy is 3 mW when the solar cell is closely and directly exposed to indoor light. The solar cells are used only to keep the battery charged.

The breathing pattern is extracted from the variation of the signal strength emitted at 2.4 GHz from the T-shirt's sensor. The base station can be a smartphone, a tablet, or a computer with a Bluetooth module. This designed base station is composed of a Raspberry Pi connected to a touch screen and a micro-controller (Quark SE C1000, Intel, USA). The communication between the micro-controller and the Raspberry Pi is ensured by a universal asynchronous receiver-transmitter (UART).

Once it is programmed, the transmitter acts as an advertising beacon on three channels following the Bluetooth Low Energy (BLE) protocol with a center frequency at 2.4 GHz over a narrow bandwidth of 80 MHz. When the micro-controller receives the Bluetooth signal from the transmitter sensor, it estimates the signal power through RSSI and sends all the collected values through serial communication to the Raspberry Pi. In the tested environment, this sampling method is sufficient as the breathing amplitude signal versus the noise level (SNR) is 4.9 in the best case. The sampling period is set to 20 Hz to measure the maximum breathing rate of 1.2 Hz, which satisfies the Shannon constraint. All data are displayed and plotted in real time. The breathing pattern is extracted using a home-made algorithm integrated into the Raspberry Pi. The algorithm processes data every 5 s in a window size of 40 s using a Kaiser windowing algorithm with a β coefficient of 0.6. The reliability of this algorithm was tested using a Lenovo Think Pad P51 with intel core i7 and the execution time of 0.05 s. The implemented algorithm does not slow down the acquisition program when running on a separate thread with the Raspberry Pi.

Data is first filtered by a band-pass Butterworth filter with a cut-off frequency of 0.2-1.9 Hz. The center frequency of the filter is chosen with respect to the maximum and minimum breathing frequency expected from a human subject under normal conditions. The low-frequency components of the signal are filtered since the RSSI signal usually has an average value of −60 dBm. However, this value depends on the distance and the medium conditions between the emitter and the receiver. The highest breathing frequency detected by the system is 1.5 Hz. Indeed, fast breathing is not expected to be higher than 1.5 Hz even in abnormal conditions. The higher cut-off frequency (−3 dB) is then chosen at 1.9 Hz to remove all high frequencies and noises. This filter has a stable frequency response, and is used to remove the DC-component of the curve (as the usual RSSI measurements range from −45 dBm to −80 dBm), in order to smooth the curve, and attenuate all frequency components that exceed a predetermined maximum breathing frequency of 1.5 Hz. Then, a fast-Fourier transform (FFT) is applied to the treated signal in order to detect the dominant frequency, which could be associated to the breathing pattern. If none is found, the algorithm uses a continuous wavelet transform (CWT) method with Ricker wavelets to detect the number of peaks in the window. The advantage of using both the FFT and CWT methods is to accurately extract the respiration pattern, unlike in [29,31] where only FFT was used. Indeed the breathing frequency can vary inside the window, as a breathing signal can be periodic or not.

The designed antenna was first characterized in terms of radiation performance. The key parameters that describe the antenna resonance frequency are the S-parameters, and more specifically $S_{11}$. For best performance, a good impedance match must be observed between the antenna and the standard 50Ω cable. The performance of the spiral antenna was experimentally and numerically analyzed using ANSYS HFSS software.

Figures 24A, 24B:
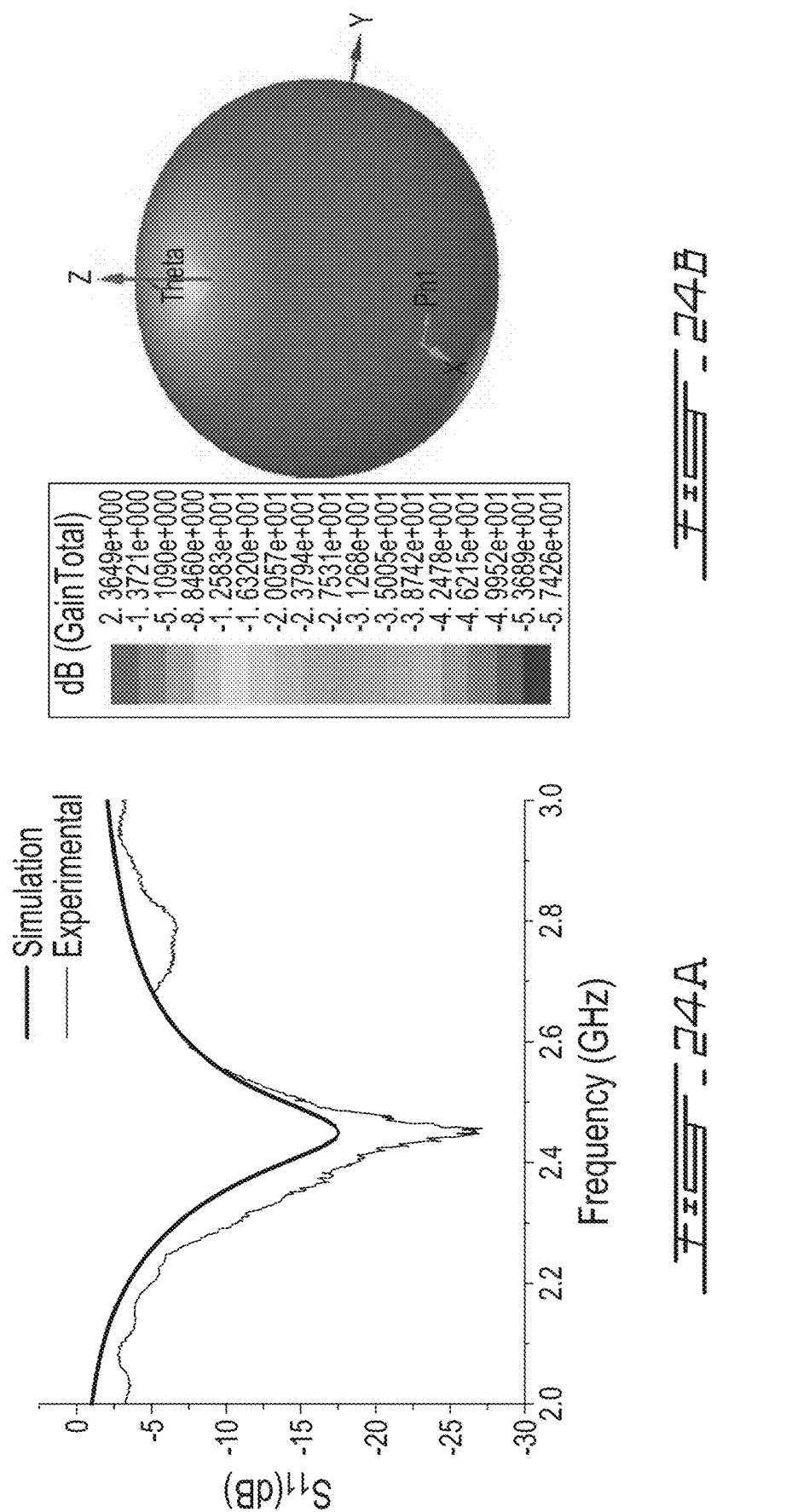
FIG. 24A is a graph showing return loss as function of frequency for the dipole antenna of FIG. 23, with the measured return loss in dashed line and the simulated return loss in solid line.
FIG. 24B is a graph showing three-dimensional (3D) plot of a gain of the dipole antenna of FIG. 23 in the x, y, and z directions obtained using a simulation software.
Figure 25A:
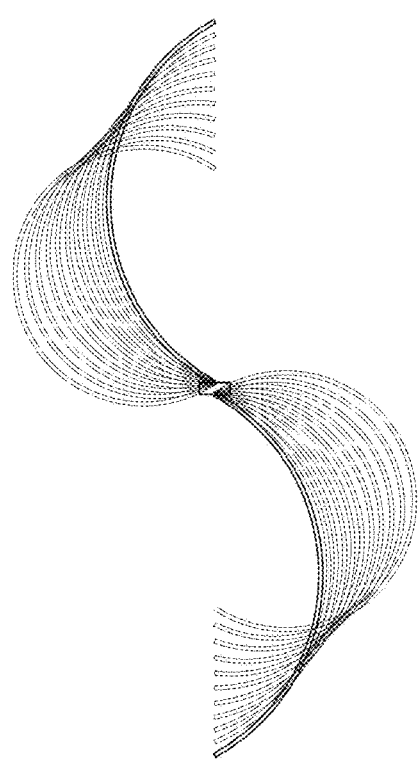
FIGS. 25A-D include graphs showing representation of induced deformations applied to the dipole antenna of FIG. 23, upon stretching, compressing, bending, and folding, respectively, using a simulation software.
Figure 25B:
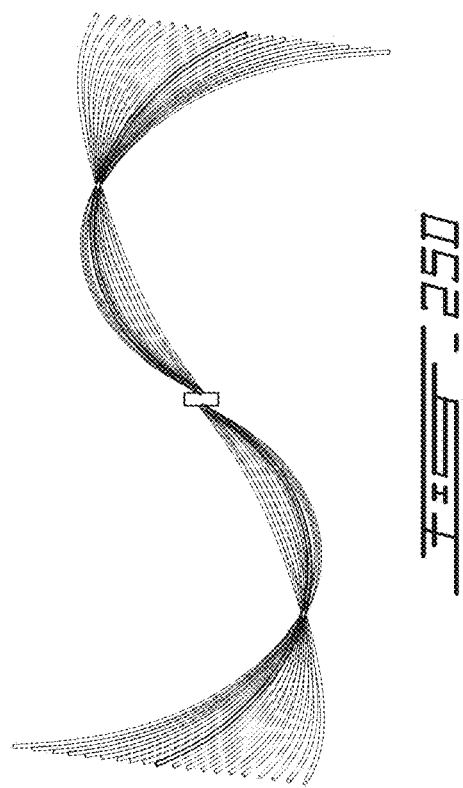
Figure 25C:
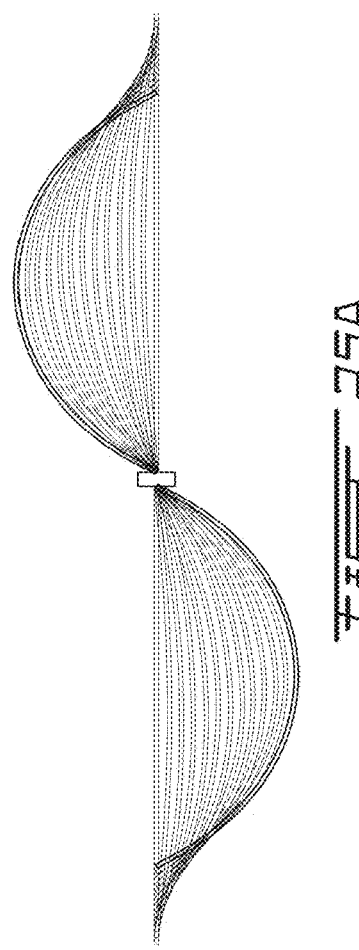
Figure 25D:
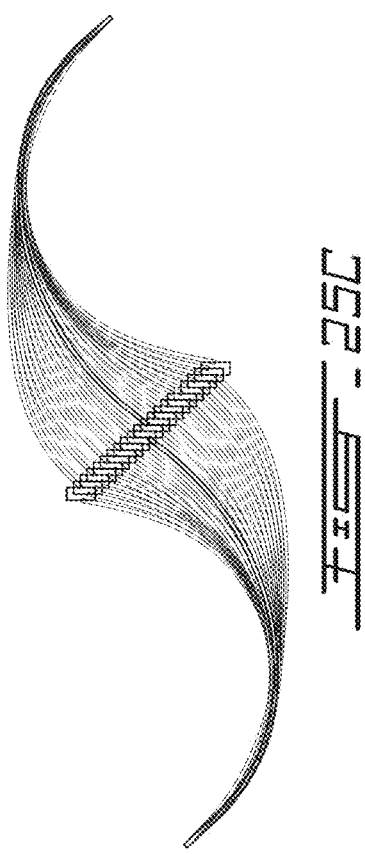

The antenna was first integrated into a stretchable T-shirt (available commercially). Then, it was connected electrically to either an SMA connector or to the transmitter module. Using the SMA connector, the resonant frequency shift and the return loss $S_{11}$ were continuously measured using a VNA (HP Agilent 8722ES, USA). as been sourced. The connection between the VNA and the SMA connector was performed using a 50Ω, coaxial cable. Measured and simulated $S_{11}$ in free space are shown in FIG. 24A. From this figure, it can be seen that the antenna radiates at 2.43 GHz. Both experimental and numerical results are in a good agreement in terms of central frequency and $S_{11}$ signal shape.

The efficiency of an antenna is related to its gain and directivity. It is defined as the power radiated relative to the power delivered to the antenna. The spiral fiber antenna gain was measured previously [27,28] at 3.45 dBi using the Friis equation approach [36]. In this case, a 3D simulation for the spiral fiber antenna gain as a function has been performed for the x, y, and z axis using ANSYS HFSS. The result shown in FIG. 24B reveals a donut-shaped radiation pattern. In this case, the transmitted power along the z-axis is very weak (−35.00 dB to −1.37 dB). However, in the x-y plane the radiation is maximum. The plot is very useful for visualizing in which direction the antenna radiates. Therefore, based on this result the spiral antenna gain is about 2.37 dBi, which is in good agreement with the dipole antenna gain (2.15 dBi) [37].

During respiration, inhalation is primarily due to the contraction of the human diaphragm. The contraction of the diaphragm due to the enlargement of the thoracic cavity causes the intra-thoracic pressure to fall. The latter induces lung expansion due to inspiration. However, during exhalation the diaphragm and inter-costal muscles relax. Consequently, the chest and abdomen return to the rest position. The key feature of this spiral fiber antenna design is its flexibility against stretching, shortening, twisting, or bending to detect the human chest movement. In this example, the antenna has been exposed to different induced deformation scenarios, reflecting the real environment that the antenna could face during respiration. The variation of the $S_{11}$ signal and the resonant frequency shift as a function of the induced deformation using ANSYS FHSS numerical simulations in free space have been studied. Simulating the induced effects of the deformations, particularly the stretching and compressing, on the antenna requires an accurate control of the arc length and the angle of curvature of the spiral antenna. These are related by the equation of curvature defined as $A=2\pi \times R \times (\theta/360)$, where A is the arc length, θ is the angle of curvature, and R is the radius of the arc. It should be noted that the arc length of the spiral antenna legs is maintained constant for all the deformations. In FIGS. 25A-D, a sketch of the fiber spiral antenna in free space is presented. As shown, the spiral antenna is subject to stretching (see FIG. 25A), compressing (see FIG. 25B), bending (see FIG. 25C), and folding (see FIG. 25D) deformations. The simulations of the $S_{11}$ signal and central frequency shift were performed in steps of 1 mm for all the induced deformations. The behavior of the resonant frequency of the antenna as a function of the induced stretching and compressing is shown in FIG. 26A-B, respectively. It can be seen that the variation of the frequency with the induced stretching deformation is linear when the antenna is elongated from (0 mm 120°) to (5 mm, 0°), with a maximum shift of 60 MHz. For the induced compression the variation of the central frequency from (0 mm, 120°) to (2.6 mm, 150°) is relatively small (3 MHz) and drops linearly after that to reach 79.3 MHz. This frequency shift is relatively close to the one obtained for the stretching deformation. In FIGS. 26A-D, the central frequency shift induced by the bending (c) and the folding (d) deformations over a 5-mm length has been shown to be about 50 MHz and about 70 MHz, respectively. These studies allow estimation of the spiral fiber antenna sensitivities, which are summarized in Table 1 for each induced deformation.

TABLE 1

The antenna fiber's sensitivity for each induced deformation.

| Deformation | Sensitivity (MHz/mm) |
| --- | --- |
| Stretching | 14.2 |
| Compressing | 11.8 |
| Bending | 10.0 |
| Folding | 14.0 |

The performance of the antenna is affected with the proximity of any conductive medium [38]. A simplified model of a human body with the corresponding dielectric properties was implemented in ANSYS HFSS in order to study the performances of the spiral fiber antenna. The advantage of using a SHB rather than the body phantom [39] is related to the fact that the SHB takes into account the effects of the dielectric properties and the deformation of the chest on the central frequency shift simultaneously.

During breathing, chest expansion could vary from 1 cm to approximately 3 cm. To detect this variation a complete human model has been imported inside the ANSYS environment [40]. The model is a simplified version of the exterior human body where it does not contain any organs. It is considered to react against the propagated electromagnetic field as a homogeneous model which consists of muscle only. It is well known that the human body is very complex, inhomogeneous, and built with different layers and tissues of different dielectric properties. To get realistic simulation results, the human dielectric property has been assigned to this model. The dielectric properties were extracted from the federal communications commission [41], and from the Italian national research council [42]. For muscle at 2.45 GHz, the conductivity is equal to 1.73 S/m, and the relative permittivity is 52.73, with a mass density of 1040 Kg/m³.

Figure 27:
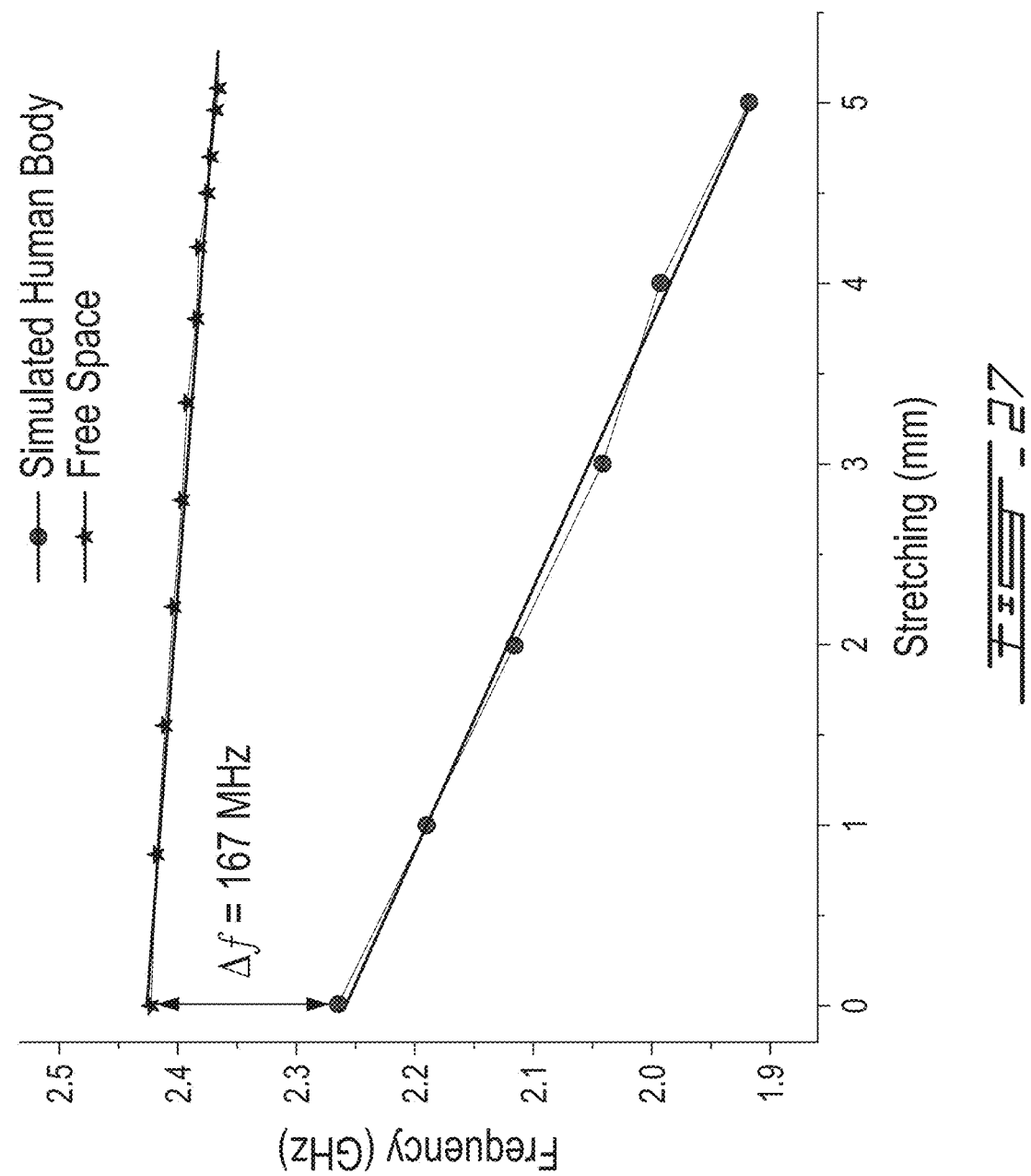
FIG. 27 is a graph showing resonance frequency as function of stretching on a simulated human body and in free space.

The central frequency shift of the spiral fiber antenna has been studied when placed on the SHB chest as a function of the induced stretching. The results are shown in FIG. 27. It can be seen that when the stretch is 0 cm, the central frequency shifts by 167 MHz from the free space frequency value. This shift is induced only by the SHB's dielectric properties. A monotonic decrease of the frequency shift is observed when the induced stretching deformation increases. This variation is similar to that observed in the free space with a clear detectable frequency difference.

Figure 28:
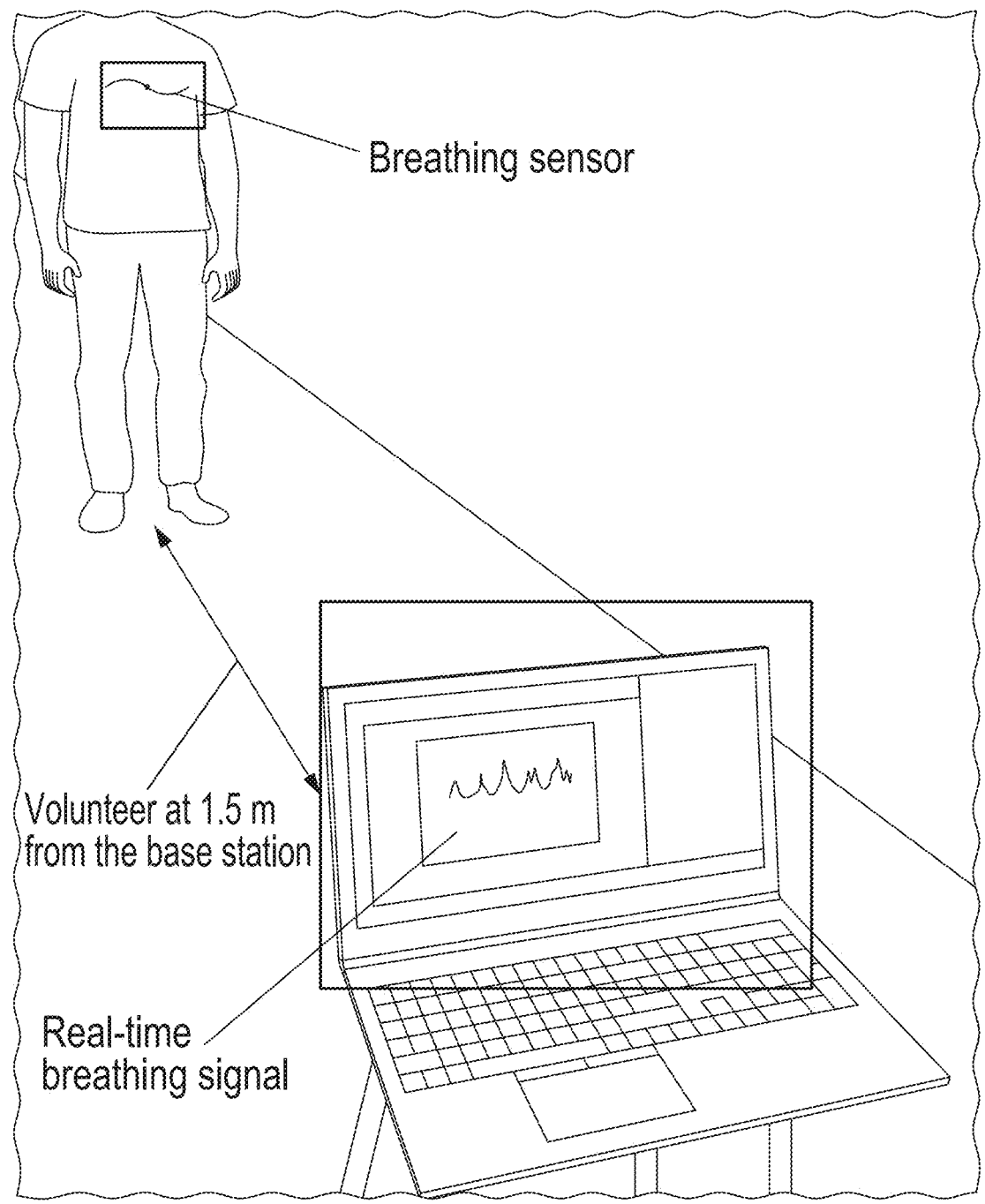
FIG. 28 is an image showing a respiration monitoring system including the wearable respiration sensor of FIG. 23, an interrogation system and a controller, the wearable respiration sensor being remotely positioned relative of the controller, in accordance with an embodiment.

The T-shirt has been tested with four healthy volunteers standing up (with no motion) in front of the base station. Breathing was performed at different rates and at different distances from the base station. The experimental layout is shown in FIG. 28.

Figures 29A, 29B:
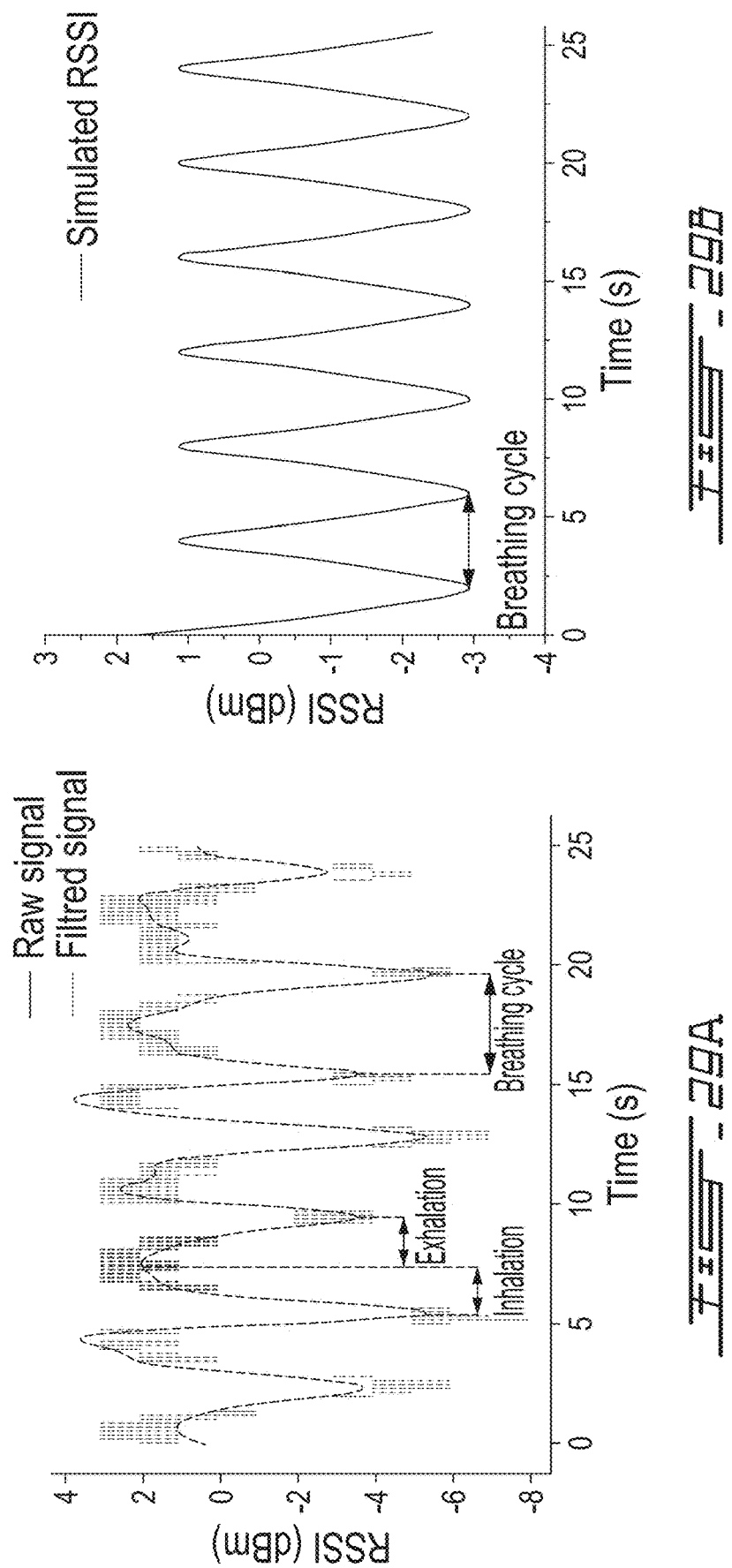
FIG. 29A is a graph showing a strength of a return signal as function of time, with a measured strength of the return signal in solid line and a measured strength of the return signal being filtered using a Butterworth filter in dashed line.
FIG. 29B is a graph showing a simulated strength of a return signal as function of time.

A volunteer was asked to take seven regular breaths in order to detect a correlation between the respiration and the received signal at the base station. FIG. 29A shows the RSSI measurements together with the filtered signal recorded for the volunteer standing at 0.5 m from the base station. The DC values from all the raw data recorded in this work were subtracted. From FIG. 29A, although the waveform is a little bit noisy, the breathing period is clear and can be distinguished. A bandpass Butterworth filter was used to improve the signal quality. As a consequence, the inhalation and the exhalation phases in each breathing period are clearly extracted, as shown in FIG. 29A. It was observed that the RSSI signal oscillates as the volunteer breathes. The breathing signal is unmistakably detected with seven breathing cycles (BCs) in 25 s. From this measurement, the inhalation and the exhalation period is estimated to be 3.57 s, which is in a good agreement with the regular BC (3 s to 5 s) reported in medical textbooks [43]. To confirm the experimental breath detection, the transmitted signal was simulated for a spiral fiber antenna placed horizontally on the chest of the SHB standing 0.5 m from the base station. In this simulation, inhalation and exhalation times were set to 2 s for each phase. In total the breathing cycle lasts for 4 s.

In FIG. 29, the result of the simulation were displayed within 25 s. The RSSI signal detected during the SHB's breath shows exactly six BCs, and each one lasts for 4 s. The signal variation follows the chest movement, hence, the breath signal of the SHB. The difference between the experimental and the simulated signal in terms of BCs is 3.57 s and 4 s, respectively. This difference could be explained by the fact that in a real environment, humans cannot maintain BCs times at precisely 4 s. Nevertheless, the simulation result and the experimental detection are in good agreement.

Figure 30:
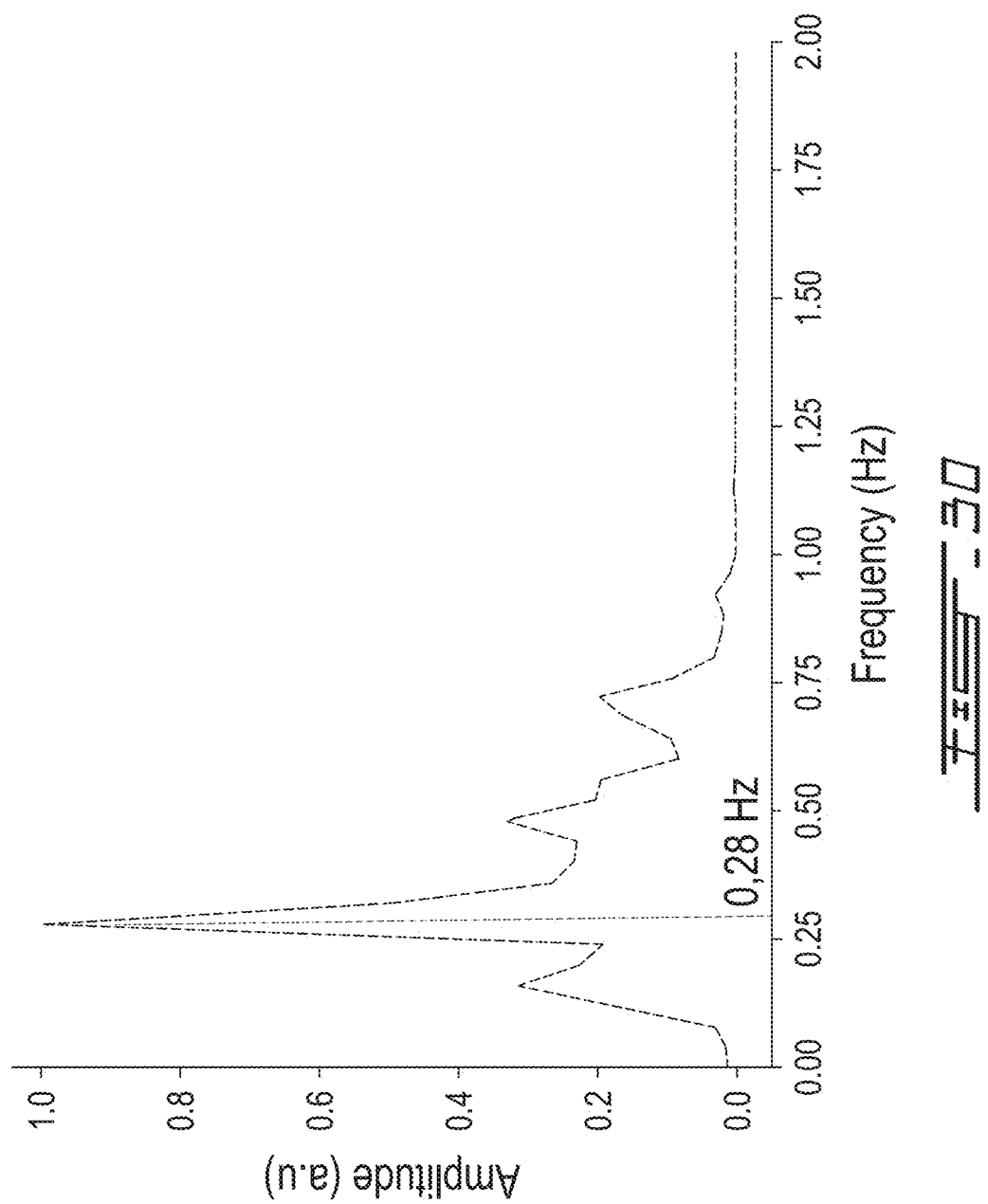
FIG. 30 is a graph showing an amplitude of fast Fourier Transform on the respiration data of FIG. 29A.

To derive the dominant frequency of real breaths, an FFT has been applied. The maximum frequency at the highest amplitude corresponds to the breathing rate frequency. As can be seen from FIG. 30, the measured peak is at ≈0.28 Hz, which corresponds to 16.8 bpm. This result is within the breathing rate range (12-18 bpm) for an adult as claimed in medical textbooks [43].

In Table 2, the breathing results have been summarized and obtained for the four volunteers who were breathing during 30 s without any restrictions on the number and rate of breaths. From this Table, it was observed that the designed sensor successfully detected different BCs for all the volunteers, corresponding to the different breathing rates chosen by each person.

TABLE 2

Breathing cycle (BC), breathing frequency (BF), and breathing rate (BR) were measured for four volunteers with different weight (W) and height (H) during 30 s. The number and the rate of breath were chosen by the volunteers.

| Volunteer | Age(years) | W (Kg) | H (cm) | BC | BF (Hz) | BR (bpm) |
|---|---|---|---|---|---|---|
| 1 | 35 | 102 | 190 | 5.5 | 0.183 | 11 |
| 2 | 38 | 95 | 185 | 4.5 | 0.150 | 9 |
| 3 | 22 | 65 | 160 | 5.0 | 0.167 | 10 |
| 4 | 31 | 88 | 185 | 6.0 | 0.200 | 12 |

BPM: breaths/min.

Figure 31A:
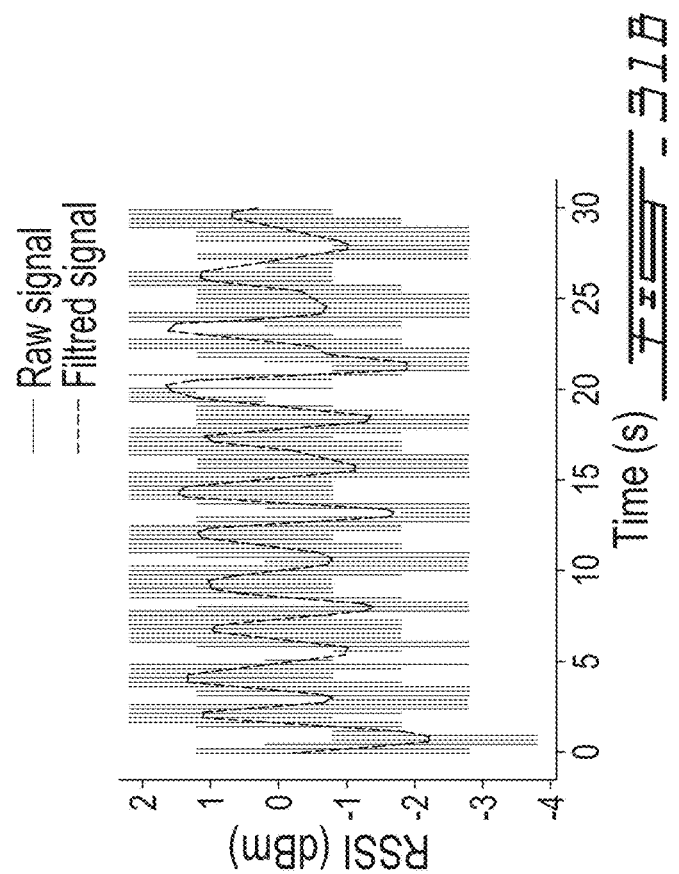

Four different breathing cycles were performed by two volunteers standing in front of the base station. The first volunteer performed slow (see FIG. 31A), shallow (see FIG. 31B), and irregular (see FIG. 31C) breathing, while the second volunteer performed fast breathing (see FIG. 31D), and a combination of none and deep long breaths (see FIG. 31E). For the slow breathing shown in FIG. 31A, the designed sensor detected five deep BCs over 30 s. The corresponding FFT calculation provides a breathing frequency at 0.17 Hz (FIG. 32A), leading to a breathing rate of 10.2 bpm.

Figure 31B:
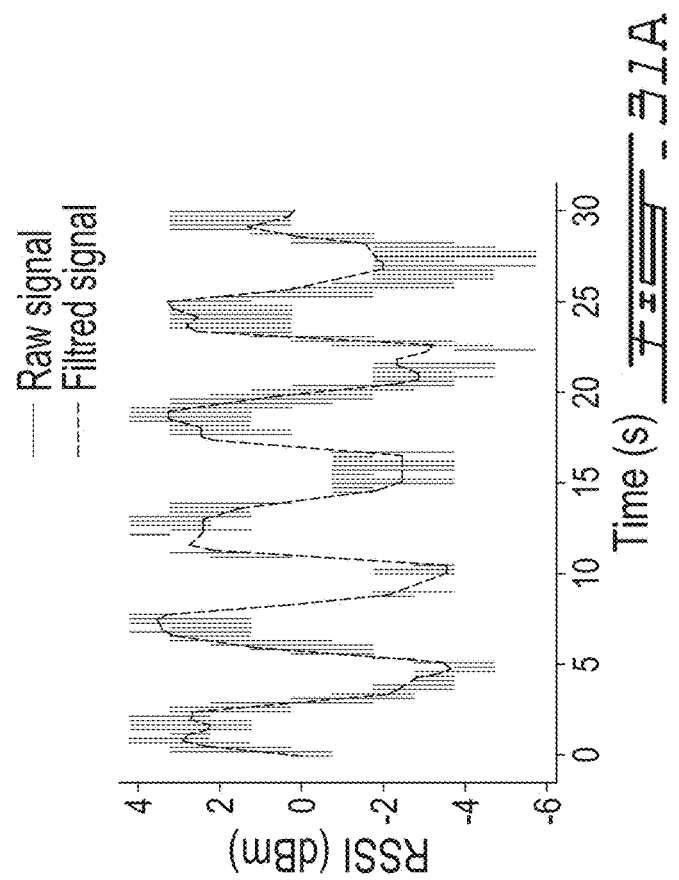

Shallow breathing is presented in FIG. 31B. The detected signal is small (two times less than the slow breathing signal) and noisy but still detectable, although it is difficult to accurately determine the inhalation and exhalation within one breath. Nonetheless, based on the filtered signal, 11 BCs performed by the volunteer in 30 s have been detected. In this case, the dominant frequency of the breathing was measured at 0.40 Hz, as shown in FIG. 32B, which corresponds to a breathing rate of 24 bpm.

It can be clearly seen that the respiration pattern in FIG. 31C is irregular within 25 s. The pattern shows overlapping of different BCs. Indeed the FFT calculations reveal the co-existence of four dominating frequencies at: 0.16 Hz, 0.29 Hz, 0.32 Hz, and 0.56 Hz as shown in FIG. 32C. In this case, estimating the breathing rate of the volunteer is not possible. Nonetheless, the breath sensor accurately detects the irregular breathing.

In FIG. 31D the fast breathing measurement results are presented. The designed system was able to detect 12 BC within 10 s. As shown in FIG. 32D, the dominant frequency obtained from the FFT is 1.17 Hz, which corresponds to 70.2 bpm.

In the last case, the volunteer was asked to stop his breath for 15 s and perform a long and deep breath in the next 15 s. The result is shown in FIG. 31E. During the first 15 s of the breathing waveform it was observed that the system did not detect any breathing signal. However, in the next 15 s the system recorded two clear BCs, which correspond to the two long deep breaths. The correlation between the breathing and the detected signal is clear.

In this example, a new wireless communication platform was presented to monitor in real time the breathing rate of a still individual via RSSI measurements. The system is composed of a non-invasive contactless sensor integrated into a stretchable T-shirt and a base station. The sensor is designed to operate at 2.4 GHz. It is based on a multi-material metal-glass-polymer fiber antenna in a spiral shape connected to a Bluetooth transmitter. The characteristics and the performances of the spiral fiber antenna were studied using ANSYS software. When the sensor is placed on the chest, the mechanism of breath detection is based on the central frequency shift of the fiber antenna due to the textile stretching induced by the chest movement. As a consequence, the variation of the signal amplitude during the breath is transmitted wirelessly to the base station. It was demonstrated the capability of the platform to detect the breath of four volunteers. Different breathing patterns and rates, such as slow, shallow, irregular, and fast respirations were also detected. The designed sensor is able to track a breathing with a frequency rate ranging from 0.16 to 1.2 Hz, which corresponds to a rate of 9.6â€"72 bpm. Numerical calculations of the simulated human breath support the experimental detection. The objective of this work is to present the concept and performance of the proposed sensor for human breathing detection. To validate these results, a comparison with gold standard equipment, such as a spirometer or a pneumotachograph, is required. This comparison should be interesting, particularly if the tests are performed on persons with respiratory problems.

[1] Lumb, A. B. Physiology Of Pulmonary Disease. In *Nunnâ€™s Applied Respiratory Physiology*, 8th ed.; Elsevier Health Sciences: 2016.

[2] Sebel, P.; Stoddart, M.; Waldhorn, R. E.; Waldman, C.; Whitfield, P. Respiration: The Breath of Life. In *Human Body*; Torstar Books, New York, USA: 1985.

[3] Murray, J. F. The Basis for Diagnosis and Treatment of Pulmonary Disease. In *The Normal Lung*, 2nd ed.; W.B. Saunders Co.: Philadelphia, Pa., USA, 1985.

[4] Walker, H. K.; Hall, W. D.; Willis Hurst, J. The History, Physical, and Laboratory Examinations. In *Clinical Methods*, 3rd ed.; Butterworths: Boston, Mass., USA, 1990.

[5] [-15] Elliott, M. A Narrative Review: Why is Respiratory Rate the Neglected Vital Sign? *Int. Arch. Nurs. Health Care* 2016, 2, 50.

[6] Flenady, T.; Dwyer, T.; Applegarth, J. Accurate respiratory rates count: So should you! *Australas. Emerg. Nurs. J.* 2017, 20, 45-47.

[7] Gupta, M.; Qudsi, H. Low Cost Thermistor based Respiratory Monitor. In Proceedings of the 39th Annual Northeast Bioengineering Conference, Syracuse, N.Y., USA, 5-7 Apr. 2013; pp. 287-288.

[8] Fabiola, A. C. Respiratory Monitoring System Based on the Thoracic Expansion Measurement. Master's Thesis, Department of Electrical Engeering, University of South Florida, FL, USA, January 2012.

[9] Bello, P. J.; Darling, C. J.; Lipoma, T. S. SOMNUS: A Sleep Diagnostics Shirt Employing Respiratory Patterns Through Chest Expansion. In Proceedings of the International Conference on Design of Medical Devices, Minneapolis, Minn., USA, 12-14 Apr. 2011; pp. 1-5.

[10] Grlica, J.; Martinoviü, T.; Dzapo, H. Capacitive Sensor for Respiration Monitoring. In Proceedings of the 2015 IEEE Sensors Applications Symposium, Zadar, Croatia, 13-15 Apr. 2015; pp. 1-6.

[11] Abbas, A. K.; Heimann, K.; Jergus, K.; Orlikowsky, T.; Leonhardt, S. Non-contact respiratory monitoring based on real-time infrared thermography. *Biomed. Eng. Online* 2011, 10, 93.

[12] Hsu, C. H.; Chow, C. J. Design and clinic monitoring of monitoring of a newly developed non-attached infant apnea monitor. *Biomed. Eng. Appl. Basis Commun.* 2005, 17, 126-134.

[13] Zhu, Z.; Fei, J.; Pavlidis, I. Tracking Human Breath in Infrared Imaging. In Proceedings of the 5th IEEE Symposium on Bioinformatics and Bioengineering (BIBE'05), Minneapolis, Minn., USA, 19-21 Oct. 2005; pp. 227-231.

[14] Bartula, M.; Tigges, T.; Muehlsteff, J. Camera-based System for Contactless Monitoring of Respiration. In Proceedings of the 2013 of the 35th Annual International Conference of the IEEE Engineering in Medicine and Biology Society (EMBC), Osaka, Japan, 3-7 Jul. 2013; pp. 2672-2675.

[15] Tan, K. S.; Saatchi, R.; Elphick, H.; Burke, D. Real-time vision based respiration monitoring system. In Proceedings of the 2010 7th International Symposium on Communication Systems, Networks and Digital Signal Processing (CSNDSP 2010), Newcastle, UK, 21-23 Jul. 2010; pp. 770-774.

[16] Fletcher, R.; Han, J. Low-cost differential front-end for doppler radar vital sign monitoring. In Proceedings of the 2009 IEEE MTT-S International Microwave Symposium Digest, Boston, Mass., USA, 7-12 Jun. 2009; pp. 1325-1328.

[17] Liu, L.; Liu, Z.; Barrowes, B. Through-wall bio-radiolocation with uwb impulse radar: Observation, simulation and signal extraction. *IEEE J-STARS*, 4, 791-798.

[18] Li, W.; Tan. B.; Piechocki, R. J. Non-Contact Breathing Detection Using Passive Radar. In Proceedings of the 2016 IEEE International Conference on Communications (ICC), Kuala Lumpur, Malaysia, 22-27 May 2016; pp. 1-6.

[19] Al Khalidi, F. Q.; Saatchi, R.; Burke, D.; Elphick, H. Facial tracking method for noncontact respiration rate monitoring. In Proceedings of the 2010 7th International Symposium on Communication Systems, Networks an Digital Signal Processing (CSNDSP 2010), Newcastle, UK, 21-23 Jul. 2010; pp. 751-754.

[20] Al Khalidi, F. Q.; Saatchi, R.; Burke, D.; Elphick, H.; Tan, S. Respiration rate monitoring methods: A review. *Pediatr. Pulmonol.* 2011, 46, 523-529.

[21] Atalay, O.; Kennon, W. R.; Demirok, E. Weft-knitted strain sensor for monitoring respiratory rate and its electro-mechanical modeling. *IEEE Sens. J.* 2015, 15, 110-122.

[22] Zhao, Z.; Yan, C.; Liu, Z.; Fu, X.; Peng, L. M.; Hu, Y.; Zheng, Z. Machine-Washable Textile Tribo electric Nano generators for Effective Human Respiratory Monitoring through Loom Weaving of Metallic Yarns. *Adv. Mater.* 2016, 28, 10267-10274.

[23] Mahbub, I.; Pullano, S. A.; Wang, H.; Islam, S. K.; Fiorillo, A. S.; To, G.; Mahfouz, M. R. A Low-Power Wireless Piezoelectric Sensor-Based Respiration Monitoring System Realized in CMOS Process. *IEEE Sens. J.* 2017, 17, 1858-1864.

[24] Witt, J.; Narbonneau, F.; Schukar, M.; Krebber, K.; De Jonckheere, J.; Jeanne, M.; Kinet, D.; Paquet, B.; DeprA, Ä""; Dâ€™Angelo, L. T.; et al. Medical Textiles With Embedded Fiber Optic Sensors for Monitoring of Respiratory Movement. *IEEE Sens. J.* 2012, 12, 246-254.

[25] Ciocchetti, M.; Massaroni, C.; Saccomandi, P.; Caponero, M. A.; Polimadei, A; Formica, D.; Schena, E. Smart Textile Based on Fiber Bragg Grating Sensors for Respiratory Monitoring: Design and Preliminary Trials. *Biosensors* 2015, 5, 602-615.

[26] Presti, D. L.; Massaroni, C.; Formica, D.; Saccomandi, P.; Giurazza, F.; Caponero, M. A.; Schena, E. Smart Textile Based on 12 Fiber Bragg Gratings Array for Vital Signs Monitoring. *IEEE Sens. J.* 2017, 17, 6037-6043.

[27] Gorgutsa, S.; Blais-Roberge, M.; Viens, J.; LaRochelle, S.; Messaddeq, Y. User-Interactive and Wireless-Communicating RF Textiles. *Adv. Mater. Technol.* 2016, 1, 1600032.

[28] Gorgutsa, S.; Khalil, M.; Belanger-Garnier, V.; Viens, J.; Gosselin, B.; LaRochelle, S.; Messaddeq, Y. Emissive Properties of Wearable Wireless-Communicating Textiles Made from Multimaterial Fibers. *IEEETrans. Antennas Propag.* 2016, 64, 2457-2464.
[29] Ravichandran, R.; Saba, E.; Chen, K.-Y.; Goel, M.; Gupta, S.; Patel, S. N. WiBreathe: Estimating Respiration Rate Using Wireless Signals in Natural Settings in the Home. In Proceedings of the 2015 IEEE International Conference on Pervasive Computing and Communications (PerCom), St. Louis, Mo., USA, 23-27 Mar. 2015; pp. 131-139.
[30] Patwari, N.; Wilson, J.; Ananthanarayanan, S.; Kasera, S. K.; Westenskow, D. R. Monitoring Breathing via Signal Strength in Wireless Networks. *IEEE Trans. Mob. Comput.* 2014, 13, 1774-1786.
[31] Kaltiokallio, O.; Yigitler, H.; Jantti, R.; Patwari, N. Non-invasive respiration rate monitoring using a single COTS TX-RX pair. In Proceedings of the 13th International Symposium on Information Processing in Sensor Networks, Berlin, Germany, 15-17 Apr. 2014; pp. 59-69.
[32] Kaltiokallio, O.; Yigitler, H.; Jantti, R.; Patwari, N. Catch a Breath: Non-invasive Respiration Rate Monitoring via Wireless Communication. *arXiv* 2013, arXiv: 1307.0084.
[33] Guay, P.; Gorgutsa, S.; LaRochelle, S.; Messaddeq, Y. Wearable Contactless Respiration Sensor Based on Multi-Material Fibers Integrated into Textile. *Sensors* 2017, 17, 1050.
[34] Sanderson, J. E.; Yeung, L. Y.; Yeung, D. T.; Kay, R. L.; Tomlinson, B.; Critchley, J. A.; Woo, K. S.; Bernardi, L. Impact of changes in respiratory frequency and posture on power spectral analysis of heart rate and systolic blood pressure variability in normal subjects and patients with heart failure. *Clin. Sci. (Lond.)* 1996, 91, 35-43.
[35] Yardley, L.; Grestyb, M.; Bronsteinb, A.; Beytsc, J. Changes in heart rate and respiration rate in patients with vestibular dysfunction following head movements which provoke dizziness. *Biol. Psychol.* 1996, 49, 95-108.
[36] Shaw, J. A. Radiometry and the Friis Transmission Equation. *Am. J. Phys.* 2013, 81, 33-37.
[37] Fawwaz, T. U.; Michelssen, E.; Ravaioli, U. *Fondamental of Applied Electromagnetics*, 6th ed.; Pearson: Hong Kong, China, 2010; pp. 33-37.
[38] [–15] Moore, R. K. Effects of a Surrounding Conducting Medium on Antenna *Analysis. Antennas Propag. IEEE Trans.* 1963, 11, 216-225.
[39] Karacolak, T.; Hood, A. Z.; Topsakal, E. Design of a Dual-Band Implantable Antenna and Development of Skin Mimicking Gels for Continuous Glucose Monitoring. *IEEE Trans. Microw. Theory Tech.* 2008, 56, 1001-1008.
[40] 3D Content Central. Human Heart. Available online: http://www.3dcontentcentral.com (accessed on 6 Feb. 2018).
[41] FCC. Body Tissue Dielectric Parameters. Available online: https://www.fcc.gov/general/body-tissue-dielectric-parameters (accessed on 6 Feb. 2018).
[42] Italian National Research Council. Body Tissue Dielectric Parameters. Available online: http://niremf.ifac.cnr.it/tissprop/htmlclie/htmlclie.php (accessed on 6 Feb. 2018).
[43] Youn, K. A.; Wse, A. J.; DeSaix, P.; Kruse, D. H.; Poe, B.; Johnson, E.; Johnson, J. E.; Korol, O.; Betts, J. G.; Womble, M. The Respiratory System. In *Anatomy and Physiology*; Hardcover, City, Country: 2013; pp. 145-152.

As can be understood, the examples described above and illustrated are intended to be exemplary only. Indeed, many variants are possible in alternate embodiments.

Figure 33A:
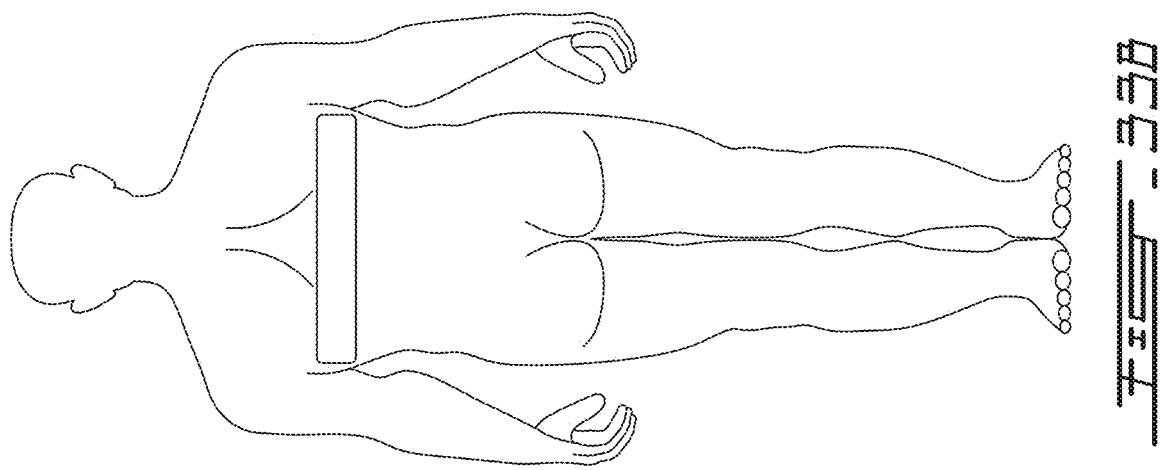
FIG. 33A-B are schematic views showing an embodiment where the substrate is worn partially around the torso, and a non-stretchable band connects two ends of the stretchable substrate around the back of the wearer.
Figure 33B:
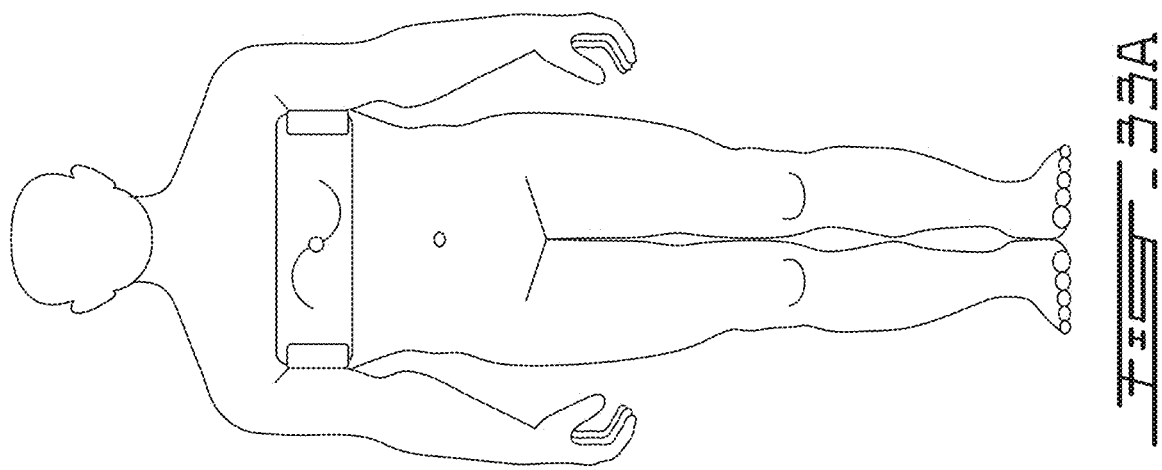

FIGS. 33A and 33B show one possible alternate embodiment. In the embodiment shown in FIGS. 33A and 33B, the stretchable substrate is worn around the front portion of a user's chest, and has two opposite ends. The two opposite ends are attached to one another via a textile (shown in FIG. 33B) which may not be stretchable. Indeed, in such an embodiment, the stretchable substrate can stretch and retract with the user's respiration even though it does not fully circumscribe the user's torso, with a rear portion of torso being circumscribed by a non-stretchable portion linking two opposite ends of the stretchable torso. Indeed, while it may be interesting to have the stretchable substrate extend to the sides of the user's back to maximise stretching, the center of the user's back typically does not stretch very much during respiration and there may be no advantage to having a stretchable portion extend along it.

Figure 34:
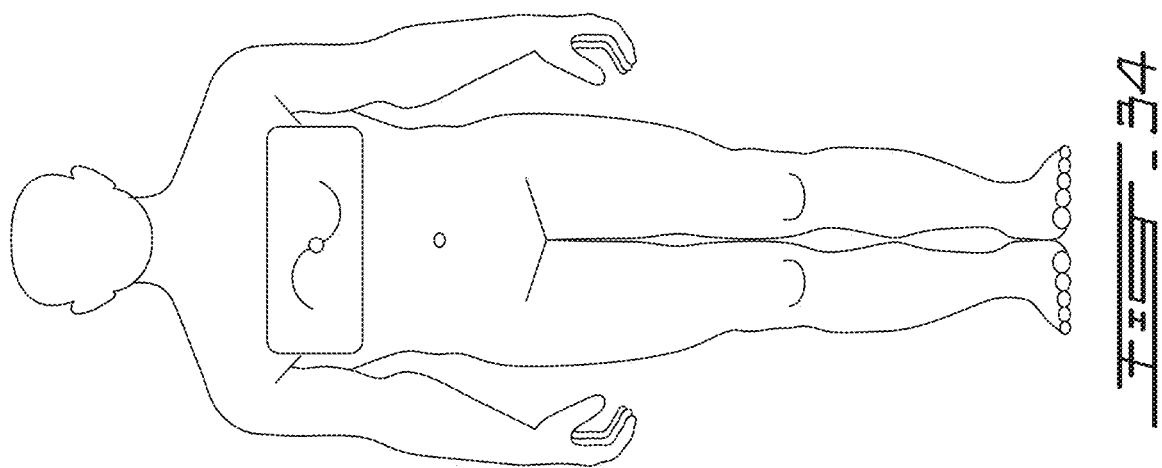
FIG. 34 is a schematic view showing an embodiment where the stretchable substrate is provided with an adhesive and is adhered to the front of the user's torso.

FIG. 34 shows still one other embodiment. In the embodiment of FIG. 34, the stretchable substrate has an adhesive backing, and is simply adhered to the user's chest in a manner that can be considered "worn around" the user's chest.

It will also be understood that in alternate embodiments, more than one sensor can be worn. The plurality of sensors can be worn at different areas of the user's torso and may allow one to obtain even more information about a user's respiration.

Indeed, in one embodiment, a sensor can have a stretchable substrate worn around a user's belly instead of a user's chest, for instance, and be used to obtain a signal indicative of a user's respiration.

The substrate does not have to be made of a woven textile to be stretchable. Non-woven textiles, and elastomeric materials, can have suitable stretchability characteristics for intended applications.

The scope is thus indicated by the appended claims.

What is claimed is:

1. A wearable respiration sensor comprising:
a stretchable substrate configured to be worn around a user's torso;
a dipole antenna having two flexible conductive elements extending in opposite directions from a center of the dipole antenna, relative to an axis of the dipole antenna intersecting the center, and being secured to the stretchable substrate, each one of the two flexible conductive elements having a proximate end near the center, a distal end away from the center, and a curved portion curving away from and back towards the axis of the dipole antenna between the proximate end and the distal end, in a plane of the stretchable substrate, the two flexible conductive elements being in a point reflection symmetry relative to one another relative to said center configured in a manner that, when the stretchable substrate is stretched by the user's respiration, the distal ends are moved relative to one another; and
a receiving port being electrically connected to the two flexible conductive elements.

2. The wearable respiration sensor of claim 1 further comprising an interrogation system having an emitter configured to emit a signal for transmission by the dipole antenna via the receiving port, and a receiver configured to, in response to said transmission, receive a return signal varying as function of the stretching of the dipole antenna.

3. The wearable respiration sensor of claim 2 wherein the emitter is remote from the wearable respiration sensor such that the emitter is remotely connected to the receiving port via a conductive wire.

4. The wearable respiration sensor of claim 2 wherein the emitter is made integral to the wearable respiration sensor such that the emitter is directly connected to the receiving port.

5. The wearable respiration sensor of claim 2 wherein the receiver is remote from the wearable respiration sensor.

6. The wearable respiration sensor of claim 5 wherein the receiver is communicatively coupled to the wearable respiration sensor via a wireless connection.

7. The wearable respiration sensor of claim 2 wherein the receiver is made integral to the wearable respiration sensor.

8. The wearable respiration sensor of claim 2 wherein the receiver is configured to measure a resonance frequency value based on the return signal, the resonance frequency value being indicative of a resonance frequency of the dipole antenna.

9. The wearable respiration sensor of claim 2 wherein the receiver is configured to measure a resonance frequency variation based on the return signal, the resonance frequency variation being indicative of a variation of a resonance frequency of the dipole antenna as the stretchable substrate is stretched.

10. The wearable respiration sensor of claim 2 wherein the receiver is configured to measure a strength of the return signal as the stretchable substrate is stretched.

11. The wearable respiration sensor of claim 2 further comprising a controller configured to receive data concerning the return signal from the interrogation system when the wearable respiration sensor is worn on the user's torso and as the stretchable substrate is stretched by respiration, and to determine respiration data based on the received data.

12. The wearable respiration sensor of claim 11 wherein the received data can be indicative of at least one of a resonance frequency value, a resonance frequency variation and a strength of the return signal.

13. The wearable respiration sensor of claim 11 wherein the controller and the interrogation system are made integral to the stretchable substrate.

14. The wearable respiration sensor of claim 1 wherein the dipole antenna is close to a user's chest when the wearable respiration sensor is worn around the user's torso.

15. The wearable respiration sensor of claim 14 wherein the center of the dipole antenna is disposed in a sagittal plane of the user's torso when the wearable respiration sensor is worn around the user's torso.

16. The wearable respiration sensor of claim 1 wherein the axis of the dipole antenna extends parallel to a transverse plane of the user's torso when the wearable respiration sensor is worn around the user's torso.

17. The wearable respiration sensor of claim 1 wherein the two flexible conductive elements are hollow capillary fibers made of polymer and having inner cavities coated with a conductive layer of silver.

18. The wearable respiration sensor of claim 1 wherein the stretchable substrate is made integral to a garment.

19. The wearable respiration sensor of claim 1 wherein the stretchable substrate is weaved into a garment.

20. The wearable respiration sensor of claim 1 wherein the dipole antenna is adhered to the stretchable substrate.

21. The wearable respiration sensor of claim 1 wherein the dipole antenna comprises a polymer coating protecting the two flexible conductive elements.

22. The wearable respiration sensor of claim 21 wherein the receiver is made integral to the wearable respiration sensor such that the receiver is directly connected to the receiving port.

23. The wearable respiration sensor of claim 21 wherein the emitter is remote from the wearable respiration sensor.

24. The wearable respiration sensor of claim 23 wherein the emitter is communicatively coupled to the wearable respiration sensor via a wireless connection.

25. The wearable respiration sensor of claim 1 further comprising an interrogation system having an emitter configured to emit a signal for reception by the dipole antenna via the receiving port, and a receiver configured to, in response to said emission, receive a return signal varying as function of the stretching of the dipole antenna.

26. The wearable respiration sensor of claim 1 wherein the stretchable substrate is configured to extend partially around a chest of the user.

27. The wearable respiration sensor of claim 1 wherein the stretchable substrate is configured to extend fully around a chest of the user.

28. The wearable respiration sensor of claim 1 wherein when the stretchable substrate is stretched along the axis of the dipole antenna, the curved portions of the two flexible conductive elements are flattened and the distal ends are moved away from one another.

29. A respiration monitoring sensor comprising:
a wearable respiration sensor having a stretchable substrate configured to be worn around a user's torso; a dipole antenna having two flexible conductive elements extending in opposite directions from a center of the dipole antenna, relative to an axis of the dipole antenna intersecting the center, and being secured to the stretchable substrate, each one of the two flexible conductive elements having a proximate end near the center, a distal end away from the center, and a curved portion curving away from and back towards the axis of the dipole antenna between the proximate end and the distal end, in a plane of the stretchable substrate, the two flexible conductive elements being in a point reflection symmetry relative to one another relative to said center configured in a manner that, when the stretchable substrate is stretched by the user's respiration, the two distal ends are moved relative to one another; and a receiving port being electrically connected to the two flexible conductive elements;
an interrogation system being communicatively coupled to the wearable respiration sensor, the interrogation system having an emitter configured to emit a signal for at least one of transmission and reception by the dipole antenna via the receiving port, and a receiver configured to, in response to said emission, receive a return signal varying as function of the stretching of the dipole antenna; and
a controller being communicatively coupled to the interrogation system, the controller being configured to receive data concerning the return signal and to generate respiration data based on the received data.

* * * * *

UNITED STATES PATENT AND TRADEMARK OFFICE
CERTIFICATE OF CORRECTION

PATENT NO. : 11,589,774 B2
APPLICATION NO. : 16/397338
DATED : February 28, 2023
INVENTOR(S) : Stepan Gorgutsa et al.

It is certified that error appears in the above-identified patent and that said Letters Patent is hereby corrected as shown below:

On the Title Page

Item (72) The last name of the third inventor should read "Messaddeq" rather than "Messadeq".

Signed and Sealed this
Fifth Day of March, 2024

Katherine Kelly Vidal
*Director of the United States Patent and Trademark Office*